US005863532A

United States Patent [19]
Traugh et al.

[11] Patent Number: 5,863,532
[45] Date of Patent: Jan. 26, 1999

[54] COMPOSITIONS AND METHODS COMPRISING CYTOSTATIC PROTEIN KINASE

[75] Inventors: Jolinda A. Traugh, Riverside; Regina D. Rooney, Del Mar; Rolf Jakobi; Polygena T. Tuazon, both of Riverside; Charng-Jui Chen, Sierra Madre, all of Calif.; William E. Meek, Colorado Springs, Colo.; Edward J. Carroll, Jr.; Curtis A. Monnig, both of Riverside, Calif.

[73] Assignee: The Regents of the University of California, Oakland, Calif.

[21] Appl. No.: 615,942

[22] Filed: Mar. 14, 1996

[51] Int. Cl.[6] .............................. A61K 38/51; C12N 9/12; C12P 21/06; C07H 21/04

[52] U.S. Cl. ........................ 424/94.5; 435/194; 435/69.1; 435/252.3; 435/320.1; 536/23.2; 530/350; 514/2

[58] Field of Search ................................. 514/2; 424/94.5; 435/194, 69.1, 252.3, 320.1; 536/23.2

[56] References Cited

U.S. PATENT DOCUMENTS 5,518,911  5/1996  Abo et al. ............................... 435/194

OTHER PUBLICATIONS

Bagrodia, S., et al., "Identification of a Mouse p21$^{Cdc42/Rac}$ Activated Kinase", *J. Biol. Chem.*, 270(39):22731–22737 (1995).

Cosco, O. A., et al., "The Small GTP–Binding Proteins Rac1 and Cdc42 Regulate the Activity of the JNK/SAPK Signaling Pathway", *Cell*, 81:1137–1146 (1995).

Evans, G. A., "Specific Protein Kinases Modulated during T Cell Mitogenesis", *J. Biol. Chem.*, 267(15):10313–10317 (1992).

Fu, X., et al., "Site–specific Phosphorylation of Avian Retrovirus Nucleocapsid Protein pp12 Regulates Binding to Viral RNA", *J. Biol. Chem.*, 260(17):9941–9947 (1985).

Fu, X., et al., "Site–directed Mutagenesis of the Avian Retrovirus Nucleocapsid Protein, pp12, at Serine 40, the Primary Site of Phosphorylation in vivo", *J. Biol. Chem.*, 263(5):2134–2139 (1988).

Hanks, S. K., et al., "The Protein Kinase Family: Conserved Features and Deduced Phylogeny of the Catalytic Domains", *Science*, 241:42–52 (1988).

Hanks, S. K., et al., "Protein Kinase Catalytic Domain Sequence Database: Identification of Conserved Features of Primary Structure and Classification of Family Members", *Methods Enzymol.*, 200:38–62 (1991).

Herskowitz, I., "MAP Kinase Pathways in Yeast: For Mating and More", *Cell*, 80:187–197 (1995).

Jakobi, R., et al., "Human phosvitin/casein kinase type II Molecular cloning and sequencing of full–length cDNA encoding subunit beta", *Eur. J. Biochem.*, 183:227–233 (1989).

Knaus, U. G., et al., "Regulation of Human Leukocyte p21–Activated Kinases Through G Protein—Coupled Receptors", *Science*, 269:221–223 (1995).

Lederer, E., et al., "The protein kinase homologue Ste20p is required to link the yeast pheromone response G–protein βγ subunits to downstream signalling components", *EMBO J.*, 11(13):4815–4824 (1992).

Leis, J., et al., "Effects of Phosphorylation of Avian Retrovirus Nucleocapsid Protein pp12 on Binding of Viral RNA", *J. Biol. Chem.*, 259(12):7726–7732 (1984).

Manser, E., et al., "Purification and Assay of Kinases That Interact with Rac/Cdc42", *Methods Enzymol.*, 256:215–227 (1995).

Manser, E., et al., "A brain serine/threonine protein kinase activated by CDC42 and Rac1", *Nature*, 367:40–46 (1994).

Manser, E., et al., "Molecular Cloning of a New Member of the p21–Cdc42/Rac–activated Kinase (PAK) Family", *J. Biol. Chem.*, 270(42):25070–25078 (1995).

Marcus, S., et al., "Shk1, a homolog of the *Saccharomyces cerevisiae* Ste20 and mammalian p65$_{PAK}$ protein kinases, is a component of a Ras/Cdc42 signaling module in the fission yeast *Schizosaccharomyces pombe*", *PNAS (USA)*, 92:6180–6184 (1995).

Martin, G. A., et al., "A novel serine kinase activated by rac1/CDC42Hs–dependent autophosphorylation is related to PAK65 and STE20", *EMBO J.*, 14(9):1970–1978 (1995).

Meek, W. E., "Protease Activated Kinase 1 (PAK 1) is phosphorylated by Casein Kinase II and Protein Kinase C", *FASEB J.*, 6:A1852 (Abstract 5304) (1992).

Minden, A., et al., "Selective Activation of the JNK Signaling Cascade and c–Jun Transscriptional Activity by the Small GTPases Rac and Cdc42Hs", *Cell*, 81:1147–1157 (1995).

(List continued on next page.)

*Primary Examiner*—Robert A. Wax
*Assistant Examiner*—Tekchand Saidha
*Attorney, Agent, or Firm*—Fulbright & Jaworski L.L.P.

[57] ABSTRACT

The present invention presents a unique class of physiological suppressors of cell division and cleavage. In particular, the present invention presents p21-activated protein kinase PAK I, also known as protease activated protein kinase I (with the same abbreviation "PAK I") which has been purified to apparent homogeneity. PAK I is inactive, e.g. as a protein of about 60 kDa (denoted "p60", as determined by polyacrylamide gel electrophoresis) and is active when autophosphorylated, for example, following limited proteolysis, or binding of Cdc42, e.g., as a protein of about 58 kDa (denoted "p58" as determined by polyacrylamide gel electrophoresis). The present invention also presents a fragment of PAK I, a peptide denoted p37, which contains the catalytic domain of PAK I. The purification, characterization, nucleotide and amino acid sequences of PAK I and p37 are also disclosed. Another aspect of the invention discloses the cytostatic activity of PAK I and its fragments. Further disclosed are the uses of these proteins and peptides for diagnosing and treating diseases, especially for cancer.

11 Claims, 15 Drawing Sheets

OTHER PUBLICATIONS

Mischak, H., et al., "Overexpression of Protein Kinase C–δ and –ε in NIH 3T3 Cells Induces Opposite Effects on Growth, Morphology, Anchorage Dependence, and Tumorigenicity", *J. Biol. Chem.*, 268(9):6090–6096 (1993).

Munemitsu, S., et al., "Molecular Cloning and Expression of a G25K cDNA, the Human Homolog of the Yeast Cell Cycle Gene CDC42", *Mol. Cell. Biol.*, 10(11):5977–5982 (1990).

Nishizuka, Y., "Intracellular Signaling by Hydrolysis of Phospholipids and Activation of Protein Kinase C", *Science*, 258:607–613 (1992).

Ottilie, S., et al., "Fission yeast pak1+encodes a protein kinase that interacts with Cdc42p and is involved in the control of cell polarity and mating", *EMBO J.*, 14;5908–5919 (1995).

Pendergast, A. M., et al., "Identification of three protein kinases which phosphorylate threonyl–tRNA synthetase from rat liver", *FEBS 4091*, 206(2):335–337 (1986).

Planas–Silva, M. D., et al., "Expression of a constitutive form of calcium/calmodulin dependent protein kinase II leads to arrest of the cell cycle in $G_2$", *EMBO J.*, 11(2)507–517 (1992).

Prigmore, E., et al., "A 68–kDa Kinase and NADPH Oxidase Component $p67^{phox}$ Are Targets for Cdc42Hs and Rac1 in Neutrophils", *J. Biol. Chem.*, 270(18):10717–10722 (1995).

Ramer, S. W., et al., "A dominant truncation allele identifies a gene, STE20, that encodes a putative protein kinase necessary for mating in *Saccharomyces cerevisiae*", *PNSA (USA)*, 90:452–456 (1993).

Rooney, R. D., et al., "Identification of Inactive and Active Forms of Protease Activated Protein Kinase I in 3T3-L1 Cells", *FASEB J.*, 6:A1852 (Abstract 5305) (1992).

Rooney, R. D., et al., "Injection of Quiescence Initiating Protein Kinase Into Early Frog Embryos Inhibits Cell Division", *FASEB J.*, 7:A1213 (Abstract 935) (1993).

Sagata, N., et al., "The c–mos proto–oncogene product is a cytostatic factor responsible for meiotic arrest in vertebrate eggs", *Nature(London)*, 342:512–518 (1989).

Shinjo, K., et al., "Molecular cloniung of the gene for the human placental GTP–binding protein $G_p$ (G25K): Identification of this GTP–binding protein as the human homolog of the yeast cell–division cycle protein CDC42", *PNAS (USA)*, 87:9853–9857 (1990).

Tahara, S. M., et al., "Cyclic Nucleotide–Independent Protein Kinases from Rabbit Reticulocytes", *J. Biol. Chem.*, 256(22):11558–11564 (1981).

Tahara, S. M., "Differential Activation of Two Protease–Activated Protein Kinases from Reticulocytes by a $Ca^{2+}$—Simulated Protease and Identification of Phosphorylated Translational Components", *Eur. J. Biochem.*, 126:395–399 (1982).

Teo, M. et al., "Identification and Molecular Cloning of a $p21^{cdc42/rac1}$–activated Serine/Threonine Kinase That is Rapidly activated by Thrombin in Platelets", *J. Biol. Chem.*, 270(44):26690–26697 (1995).

Traugh, J. A., et al., "Isolation of Acetyltransferase Activities from Rabbin Reticulocytes and Modification of Translational Components", *Meth. Enzymol.*, 60:534–541 (1979).

Tuazon, P. T., et al., "Phosphorylation of Myosin Light Chain by a Protease–Activated Kinase from Rabbit Skeletal Muscle", *Eur. J. Biochem.*, 129:205–209 (1982).

Tuazone, P. T., et al., "Activation of Actin–activated ATPase in Smooth Muscle by Phosphorylation of Myosin Light Chain with Protease–activated Kinase I", *J. Biol. Chem.*, 259(1):541–546 (1984).

Tuazon, P. T., et al., "Comparative Analysis of Phosphorylation of Translaional Initiation and Elongation Factors by Seven Protein Kinases", *J. Biol. Chem.*, 264(5):2773–2777 (1989).

Wang, E., "A 57,000–mol–wt Protein Uniquely Present in Nonproliferating Cells and Senescent Human Fibroblasts", *J. of Cell Biol.*, 100:545–551 (1985).

Wang, E., "Disapparence of Statin, a Protein Marker for Non–Proliferating and Senescent Cells, Following Serum–Stimulated Cell Cycle Entry", *Experimental Cel. Res.*, 167:135–143 (1986).

Watanabe, T., et al., "Cell division arrest induced by phorbol ester in CHO cells overexpressing protein kinase C–δ subspecies", *PNAS (USA)*, 89:10159–10163 (1992).

Zhang, S., et al., "Rho Family GTPases Regulates p38 Mitogen–activated Protein Kinase through the Downstream Mediator Pak1", *J. Biol. Chem.*, 270(41):23934–23936 (1995).

FIG. 1A

```
      .         .         .         .         .         .
GGGAGCTCGGACGGAGGCGCCTCGCCGGGGCGGGGACCTTTCCTCGCCTGGGGTCATTTC    60

.         .         .         .         .         .
ATAACTCTGAATCATGTCTGATAACGGAGAACTGGAAGACAAGCCTCCAGCACCTCCTGT   120
            M  S  D  N  G  E  L  E  D  K  P  P  A  P  P  V    16

.         .         .         .         .         .
GCGAATGAGCAGCACCATCTTTAGCACTGGAGGCAAAGACCCCTTGTCAGCCAATCACAG   180
 R  M  S  S  T  I  F  S  T  G  G  K  D  P  L  S  A  N  H  S    36
                     ‾  ‾  ‾  ‾  ‾  ‾  ‾  ‾  ‾  ‾  ‾  ‾  ‾

.         .         .         .         .         .
CTTGAAGCCTTTGCCCTCTGTTCCAGAAGAAAAAAAGCCAAGGAATAAAATCATCTCCAT   240
 L  K  P  L  P  S  V  P  E  E  K  K  P  R  N  K  I  I  S  I    56
 ‾

.         .         .         .         .         .
ATTCTCAGGCACAGAAAAAGGAAGTAAAAAGAAAGAAAAAGAACGACCAGAGATTTCTCC   300
 F  S  G  T  E  K  G  S  K  K  K  E  K  E  R  P  E  I  S  P    76

.         .         .         .         .         .
TCCCTCTGATTTTGAGCACACCATCCACGTCGGCTTCGATGCTGTTACTGGAGAATTCAC   360
 P  S  D  F  E  H  T  I  H  V  G  F  D  A  V  T  G  E  F  T    96

.         .         .         .         .         .
CGGCATGCCGGAGCAGTGGGCACGCCTGCTGCAGACGTCCAACATCACCAAACTCGAGCA   420
 G  M  P  E  Q  W  A  R  L  L  Q  T  S  N  I  T  K  L  E  Q   116
       ‾  ‾  ‾  ‾  ‾  ‾  ‾  ‾  ‾  ‾  ‾  ‾  ‾  ‾  ‾  ‾  ‾  ‾

.         .         .         .         .         .
GAAGAAGAACCCACAGGCAGTGCTGGACGTGCTCAAGTTCTATGACTCCAACACCGTGAA   480
 K  K  N  P  Q  A  V  L  D  V  L  K  F  Y  D  S  N  T  V  K   136
 ‾  ‾

.         .         .         .         .         .
GCAGAAGTACCTGAGCTTCACTCCTCCGGAGAAAGATGGCTTCCCTTCTGGAGCACCAGC   540
 Q  K  Y  L  S  F  T  P  P  E  K  D  G  F  P  S  G  A  P  A   156
                               ‾  ‾  ‾  ‾  ‾  ‾  ‾  ‾  ‾  ‾

.         .         .         .         .         .
ACTGAATACCAAGGTATCAGAAACATCAGCAGTAGTAACAGAAGAAGATGACGATGACGA   600
 L  N  T  K  V  S  E  T  S  A  V  V  T  E  E  D  D  D  D  E   176
 ‾  ‾  ‾  ‾  ‾  ‾  ‾  ‾  ‾  ‾  ‾  ‾  ‾

.         .         .         .         .         .
AGAGGCGGCACCTCCTGTTATTGCCCCACGGCCAGATCATACAAAATCAATTTATACACG   660
 E  A  A  P  P  V  I  A  P  R  P  D  H  T  K  S  I  Y  T  R   196

.         .         .         .         .         .
GTCTGTAATTGACCCTATTCCTGCACCAGTTGGTGATTCTCATGTTGATAGTGGTGCCAA   720
 S  V  I  D  P  I  P  A  P  V  G  D  S  H  V  D  S  G  A  K   216
 ‾  ‾  ‾  ‾  ‾  ‾  ‾  ‾  ‾  ‾  ‾  ‾  ‾  ‾
 ↑
      .         .         .         .         .         .
GTCTTCAGATAAACAGAAAAAGAAAACCAAGATGACAGATGAAGAGATTATGGAGAAATT   780
 S  S  D  K  Q  K  K  K  T  K  M  T  D  E  E  I  M  E  K  L   236
```

FIG. 1B

```
       .         .         .         .         .         .         .
ACGAACTATTGTGAGCATAGGTGACCCTAAGAAAAAATATACAAGATATGAAAAAATTGG        840
 R  T  I  V  S  I  G  D  P  K  K  K  Y  T  R  Y  E  K  I  G        256
                            ↑
       .         .         .         .         .         .         .
ACAAGGGGCTTCTGGTACAGTTTTCACTGCTACTGATGTGGCATTGGGACAGGAGGTTGC        900
 Q  G  A  S  G  T  V  F  T  A  T  D  V  A  L  G  Q  E  V  A        276
                                        _  _  _  _  _  _  _  _
       .         .         .         .         .         .         .
TATCAAACAGATTAATTTACAGAAACAGCCAAAGAAGGAATTGATCATTAATGAAATTCT        960
 I  K  Q  I  N  L  Q  K  Q  P  K  K  E  L  I  I  N  E  I  L        296
 _  _  _  _  _  _  _  _  _  _  _  _  _  _  _  _  _
       .         .         .         .         .         .         .
GGTGATGAAAGAGTTAAAAAATCCCAACATAGTTAACTTCTTGGACAGTTACCTAGTGGG       1020
 V  M  K  E  L  K  N  P  N  I  V  N  F  L  D  S  Y  L  V  G        316
       _  _  _  _  _  _  _  _  _  _  _
       .         .         .         .         .         .         .
AGATGAATTATTCGTGGTAATGGAGTACCTTGCTGGTGGCTCACTTACTGATGTTGTAAC       1080
 D  E  L  F  V  V  M  E  Y  L  A  G  G  S  L  T  D  V  V  T        336
       .         .         .         .         .         .         .
AGAAACCTGCATGGATGAAGCGCAGATTGCAGCTGTGTGCAGAGAGTGTTTACAGGCTTT       1140
 E  T  C  M  D  E  A  Q  I  A  A  V  C  R  E  C  L  Q  A  L        356
       _  _  _  _  _  _  _  _  _  _  _  _  _  _  _  _
       .         .         .         .         .         .         .
GGAGTTTTTACATGCTAATCAAGTGATCCACAGAGACATCAAAAGTGACAATGTGCTTTT       1200
 E  F  L  H  A  N  Q  V  I  H  R  D  I  K  S  D  N  V  L  L        376
 _  _  _  _  _  _  _  _  _  _  _
       .         .         .         .         .         .         .
GGGGATGGAAGGATCAGTTAAACTTACTGACTTTGGTTTCTGTGCCCAGATCACCCCTGA       1260
 G  M  E  G  S  V  K  L  T  D  F  G  F  C  A  Q  I  T  P  E        396
       .         .         .         .         .         .         .
GCAGAGTAAACGCAGTACCATGGTTGGAACGCCTTACTGGATGGCACCCGAGGTGGTTAC       1320
 Q  S  K  R  S  T  M  V  G  T  P  Y  W  M  A  P  E  V  V  T        416
       .         .         .         .         .         .         .
ACGGAAAGCATATGGCCCTAAAGTCGACATATGGTCTCTGGGCATCATGGCTATTGAGAT       1380
 R  K  A  Y  G  P  K  V  D  I  W  S  L  G  I  M  A  I  E  M        436
       .         .         .         .         .         .         .
GGTAGAAGGAGAACCTCCATACCTCAATGAAAATCCCTTGAGGGCCTTGTACCTGATAGC       1440
 V  E  G  E  P  P  Y  L  N  E  N  P  L  R  A  L  Y  L  I  A        456
 _  _  _  _  _  _  _  _  _  _  _  _  _  _  _  _  _  _  _  _
       .         .         .         .         .         .         .
AACTAATGGAACCCCAGAACTTCAGAATCCAGAGAAGCTTTCCCCCATATTTCGGGATTT       1500
 T  N  G  T  P  E  L  Q  N  P  E  K  L  S  P  I  F  R  D  F        476
 _
       .         .         .         .         .         .         .
CTTAAATCGATGTTTGGAAATGGATGTGGAGAAGAGAGGTTCAGCCAAAGAACTGCTGCA       1560
 L  N  R  C  L  E  M  D  V  E  K  R  G  S  A  K  E  L  L  Q        496
                   _  _  _  _  _  _  _  _  _  _  _  _  _  _
```

FIG. 1C

```
GCATCCCTTCCTGAAACTGGCCAAACCATTATCCAGCTTGACACCACTCATCATGGCAGC  1620
  H  P  F  L  K  L  A  K  P  L  S  S  L  T  P  L  I  M  A  A    516

TAAAGAAGCAATGAAGAGTAACCGCTAACATCAGTGCCGTGGCCTCATGTTCCTTTGTCC  1680
  K  E  A  M  K  S  N  R  *                                     524

ATTTCCTAAAAGAAGTCTTTTAATATATGAAAGTTACTGCTCTTTTCGGGGTTTAAAGAA  1740

ATGGTCTGAATAATGGAGGAAAAACAAAGCTACTATTTCTTGAAGACAACTAAGACAAAA  1800

TTGCAAAAAGAGAATCATGACTTTCAGATGAACCCCTTCTTTAGGGTCCAAAGGAATTGT  1860

GGACTGAGTCACTCGCCTTACATCTTTCAGCAGACAGCCGTCAGGACTTGTTCCTTATGC  1920

TTGAGATTTGCATTTTATTTTGCTAACTTTGTTGGAATAGATCCCATTCTTGTCCCCTTT  1980

GGGGTGTTTTCAATACTTGAAGGGCAGATTCGAGTTTTTCAGCATATTTGTTTCACCTGC  2040

TGGTCTTCTCTCTCCTTCAGAGCTCTCCTTTTCCTCGACTTGCTCCTTTTGAGTTGCTTT  2100

GAGAACTTTTTGTCGTGCCTGAATTCAAGGCAAGTATGATAGAAATTGTGCAGCTCCTCA  2160

TTGGCAAAGGAGCTCAGCATAGTTTAACTTTGTATAGAAGTTAGGACCAGCAATGGTTTC  2220

ATGGAATATTTCAGTTCAGAACTTGAACTGAAAGAAGGGAAGAAAAGTATGTGATTTTTA  2280

CCTTTTTAACAAATGTGAAAGGGTCACTTTGAGAAATCTCATGGTGGTGAGTTTGGAGTT  2340

TGTTACATGTATAGAAAGAAGACTAATCTATATTTATAACTAAAATCACTGAGACAAAAA  2400

AGAATCCCGGCGACTGTACACCTGACGGTTTTGTCTTCCTTTCTGCCTTTCTCCTCTTCA  2460

GATTTGGCTTGAGGAGGAACCAAAGTGATTTTCTTGTTCCAGCTTGGGCTTTATGACTG  2520

GTTAGTGCCATTACCTTTCCTTTCCTCCTTTCCTCTTTCATTTTGGAAATAAGTTTCTGT  2580

ATATGTTGCAATTTTAGGTTTAGTTTTTTGTTTTGTTTTTATGTAACCCTCTCACCTT    2640
```

FIG. 1D

```
ACATATCCTGTTCATACCACATCCTACTCTGTAATAATCATTGAATTTTCAGAATTTGAA 2700
                                                        ↑
AATTAACTTTTGTTTTCCACTTAAAGGGAAAAATATTTGGGGTTAGCAGAGACAAAGTGA 2760
GAGATTGAACTTTAGTGAGTTGTAGAATAATTAGTTGAGACTGTATTCATGAGAGAGAAA 2820
TGTCAGTATTACAGAGTTCCAAATGATGACGAGTAAACTGTAAAGGCTGTCATAAGTTAG 2880
AGTGATTCTAACACATTACCAGTGTGTTACTGTGTAAGAGAACTTAAATGAGAAGGTTCT 2940
TGGTGGATTCACGGATCATTGGAGATGTGGAATTACTTTAGTATTTTTTTTTTTTTCAG 3000
AGAAGTAGAGAATATTCATGTAAAAATCTGAGGAAAAGAAAAATGCGGTATTGATAGGAA 3060
TCCTTTTTTATTTTAAAGATTAAGAAAAGGTCTGTGACCTGTTAATTATGAGAATGCCCC 3120
TTCCTCCCCTTCCCTTCTGTGCTTTACTCTCCTGTTCTTCTCTCCTCATTTCTCGGTTGT 3180
TTGGCTTTTGGGTGAGGAATGGTCTACTCTGACATGCCTTGAACCACATAAAAAAGTCTT 3240
CGGTTGAGTTCTGGTATTTTGTTCCCACCATGCCCTCCCAGTGAAATTCACACCTGCTTG 3300
CCATCCTGCAATAGTACAAATCATTAATGAAAATAAGTATGCTGTTTTGTAGTATATTGG 3360
AAAACCAGCAGAGTTTTATTTCCTGTTATTCCCGTCGTATCTGTGTTAAGACACAGATAT 3420
CAGTGTAGAATGACTATTTTGTGTTGATACCACAGAAAGATTTTCAGAAAAATGAGTAAA 3480
ATAATTAATGAAACTTTTATATAGAGCACTTAATGATCTCTGATACCAGTATGGTTCTTG 3540
ATTGCATTTTTCTCTGGACTATATTGGCCTTCTACAGCTCTTACTAAATTATAGAAACAA 3600
GCTGGTTTATTTCTGGTGGAAAGCTACAGTGCCCCTTAACTTCCAGATTTGAGCACTCTT 3660
TGTAGACGATTGGATGGATGGATCATGATGAAGATGCTGCCAATGAGAGAGAGAGAAAAC 3720
ACCGACTAGATGATGAGACTGATCATCATGACCACTTAAGAAGGCGCTTCCCATCCTAAG 3780
TCATAAGGACTTTTTCCCTCGAATCTGTGCCAGGGCCCCAGTTTATGCTTGTGGTGACAA 3840
```

FIG. 1E

```
CAAAGGGCCTTTCAGACGGTGGAAGCAGTTTGGGATTTGTATTTACAGCCTCTCGGATGG 3920
TTACCTGCACGTCCATTGCTGGCAACGGACTTTGAAATCTGACTCCTTGGTTAAGGGAGC 3980
TACACTGTGGTGTATTCTTTACTTACCTGGATAAACTAACCTGTAATAGAAGTATACTTT 4020
AGTAAATTCTGAAATGTGTCATTTTTAAACAAAATAATCCTGAAAGCAATATGAAATTGT 4080
GATTTATTAGTTATTTTAAATTAAAATGTTCAGATCTTCTTGAAAGAACTACTGTATCTG 4140
                              ↑
AATCAAGATTCTTGTTTTTTAATAATTGCTTTTTATATTCATCTTTTTTGTCACCACTT  4200
CAGGGTGAAAATTCCCATTTAAATCTGAAAATTACGTTAGTCATCTTGTATTACTAGGGC 4260
AATATTACTGTAATACTTATTTATGATATTTTAACCTCTCTGGTGGTCTTTAAGTTATCT 4320
TCTACTCTTGTTCCTTGTGCTGCTTTAAGGGACAGCTAAAAACTGGGAAACCATGACAAT 4380
ATTGGAACATTTTATGCTACCTACAGTAGTAAACAAGTAGAGTGATTATGTAACATGACC 4440
TCAAGGCTGACACAAAAAAAAAAAAAAAAA                                4471
```

FIG. 10A

```
rabbit PAK I    MSdNG.ELED  KPPAPPvRMs  STifstGgKD  PLSANHSLKP  LPSVPEEKKP   49
human PAK2      MSdNG.ELED  KPPAPPvRMs  STifstGgKD  PLSANHSLKP  LPSVPEEKKP   49
human PAK65     .......MEE  tqqksnLeL.  ..........  .LSANHSLKP  LPSVPEEKKP   31
human PAK1      MSnNGlDiqD  KPPAPPMRnt  STmigvGsKD  agtlNHgsKP  LPpnPEEKKk   50
rat PAK65       MSnNGlDvqD  KPPAPPMRnt  STmigaGsKD  PgtlNHgsKP  LPpnPEEKKk   50
Consensus       MS-NG--LED  KPPAPPMRM-  ST----G-KD  PLSANHSLKP  LPSVPEEKKP rabbit PAK I    RnKIISIFSG  TEKGSKKKEK  ERPEISPPSD  FEHTIHVGFD  AVTGEFTGMP   99
human PAK2      RhKIISIFSG  TEKGSKKKEK  ERPEISPPSD  FEHTIHVGFD  AVTGEFTGMP   99
human PAK65     RhKIISIFSG  TEKGSKKKEK  ERPEISPPSD  FEHTIHVGFD  tVTGEFTGMP   81
human PAK1      kdrfyrsilp  gDKtnKKKEK  ERPEISlPSD  FEHTIHVGFD  AVTGEFTGMP  100
rat PAK65       kdrfyrsila  gDKtnKKKEK  ERhEISlPSD  FEHTIHVGFD  AcTGEFTGMP  100
yeast STE20                             ...rIStPyn  akHIhHVGvD  skTGEyTGlP  362
Consensus       R-KIISIFSG  TEKGSKKKEK  ERPEISPPSD  FEHTIHVGFD  AVTGEFTGMP rabbit PAK I    EQWARLLQTS  NITKLEQKKN  PQAVLDVLKF  YDSNTV..KQ  KYLSFTPPEK  147
human PAK2      EQWARLLQTS  NITKLEQKKN  PQAVLDVLKF  YDSNTV..KQ  KYLSFTPPEK  147
human PAK65     EQWARLLQTS  NITKLEQKKN  PQAVLDVLKF  YDSNTV..KQ  KYLSFTPPEK  129
human PAK1      EQWARLLQTS  NITKsEQKKN  PQAVLDVLeF  YnSkktsnsQ  KYMSFTdksa  150
rat PAK65       EQWARLLQTS  NITKsEQKKN  PQAVLDVLeF  YnSkktsnsQ  KYMSFTdksa  150
yeast STE20     EeWekLLt...                                                 370
Consensus       EQWARLLQTS  NITKLEQKKN  PQAVLDVLKF  YDSNTV--KQ  KYLSFTPPEK rabbit PAK I    DGFPSGaPAL  NtKVSETsAV  VT....EEDD  DDEEaAPPVI  APRPDHTKSI  193
human PAK2      DGLPSGtPAL  NaKgtEaPAV  VT....EEED  DDEETAPPVI  APRPDHTKSI  193
human PAK65     DGFPSGtPAL  NaKgtEaPAV  VT....EEED  DDEETAPPVI  APRPDHTKSI  175
human PAK1      EdYnSsnaln  vkaVSETPAV  ppvsedEDDD  DDDaTpPPVI  APRPEHTKSV  200
rat PAK65       EdYnSsntln  vktVSETPAV  ppvsedE.DD  DDDaTpPPVI  APRPEHTKSV  199
Consensus       DG-PSG-PAL  N-KVSETPAV  VT----EEDD  DDEETAPPVI  APRPDHTKSI rabbit PAK I    YTRSVIDPIP  AP....VGDS  HV........  ..DsgAKSsD  KQKKKtKMTD  229
human PAK2      YTRSVIDPVP  AP....VGDS  HV........  ..DgaAKSlD  KQKKKPKMTD  229
human PAK65     YTRSVIDPVP  AP....VGDS  HV........  ..DgaAKSlD  KQKKKtKMTD  211
human PAK1      YTRSVIEPlP  vtptrdVatS  pIsptenntt  ppDaltrntE  KQKKKPKMsD  250
rat PAK65       YTRSVIEPlP  vtptrdVatS  pIsptenntt  ppDaltrntE  KQKKKPKMsD  249
Consensus       YTRSVIDPVP  AP----VGDS  HV--------  --D--AKS-D  KQKKKPKMTD rabbit PAK I    EEIMEKLRTI  VSIGDPKKKY  TRYEKIGQGA  SGTVFTATDV  AlGQEVAIKQ  279
human PAK2      EEIMEKLRTI  VSIGDPKKKY  TRYEKIGQGA  SGTVFTATDV  AlGQEVAIKQ  279
human PAK65     EEIMEKLRTI  VSIGDPKKKY  TRYEKIGQGA  SGTVFTATDV  AiGQEVAIKQ  261
human PAK1      EEILEKLRsI  VSVGDPKKKY  TRFEKIGQGA  SGTVYTAmDV  AtGQEVAIKQ  300
rat PAK65       EEILEKLRnI  VSVGDPKKKY  TRFEKIGQGA  SGTVYTAmDV  AtGQEVAIKQ  299
yeast STE20                             ...tKY  anLvKIGQGA  SGvVYTAyEI  gtnvsVAIKQ  650
Consensus       EEIMEKLRTI  VSIGDPKKKY  TRYEKIGQGA  SGTV-TATDV  A-GQEVAIKQ
                                                                        I      II
```

FIG. 10B

```
rabbit PAK I   iNLQKQPKKE LIINEILVMK ELKNPNIVNF LDSYLVGDEL FVVMEYLAGG 329
human PAK2     iNLQKQPKKE LIINEILVMK ELKNPNIVNF LDSYLVGDEL FVVMEYLAGG 329
human PAK65    iNLQKQPKKE LIINEILVMK ELKNPNIVNF LDSYLVGDEL FVVMEYLAGr 311
human PAK1     mNLQqQPKKE LIINEILVMr EnKNPNIVNY LDSYLVGDEL WVVMEYLAGG 350
rat PAK65      mNLQqQPKKE LIINEILVMr EnKNPNIVNY LDSYLVGDEL WVVMEYLAGG 349
yeast STE20    mNLeKQPKKE LIINEILVMK gsKhPNIVNF iDSYvlkgDL WVIMEYMeGG 700
Consensus      -NLQKQPKKE LIINEILVMK ELKNPNIVNF LDSYLVGDEL -VVMEYLAGG
                          III        IV                  V rabbit PAK I   SLTDVVTET. CMDEaQIAAV CRECLQALEF LHaNQVIHRD IKSDNVLLGM 378
human PAK2     SLTDVVTETa CMDEaQIAAV CRECLQALEF LHaNQVIHRD IKSDNVLlGM 379
human PAK65    SLTDVVTET. CMDEaQIAAV CRECLQALEF LHaNQVIHRD IKSDNVLLGM 360
human PAK1     SLTDVVTET. CMDEgQIAAV CRECLQALEF LHsNQVIHRD IKSDNILLGM 399
rat PAK 65     SLTDVVTET. CMDEgQIAAV CRECLQALEF LHsNQVIHRD IKSDNILLGM 398
yeast STE20    SLTDVVThc. iLtEgQIgAV CREtLsgLEF LHskgVlHRD IKSDNILLsM 749
Consensus      SLTDVVTET- CMDE-QIAAV CRECLQALEF LH-NQVIHRD IKSDN-LLGM
                                                          VI rabbit PAK I   EGSVKLTDFG FCAQITPEQS KRSTMVGTPY WMAPEVVTRK AYGPKVDIWS 428
human PAK2     EGSVKLTDFG FCAQITPEQS KRSTMVGTPY WMAPEVVTRK AYGPKVDIWS 429
human PAK65    EGSVKLTDFG FCAQITPEQS KRSTMVGTPY WMAPEVVTRK AYGPKVDIWS 410
human PAK1     dGSVKLTDFG FCAQITPEQS KRSTMVGTPY WMAPEVVTRK AYGPKVDIWS 449
rat PAK65      dGSVKLTDFG FCAQITPEQS KRSTMVGTPY WMAPEVVTRK AYGPKVDIWS 448
yeast STE20    EGdIKLTDFG FCAQInelnl KRtTMVGTPY WMAPEVVsRK eYGPKVDIWS 799
Consensus      EGSVKLTDFG FCAQITPEQS KRSTMVGTPY WMAPEVVTRK AYGPKVDIWS
                          VII                  VIII rabbit PAK I   LGIMAIEMVE GEPPYLNENP LRALYLIATN GTPELQNPEK LSPIFRDFLN 478
human PAK2     LGIMAIEMVE GEPPYLNENP LRALYLIATN GTPELQNPEK LSPIFRDFLN 479
human PAK65    LGIMAIEMVE GEPPYLNENP LRALYLIATN GTPELQNPEK LSPIFRDFLN 460
human PAK1     LGIMAIEMIE GEPPYLNENP LRALYLIATN GTPELQNPEK LSaIFRDFLN 499
rat PAK65      LGIMAIEMIE GEPPYLNENP LRALYLIATN GTPELQNPEK LSaIFRDFLN 498
yeast STE20    LGIMiIEMIE GEPPYLNEtP LRALYLIATN GTPkLkePEn LSssLkkFLd 849
Consensus      LGIMAIEM-E GEPPYLNENP LRALYLIATN GTPELQNPEK LSPIFRDFLN
               IX                    X rabbit PAK I   RCLEMDVEKR GSAKELLQHP FL.KlAKPLS SLTPLIMAAK EAMKSNR   524
human PAK2     RCLEMDVEKR GSAKELLQHP FL.KlAKPLS SLTPLIMAAK EAMKSNR   525
human PAK65    RCLEMDVEKR GSAKELLQHP FL.KlAKPLS SLTPLIMAAK EAMKSNR   506
human PAK1     RCLDMDVEKR GSAKELLQHq FL.KiAKPLS SLTPLIaAAK EAtKnNh   545
rat PAK65      RCLEMDVEKR GSAKELLQHq FL.KiAKPLS SLTPLIaAAK EAtKnNh   544
yeast STE20    WCLcvEpEdR aSAtELLhde YiteiAeanS SLaPLVklAr lkkvaen...896
Consensus      RCLEMDVEKR GSAKELLQHP FL-K-AKPLS SLTPLIMAAK EAMKSNR
               XI
```

COMPOSITIONS AND METHODS COMPRISING CYTOSTATIC PROTEIN KINASE

This invention was made with Government support under Grant No. GM26738, awarded by the National Institutes of Health. The Government has certain rights in this invention.

FIELD OF THE INVENTION

The present invention relates generally to the fields of biology and medicine. In particular, the present invention is directed to compositions and methods useful in suppressing cell division and cleavage.

BACKGROUND OF THE INVENTION

Mature oocytes of amphibians are arrested in meiotic metaphase II due to the action of a multicomponent cytostatic factor (CSF) {Masui, Y., Biochem. Cell Biol., 70:920–945 (1992); Sagata, N., et al., Nature (London); 342:512–518 (1989) and Shibuya, E. K., et al., Development, 106:799–808 (1989)}. CSF is part of a Ras-GTP signaling pathway which acts through a MAP kinase (MAPK) cascade {Daar, I., et al., Science, 253:74–76 (1991); Fukuda, M., et al., J. Biol. Chem., 269:33097–33101 (1994) and Pomerance, M., et al., J. Biol. Chem., 267:16155–16160 (1992)}. The arrest is released upon fertilization with the completion of meiosis, and the early embryo undergoes a series of rapid cleavages. A major component of CSF, the Mos protein kinase, is synthesized in abundance during oocyte maturation and activates MAPK via phosphorylation of MAPK kinase (MAPKK) {Sagata, N., et al., Nature (London), 342:512–518 (1989); Sagata, N., et al., Nature, 335:519–525 (1988); Posada, J., et al., Mol. Cell. Bio., 13:2546–2553 (1993); Haccard, O., et al., Science, 262:1262–1265 (1993); Matsuda, S., et al., J. Biol. Chem., 268:3277–3281 (1993) and Kosako, H., et al., J. Biol. Chem., 269:28354–28358 (1994)}. Mos, which appears to be germ-cell specific, is rapidly degraded following fertilization and is not observed in cleaving embryos {Sagata, N., et al., Nature, 335:519–525 (1988); Yew, N., et al., Nature (London), 355:649–652 (1991); Watanabe, N., et al., Nature, 352:247–248 (1991) and Watanabe, N., et al., Nature (London), 342:505–511 (1989)}. Upon fertilization, MAPK and MAPKK are inactivated and remain inactive until the later stages of embryonic development {Haccard, O., et al., Science, 262:1262–1265 (1993); Kosako, H., et al., J. Biol. Chem., 269:28354–28358 (1994) and Ferrell, J. E., et al., Mol. Cell. Biol., 11:1965–1971 (1991)}.

Maturation promoting factor (MPF), which is required for progression through the cell cycle, is stabilized by CSF {Sagata, N., et al., Nature 335:519–525 (1988) and Pickham, K. M., et al., Mol. Cell. Biol., 12:3192–3203 (1992)}. MPF consists of the cell division control 2 kinase (cdc2) and cyclin. MPF activity is high during metaphase II arrest; following fertilization, cdc2 is inactivated by cyclin degradation and cyclin is regenerated during each division cycle.

Protease activated kinase I (PAK I) is a unique multipotential serine/threonine protein kinase which has been found in an inactive form in all animals and tissues examined to date {Tahara, S. M., et al., J. Biol. Chem., 256:11558–11564 (1981); Tuazon, P. T., et al., Eur. J. Biochem., 129:205–209 (1982); Tuazon, P. T., et al., J. Biol. Chem., 259:541–546 (1984); Rooney, R. D. et al., FASEB J., 6:A1852 (1992); and Rooney, R. D., et al., FASEB J., 6:A1852 (1992)}. Studies with 3T3-L1 cells also led to the identification of an endogenously active form of the PAK I holoenzyme {Rooney, R. D., et al., FASEB J, 6:A1852 (1992)}.

To determine whether PAK I has a role in the regulation of the cell cycle and functions as a cytostatic protein kinase, the inactive holoenzyme and the proteolytically activated enzyme have been injected into one blastomere of 2-cell frog embryos {Rooney, R. D., et al., FASEB J., 7:A1213 (1993)}. Activated PAK I inhibited cleavage of the injected cell, while the noninjected cell continued dividing through late cleavage. Injection of the inactive holoenzyme or heat-treated PAK I has no effect on cell cleavage. The data suggests PAK I is a cytostatic protein kinase, involved in mediating inhibition of the cell cycle.

PAK I can be activated by limited proteolysis with trypsin or chymotrypsin {Tahara, S. M., et al., J. Biol. Chem., 256:11558–11564 (1981)} or a $Ca^{2+}$-stimulated protease {Tahara, S. M., et al., Eur. J. Biochem., 126:395–399 (1982)}, hence the initial nomenclature. The inactive holoenzyme has been identified and partially purified from rabbit reticulocytes {Tahara, S. M., et al., J. Biol. Chem., 256:11558–11564 (1981)} and skeletal muscle {Tuazon, P. T., et al., Eur. J. Biochem., 129:205–209 (1982)}, chicken gizzard {Tuazon, P. T., et al., J. Biol. Chem., 259:541–546 (1984)}, and 3T3-L1 cells {Rooney, R. D., et al., FASEB J., 6:A1852 (1992)}. PAK I from reticulocytes uses only ATP as a phosphoryl donor, with a $K_m$ apparent of 0.6 mM {Tahara, S. M., et al., J. Biol. Chem., 256:11558–11564 (1981)}. The enzyme requires sulfhydryl reducing agents to maintain activity. The optimal $Mg^{2+}$ concentration for mixed histone as substrate is 45 mM; with less complex substrates, the $Mg^{2+}$ optimum is 5–10 mM {Tahara, S. M., et al., Eur. J. Biochem., 126:395–399 (1982)}.

Following activation in vitro by limited proteolytic digestion, PAK I phosphorylates histones H2B and H4 {Tahara, S. M., et al., J. Biol. Chem., 256:11558–11564 (1981)}, myosin light chain from skeletal and smooth muscle {Tuazon, P. T., et al., Eur. J. Biochem., 129:205–209 (1982) and Tuazon, P. T., et al., J. Biol. Chem., 259:541–546 (1984)}, translational initiation factors eIF-3, eIF-4B, and eIF-4F {Tahara, S. M., et al., Eur. J. Biochem., 126:395–399 (1982) and Tuazon, P. T., et al., J. Biol. Chem., 264:2773–2777 (1989)}, and avian and Rous sarcoma virus nuclear capsid protein NC {Leis, J., et al., J. Biol. Chem., 259:7726–7732 (1984); Fu, X., et al., J. Biol. Chem., 260:9941–9947 (1985) and Fu, X., et al., J. Biol. Chem., 263:2134–2139 (1988)}. In myosin light chain from smooth muscle, PAK I phosphorylates the same site as the $Ca^{2+}$/calmodulin-dependent myosin light chain kinase {Tuazon, P. T., et al., J. BioL Chem., 259:541–546 (1984)}. Phosphorylation of PAK I stimulates the actin-activated Mg-ATPase activity of myosin to the same extent as that observed upon phosphorylation of actomyosin by the $Ca^{2+}$-dependent myosin light chain kinase. An alternative site is modified in myosin light chain from skeletal muscle {Tuazon, P. T., et al., Eur. J. Biochem., 129:205–209 (1982)}.

In the Rous sarcoma virion, NC is fully phosphorylated at serine 40 {Fu, X., et al., J Biol. Chem., 260:9941–9947 (1985)}; following dephosphorylation, serine 40 is specifically modified by PAK I {Leis, J., et al., J. Biol. Chem., 259:7726–7732 (1984)}. Phosphorylation enhances the affinity of NC for single-strand RNA up to 100-fold by altering the conformation, allowing basic residues N-terminal to serine 40 to interact with RNA {Fu, X., et al., J. Biol. Chem., 260:9941–9947 (1985)}. Data with site-specific mutants of serine 40 indicate this residue is the switch between tight and loose binding {Fu, X., et al., J. Biol. Chem., 263:2134–2139 (1988)}.

It is an object of the present invention to provide compositions comprising PAK I or active fragments thereof and methods for the use of such compositions.

SUMMARY OF THE INVETION

The present invention presents a unique class of physiological suppressors of cell division and cleavage. In particular, the present invention presents PAK I, a p21-activated protein kinase, formally designated protease activated protein kinase I (also abbreviated as "PAK I"), which has been purified to apparent homogeneity. PAK I has several phosphorylation states, and a molecular mass of about 58–60 kDa as determined by polyacrylamide gel electrophoresis. Inactive PAK I, denoted "p60", is activated when autophosphorylated (for example, by its binding to Cdc42), and denoted "p58". The present invention also presents an active proteolytic fragment of PAK I, a peptide denoted p37, which contains the catalytic domain of PAK I and a small portion of the regulatory domain. The purification, characterization, nucleotide and amino acid sequences of PAK I and p37 are also disclosed.

Another aspect of the invention discloses the cytostatic activity of PAK I and its fragments. Further disclosed are the uses of these proteins and peptides for diagnosing and treating diseases, especially for cancer.

BRIEF DESCRIPTION OF THE DRAWINGS

The invention may be better understood with reference to the accompanying drawings, in which:

FIG. 1 presents the cDNA and deduced amino acid sequences of PAK I. The N-terminal amino acid residue of the proteolytically activated p37 fragment of PAK I is shown to begin at residue 197 (first ↑), and end at residue 524, also shown is the start of the catalytic domain which begins at residue 247 (second ↑), and ends at residue 524. PAK I starts at nucleotide 1 and ends at nucleotide 4471. p37 starts at nucleotide 662 and ends at nucleotide 1645 (1648 if the termination codon is counted).

FIG. 3 presents autoradiograms correlating proteolytic activation of inactive PAK I with autophosphorylation.

Figure 2:
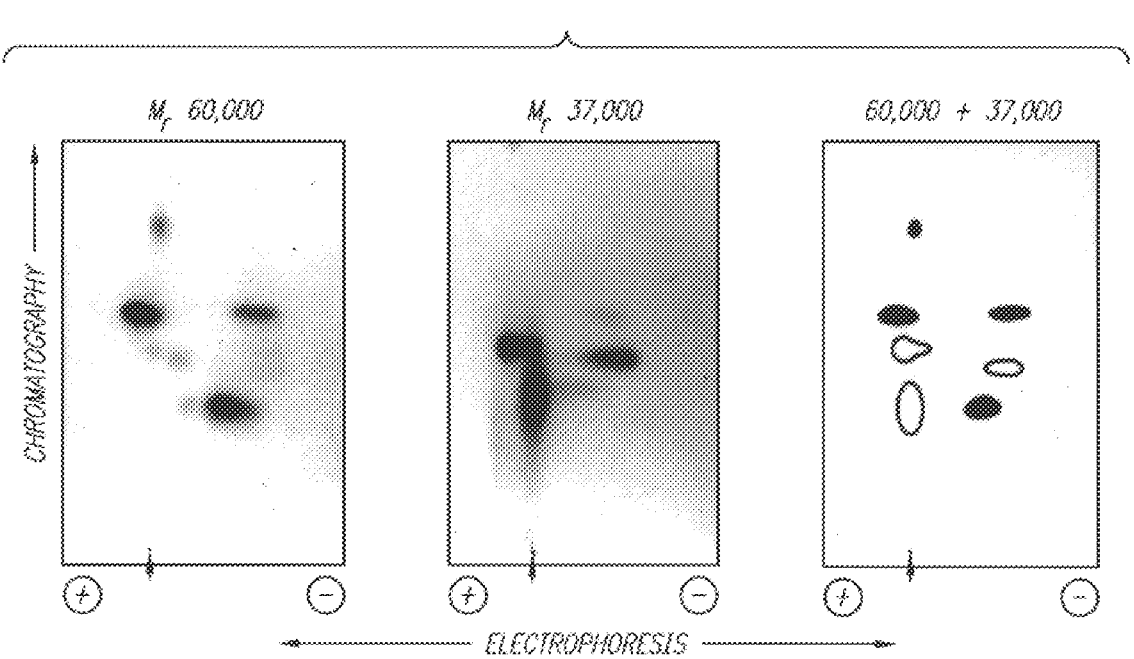
FIG. 2 presents the phosphopeptide maps of inactive PAK I and p37. Left panel, p60; middle panel, p37; right panel, schematic of p60 (open) and p37 (closed) chromatographed together.

Panel B presents the assay of the final step in the purification of the active catalytic fragment p37 by FPLC on Superose 12. Inset; Coomassie blue-stained gel of the fractions from Superose 12 containing PAK I activity.

Panel C presents Western blotting, to detect PAK I-like protein, with anti-PAK I antibody of the extracts containing equal amounts of protein from mature oocytes (lane 1); zygotes (lane 2); 2-cell embryos (lane 3); and 2-cell embryos injected with active PAK I (p58) and incubated for 10 min (lane 4).

FIG. 7 Panel A shows a frog embryo injected with active PAK I holoenzyme (4×10$^{-4}$ unit; 1 pg), then incubated at room temperature for an additional 150 min. The animal hemisphere is shown.

Panel B shows a view of the injected side of the embryo shown in panel A (rotation is 90° counter-clockwise).

Panel C shows a frog embryo injected with the PAK I catalytic fragment (p37) (4×10$^{-5}$ unit; 0.1 pg) and incubated for an additional 60 min.

Panel D shows a frog embryo injected with PAK I heat-treated at 75° C. for 15 min (4×10$^{-4}$ unit; 1 pg) and incubated for an additional 150 min.

Panel E shows DNA from a 2-cell embryo injected with PAK I catalytic fragment into both blastomeres, incubated for 30 min, then stained with fluorescent dye.

Panel F shows DNA from an uninjected control embryo developed to the 16-cell stage, and analyzed as in Panel E.

Figure 8:
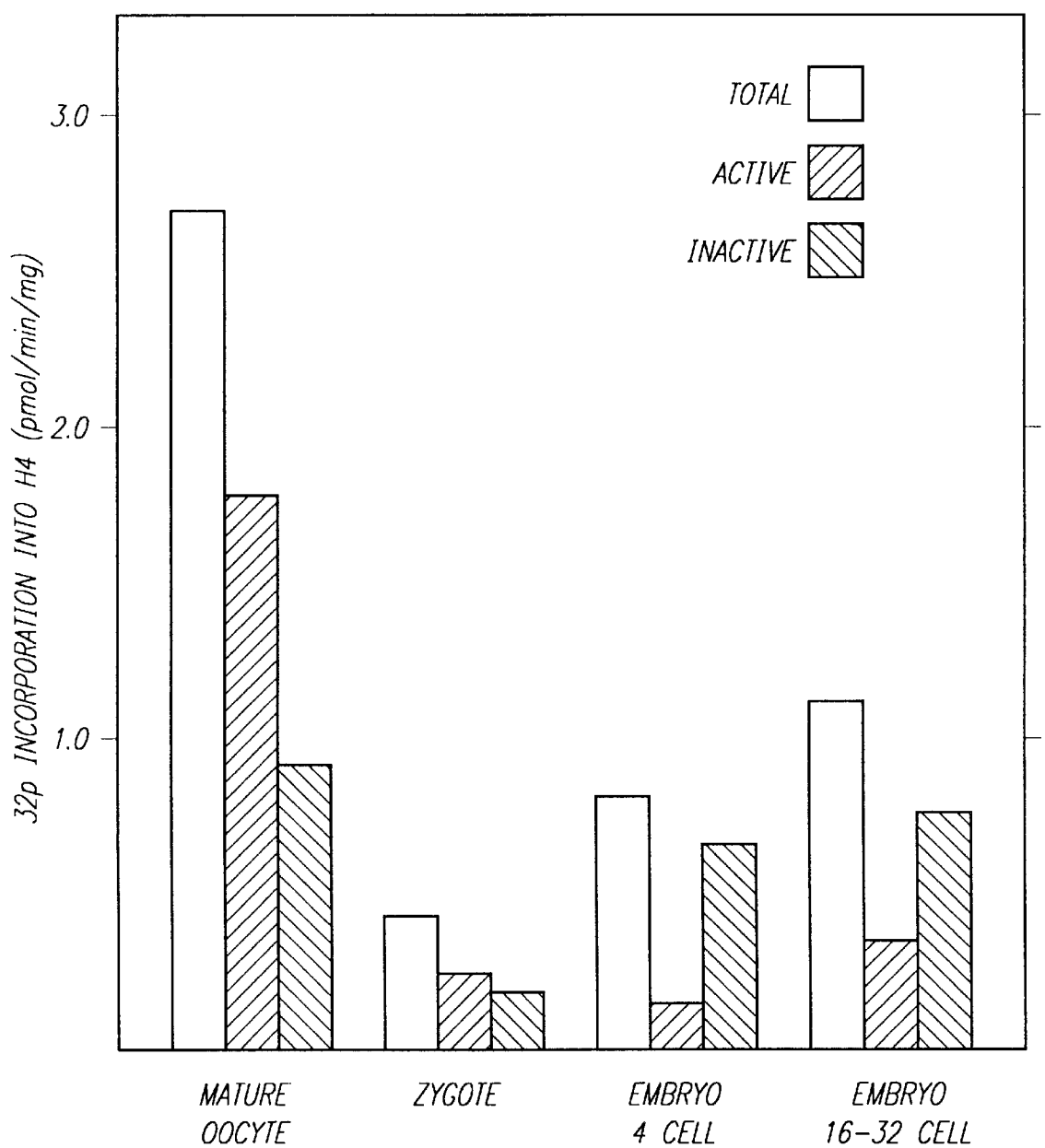

FIG. 8 quantifies the active and inactive forms of PAK I in frog eggs and embryos.

Figure 9:
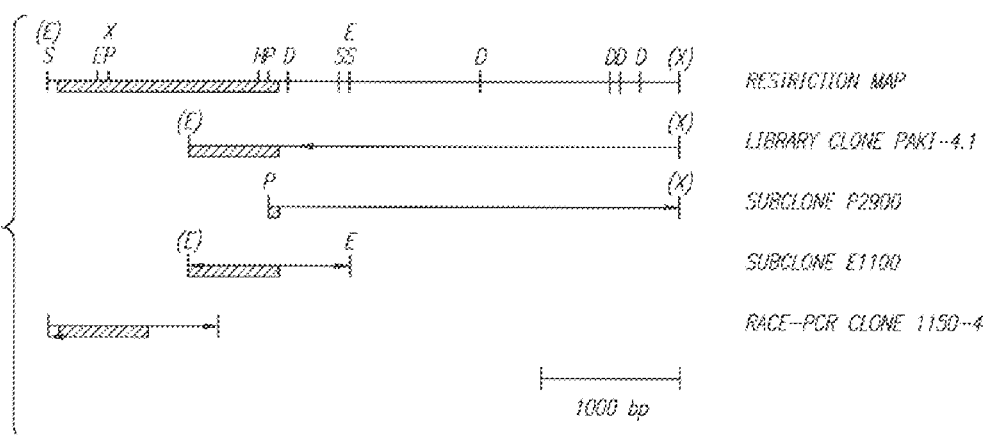

FIG. 9 schematically presents the strategy for cloning and sequencing of PAK I cDNA.

FIG. 10 presents multiple sequence alignment of p21-activated protein kinases.

Figure 11:
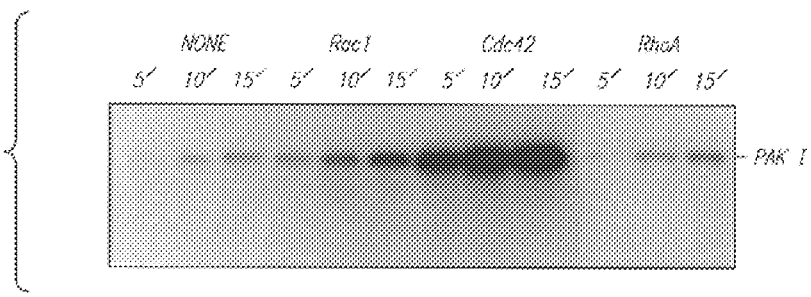

FIG. 11 presents autoradiogram showing the G protein (Cdc42) stimulated autophosphorylation of PAK I.

Figure 12:
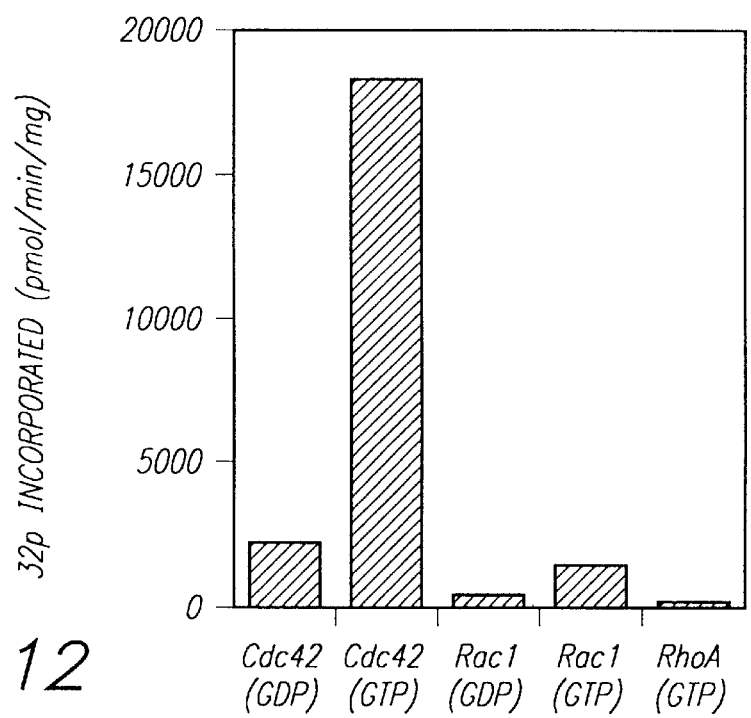

FIG. 12 presents the stimulation of PAK I activity by Cdc42.

DETAILED DESCRIPTION OF THE INVENTION

Pursuant to the present invention, PAK I has been purified to apparent homogeneity as an inactive monomer, p60, with a molecular mass of 60,000 as determined by polyacrylamide gel electrophoresis. The inactive holoenzyme is rapidly activated in vitro by the small G protein Cdc42 or by limited proteolysis with trypsin; with the latter, the time required for optimal activation is dependent on the concentrations of protein and trypsin. A peptide, p37, containing the active catalytic domain has a molecular weight of 37,000, as determined by polyacrylamide gel electrophoresis and gel filtration. No other major peptides are observed, indicating the regulatory domain is rapidly degraded.

With the inactive holoenzyme, only a small degree of autophosphorylation on serine is observed. When autophosphorylation is carried out following limited proteolysis, the catalytic peptide becomes highly autophosphorylated on serine and threonine. The appearance of this peptide and the extent of autophosphorylation of p37 are coincident with the increase in activity observed following proteolytic activation. The tryptic phosphopeptides from autophosphorylated inactive PAK I (p60) are different from the phosphopeptides autophosphorylated in the p37 catalytic fragment, as shown by two-dimensional phosphopeptide mapping. However, the phosphopeptides observed from p60 are a light background pattern in the phosphopeptide map from p37 and vice versa. All of the phosphopeptides observed in p60 and p37 are found in p60 when the holoenzyme is incubated with polylysine prior to autophosphorylation.

In accordance with one aspect of the present invention, the complete nucleotide and amino acid sequences for PAK I and p37 are provided. Unless otherwise modified, the term "protein" as used herein encompasses both native and synthetic polypeptides and peptides (including recombinant and chemically synthesized polypeptides and peptides). Unless otherwise indicated, "PAK I", "p60", "p58" and "p37" proteins include both their native and synthetic versions.

The nucleotide sequences contemplated for use in accordance with the present invention include, but are not limited to, the following: (1) the specific cDNA sequences for PAK I and p37 (FIG. 1 and SEQ ID NO: 1) as disclosed; (2) the complementary nucleotide sequences (which may be RNA or DNA) to the disclosed sequences; (3) the corresponding RNA sequences to the DNA sequences wherein the Thymidine ("T") in the disclosed DNA sequences is replaced with Uracil ("U"); (4) nucleotide sequences wherein other nucleotides known in the art such as nucleotide analogs, replace those in the foregoing sequences (for example, 5-methylcytosine replacing cytosine); (5) functionally equivalent nucleotide sequences that encode cytostatic proteins or peptides as contemplated herein and (6) nucleotide sequences with one or more mutations which enhance or diminish the catalytic activity. The above discussion would analogously apply to RNA sequences disclosed in this application.

Since nucleotide codons are redundant, also contemplated as within the scope of this invention are equivalent nucleotide sequences which include nucleotide sequences which code for the same or equivalent polypeptides. Thus, nucleotide sequences which encode substantially the same or functionally equivalent amino acid sequence may be used in the practice of the invention.

The determinative biological activity for an equivalent polypeptide in accordance with the present invention is the ability to suppress cell division and cleavage.

Within the definition of PAK I, p58, p60, and p37 proteins are cytostatic protein kinases derived from different organisms, but having the characteristics of PAK I discussed herein. The polypeptide sequences reported herein for PAK I and p37 (FIG. 1 and SEQ ID NO: 2), as well as functionally-equivalent variants thereof (e.g., mutations, insertions and deletions) which retain the ability to suppress cell division and cleavage, are clearly contemplated as within the scope of the present invention. These proteins are preferably also activated by autophosphorylation after limited proteolysis, or binding of Cdc42. The terms include protein kinases which are cytostatic, for more than one type of cell in an organism. These proteins are obtainable by various methods, including the purification method as described herein.

The polypeptides provided in accordance with the present invention may be fused to other proteins. For example, signal sequence fusions may be employed in order to more expeditiously direct the secretion of the protein. The heterologous signal replaces the native signal, and when the resulting fusion is recognized, i.e. processed and cleaved by the host cell, the PAK I protein is secreted. Signals are selected based on the intended host cell, and may include bacterial, yeast, insect, mammalian, and viral sequences. For example, the native signal of the herpes gD glycoprotein signal is suitable for use in mammalian expression systems. In addition, the polypeptides of the present invention may be fused to other peptide sequences which may, for example, be useful in delivering the polypeptides of the invention to particular target cells.

With respect to the role of PAK I in maintaining cells in a non-dividing state, PAK I is not like any of the previously described protein kinases currently known to be involved in cell cycle regulation. PAK I is apparently functioning to maintain a variety of cell types in stasis.

In accordance with one aspect of the present invention, the inactive holoenzyme of PAK I was purified to apparent homogeneity from rabbit reticulocytes. A composition consisting essentially of PAK I at this or higher purity constitutes a substantially pure composition of PAK I. The inactive holoenzyme, p60, migrates as a monomer of about 70,000 daltons upon gel filtration, with a molecular mass of about 60,000 Da as determined by polyacrylamide gel electrophoresis. The protein kinase is readily activated in vitro by limited proteolysis with trypsin, producing a peptide of 37,000 daltons which contains the catalytic domain. PAK I is dependent on sulfhydryl reducing agents for activity and removal of reducing agent or addition of N-ethylmaleimide results in loss of activity. With purified inactive PAK I p60, a low level of autophosphorylation is observed. Following proteolytic activation, the p37 peptide containing the catalytic domain and a small region of the regulatory domain becomes highly autophosphorylated. Autophosphorylation of the p37 peptide results in a 3-fold stimulation of protein kinase activity over that observed with the nonphosphorylated peptide, and a 30-fold stimulation over the inactive holoenzyme. The increase in activity upon proteolysis is due to a decrease in $K_m$ for the protein substrate; the increased activity observed following autophosphorylation of the p37 catalytic domain is due to stimulation of $V_{max}$.

Inactive PAK I is activated by the small G or GTPase protein Cdc42HS, also known as G25K, ("Cdc42HS" denotes Cdc42 of homo sapien) {Munemitsu, S., et al., *Mol. Cell. Biol.*, 10:5977–5982 (1990) and Shinjo, K, et al., *PNAS* (USA), 87:9853–9857 (1990)}. Binding of the GTP-bound form of Cdc42HS induces autophosphorylation of PAK I, resulting in activation of the protein kinase (see EXAMPLE 3, below).

PAK I is a potent cytostatic protein kinase which is involved in maintaining cells in a non-dividing state. To examine whether PAK I had cytostatic properties, active and inactive forms of PAK I (58–60 kDa) were purified from rabbit reticulocytes. In addition, the active catalytic domain was generated from inactive PAK I by limited proteolysis. Antibody prepared to PAK I from rabbit reacted with mammalian PAK I (from rabbit reticulocytes and mouse 3T3-L1 cells) as well as PAK I in mature frog oocytes. In studies with frog eggs, the PAK I protein was greatly reduced following fertilization in 2-cell embryos, as shown by immunoblot analysis. Injection of subfemtomole amounts of active PAK I or the active catalytic fragment (37 kDa, ie. p37) into one blastomere of 2-cell frog embryos resulted in cleavage arrest in the injected cell at metaphase, while the uninjected blastomere progressed through mid to late cleavage. Injection of inactive PAK I had no effect on cleavage. Three other protein kinases (the catalytic subunit of cAMP-dependent protein kinase, protein kinase C and casein kinase II), administered at the same concentrations as PAK I, had no effect on cleavage.

PAK I is highly active in mature oocytes, but the protein kinase activity is greatly reduced following fertilization and prior to initiation of cleavage. Thus, PAK I is apparently involved in maintaining the eggs in a non-dividing state. This cytostatic protein kinase is regulated both by changes in levels of PAK I protein and by altering between active and inactive forms of the enzyme. To investigate the role of PAK I in early embryo development and cleavage arrest, PAK I was analyzed in mature frog oocytes, zygotes, and embryos at the 4- and 16- to 32-cell stage. The active and inactive forms of PAK I were analyzed following chromatography on DEAE-cellulose and the protein was detected with antibody prepared to purified PAK I from rabbit. A high level of endogenous PAK I activity and protein of 58–60 kDa, which coincided with PAK I, were observed in mature oocytes. The levels of both PAK I activity and protein dropped dramatically after fertilization. At the 4- and 16- to 32-cell stages, the amount of protein increased, but the inactive form of the PAK I was predominant and activity remained low. In comparison, the activity of MAP (microtubule-associated or mitogen-activated protein) kinase and cdc2 (cell division control kinase 2) decreased dramatically after fertilization and remained low, while casein kinase II activity was essentially unchanged.

In mouse 3T3-L1 cells, PAK I is highly active under conditions of serum starvation or quiescence. In actively dividing cells PAK I activity is reduced, and both PAK I activity and protein are greatly reduced following addition of insulin to serum-starved cells (EXAMPLE 2). This is consistent with the data obtained with frog eggs that PAK I is involved in maintaining cell stasis.

Using the antibodies to PAK I disclosed herein, PAK I may be purified from e.g., a biological sample, using methods known in the art. In the preferred embodiment, PAK I may generally be purified from a biological sample by means of successive chromatographic steps. For example, in a preferred method for purifying the cytostatic protein kinase from a cell, the steps comprise the following:

(a) obtaining postribosomal supernatant from the cell;

(b) performing ion exchange chromatography of the supernatant on an anionic exchange resin and detecting and collecting fractions, collectively denoted first eluted fraction, which exhibit PAK I protein kinase activity;

(c) performing ion exchange chromatography of the first eluted fraction on cationic exchange resin and detecting and collecting a second eluted fraction which exhibits protein kinase activity;

(d) performing affinity chromatography of the second eluted fraction and detecting and collecting a third eluted fraction which exhibits protein kinase activity;

(e) performing a fast paced liquid chromatography of the third eluted fraction on an anionic exchange fast paced liquid chromatography (FPLC) resin and collecting a fourth eluted fraction which exhibits protein kinase activity; and (f) performing FPLC on the fourth eluted fraction on a cationic exchange FPLC resin and collecting a fifth eluted fraction which exhibits protein kinase activity, said fifth eluted fraction contains substantially pure PAK I. Assays known in the art may be used to detect the protein kinase activity in all the above fractions.

The following examples further detail the extraction, purification, and characterization of PAK I and p37, and their respective amino acid and nucleic acid sequences. To obtain DNA encoding the proteins disclosed herein, one may conduct hybridization screening with labelled PAK I or p37 oligonucleotides (usually, greater than about 20 nucleotides) to detect clones which contain homologous sequences in the cDNA libraries derived from cells or tissues of a particular animal, followed by analyzing the clones by restriction enzyme analysis and nucleic acid sequencing to identify full-length clones (see EXAMPLE 3, below). As examples of the current state of the art relating to molecular cloning and sequencing, one is directed to Sambrook, et al., *Molecular Cloning—A Laboratory Manual*, Cold Spring Harbor Laboratory (1989), and Horvath, et al., "An Automated DNA Synthesizer Employing Deoxynucleoside 3'-Phosphoramidites", *Methods in Enzymology*, 154:313–326 (1987), the entire disclosures of which are hereby incorporated by reference.

Uses of PAK I and Its Fragments

Due to their ability to arrest the cell cycle in rapidly dividing cells, endogenously active PAK I, the active catalytic domain p37, and fragments thereof which retain cytostatic ability (herein also collectively referred to as "cytostatic protein kinases") are useful to suppress cell divisions, especially as therapeutic agents for treatment in diseases, such as cancer, which are due to uncontrolled cell divisions. Examples of the cytostatic protein kinases are: the rabbit, frog, and 3T3-L1 PAK I and rabbit p37 disclosed herein, human PAK2, human PAK65, human PAK1, rat PAK65, yeast STE20, yeast SHK1, yeast PAK1Sp, mouse PAK3, the active catalytic domains of the foregoing, and fragments of the foregoing which retain cytostatic ability. Human PAK2, human PAK65, human PAK1, rat PAK65, yeast STE20, yeast SHK1, yeast PAK1Sp and mouse PAK3 are discussed in EXAMPLE 3, below. As far as applicants are aware, applicants are the first to show cytostatic activity for a member of the PAK I family, specifically for rabbit PAK I and p37, and to predict similar cytostatic activity for the other members of the PAK I family and related proteins which are highly homologous to and share certain characteristics with rabbit PAK I and p37, most notably in their protein kinase activities which may be activated by protease. For cytostatic purposes, p37 and nucleotide sequences encoding it are preferred. However, also preferred are constitutively activated mutants (including proteins and nucleotide sequences, such as DNA and mRNA) of PAK I. If unmutated PAK I is used, it may be activated by the additional administration of a constitutively activated mutant of Cdc42 or other activating agents. These cytostatic protein kinases may be administered alone or in combination. One or more forms of the cytostatic protein kinases can be dispersed in a physiologically acceptable carrier to form a cytostatic composition. Examples of physiologically acceptable carriers include: normal saline, PBS, and Ringer's solution.

The cytostatic protein kinase or nucleotide sequences encoding them, including mRNA, may be administered into cells via microspheres, liposomes, other microparticulate delivery systems or sustained release formulations placed in proximity with cancer sites. The cytostatic protein kinases and nucleotide sequences encoding them may be formulated and delivered using methods known in the art, such as those used for formulating and delivery of commercially available anticancer drugs. The formulation may be liposomal or polymer-based, similar to those currently in use for small cytotoxic agents such as doxorubicin, amphotericin, and cytosine arabinoside. The formulations and delivery methods (either systemic or local) may also be similar to those currently used for formulating and delivering proteins which are therapeutically active, such as for growth factors, proteases (e.g., tissue plasminogen activator) and DNAse (e.g., Pulmozyme, available from Genentech, South San Francisco, Calif.).

Alternatively, gene therapy utilizing the nucleotide sequences of the present invention may be used. The gene therapy may be achieved by the uptake of extrachromosomal elements or plasmids into a target cell, or by integration of the nucleotide sequence into the genome of the target cell. The nucleotide sequence may encode one or more of the cytostatic protein kinases and may be in the form of a plasmid or linear DNA. mRNA which will be translated in vivo into cytostatic protein kinases may also be used. Once the nucleotide sequence enters the target cell, it will then express the proteins. The nucleotide sequences are preferably isolated or in substantially pure composition, and may be directly administered or incorporated into a plasmid or viral vector and administered into an individual. The nucleotide sequences may be mixed with a pharmaceutically acceptable carrier prior to administration. The administrations may be by means of microinjection or particle bombardment using methods known in the art. For example, the injection may be by means of a gene gun, such as described in Yang, N. -S., et al. {*Gene Therapy via Particle Bombardment: Applications of the Accell Gene Gun*, in *Gene Therapeutics: Methods and Applications of Direct Gene Transfer*, Wolff, J. A., ed., Birkhauser, USA (1994)}. The nucleotide sequences may also be delivered by means of viral delivery systems, such as by means of retroviral or adenoviral vectors, known in the art which are described in e.g., Yang, N. -S., et al., above.

In more detail, nucleotide sequences, such as DNA and RNA, of the present invention may be transferred in vivo using methods known in the art. For example, the direct in vivo gene transfer may be achieved with formulations of DNA encapsulated in liposomes, DNA entrapped in proteoliposomes containing viral envelope receptor proteins (e.g. using the method disclosed in Nicolau, C., et al. {*PNAS* (USA), 80:1068–1072 (1983)}, hereby incorporated by reference in its entirety), calcium phosphate-coprecipitated DNA (e.g., using the method disclosed in Benvenisty, N., et al. {*PNAS* (USA), 83:9551–9555 (1986)}, hereby incorporated by reference in its entirety), and DNA coupled to a polylysine-glycoprotein carrier complex (e.g., using the method disclosed in Wu, G. Y. {*J. Biol. Chem.*, 263:14621–14624 (1988)}, hereby incorporated by reference in its entirety). In vivo infection by cloned viral DNA sequences after direct intrahepatic injection with or without formation of calcium phosphate coprecipitated DNA may also be used (e.g., using the method disclosed in Seeger, C., et al. {*PNAS* (USA), 81:5849–5852 (1984)}, hereby incorporated by reference in its entirety).

mRNA sequences of the present invention may be transferred and translated in the target cells using cationic lipid vesicles e.g., using methods described in Felgner, P. L., and Ringold, G. M., {*Nature*, 337:387–388 (1989) and *Nature*, 349:351–352 (1991)}, hereby incorporated by reference in their entirety. Injection of pure RNA or DNA directly into the target tissues or cells may also be used, such as described in Wolff, J. A., et al., *Sci.*, 247:1465–1468 (1990), hereby incorporated by reference in its entirety.

Injection directly into the locus of rapidly-dividing cells (e.g. a tumor site) is the primary route presently contemplated for therapeutic administration of these cytostatic protein kinases. However, as in some cases the rapidly-dividing cells are located amongst normal cells that are not actively dividing, systemic delivery methods (particularly when the active agent is used in combination with one or more agents effective for targeting a particular site or sites, e.g., the agents specifically target or bind tumor cells as opposed to normal cells) may also be used to deliver the cytostatic protein kinases to the tumor site. Examples of such targeting agents are antibodies, such as those known in the art, which are specific or which preferentially bind to tumor-specific antigens on the surface of the cells {Schneider-Gaedicke, E., et al., *Eur. J. Cancer*, 31:1326–1330 (1995)}. Other targeting agents are single chain peptides. The cytostatic protein kinases can be coupled either directly or indirectly to the antibodies. One example of indirect coupling is by use of a spacer moiety. These spacer moieties, in turn, can be either insoluble or soluble {Diener, et al., *Science*, 231:148–150 (1986)} and can be selected to enable drug release from the antibody molecule at the target site. The definition of antibodies, the formulations, and delivery of antibodies are further described below.

Delivery of the protein kinase to the interior of cells may also be carried out with toxins, for example diphtheria toxin, which binds by its B fragment to cell surface receptors and then is able to translocate the toxic A fragment to the cytosol. Fusion of the cytostatic protein kinase or a peptide thereof to an inactive mutant A fragment would allow the protein kinase to be carried across the plasma membrane as a passenger protein. This would allow the protein kinase to enter the cell as an active cytostatic agent {Madshus, et al., *Infect. & Imm.*, 60:3296–3302 (1992); Wiedlocha, A., *Cell*, 76:1039–1051 (1994)}. Other toxins are being utilized as single-chain immunotoxins composed of the carcinoma-reactive antibody targeted to tumor cells and truncated toxin {Friedman, P. N., et al., *Cancer Res.*, 53:334–339 (1993); Pastan, I. H., et al., *PNAS* (USA), 92:2765–2769 (1995); Zangmeister-Wittke, U., et al., *Int. J. Cancer*, 54:1028–1035 (1993)}. The carcinoma-reactive antibody can also be fused with other proteins such as the cytostatic protein kinases.

Folic acid-protein conjugates may also be used to deliver the cytostatic protein kinases or nucleotide sequences encoding the enzymes into the target cells through receptor mediated endocytosis, since receptors for the vitamin folic acid are frequently overexpressed on cancer cells. Such delivery systems may be based on those described by Leamon and Low {*PNAS* (USA), 88:5572–5576 (1991); *Biochem. J.*, 291:855–860 (1993)} which describe, generally, the delivery of protein conjugated to folate, including toxins {(Leamon, et al., *J. Biol. Chem.*, 268:24847–24854 (1993)} to the inside of the cell.

Liposomes can encapsulate large quantities of drug molecules, proteins, and/or nucleotides either within their aqueous interiors or dissolved into lipid bilayers. When attached to the proper antibody or other type of ligand, liposomes can be targeted to specific cells. Lee and Low {*J. Biol. Chem.*, 269:3198–3204, (1994)} describe the delivery of liposomes conjugated to folate or to antibody to the folate receptor. Following binding, the cell-associated folate/polyethylene glycol/liposomes are internalized by endocytosis. This system is also useful with regard to delivery of nucleotides into cells {Wang, et al., *PNAS* (USA), 92:3318–3322 (1995)}. This can be accomplished with an expression vector or viral vector carrying the gene for the cytostatic protein kinases.

The dosage of cytostatic protein kinase and their nucleotide sequences administered for treatment of a particular condition in a particular patient may be determined empirically in a routine manner. As would be apparent to those working in the field, an appropriate dosage in any given case depends upon the properties of the formulation employed, such as its binding activity and in vivo plasma half-life, the concentration of cytostatic protein kinase or nucleotide sequences in the formulation, the administration route, the site and rate of administration, the clinical tolerance of the patient involved, the age and health of the patient, the pathological condition afflicting the patient and the like. The patient's condition may be monitored and the dosages varied accordingly.

The cytostatic protein kinase therapy may be used in combination with other forms of therapies, e.g. those routinely used for treatment of the disease. In the case of cancer, these treatments would include conventional chemotherapy, hormone therapy, radiotherapy, laser therapy or surgery. In addition, pursuant to a preferred embodiment of the present invention, endogenous PAK I in a patient may be activated to suppress division of the target cells. This can occur by G proteins, drugs specific for PAK I, or any upstream activator of PAK I, such as extracellular hormones or antibody or drugs activating a receptor specifically activating PAK I.

Assays for PAK I Protein, Nucleotide Sequence and Fragments Thereof

Antibodies to the cytostatic protein kinases, especially PAK I and p37, may be used to assay an individual's biological sample to determine whether the protein(s) are present, active, or activatable. The results of these assays may be used to devise a therapeutic regimen or for diagnosing cancer or diseases related to abnormal PAK I activities.

The antibodies can be polyclonal or monoclonal. Polyclonal antibodies can be produced according to methods known in the art, such as vaccinating an animal with PAK I or p37, collecting and purifying the animal's antisera directed against the PAK I or p37. Monospecific polyclonal antibodies can also be produced using methods known in the art. Antibody which consists essentially of pooled monoclonal antibodies with different epitopic specificities, as well as distinct monoclonal antibody preparations are also provided. Monoclonal antibodies are made from antigen containing fragments of the protein or from synthetic peptides of those fragments by methods well known in the art {Kohler, et al., *Nature*, 256:495 (1975); *Current Protocols in Molecular Biology*, Ausubel, et al., ed., (1989)}. The antibodies may also be recombinant monoclonal antibodies produced according to the methods disclosed in Reading, U.S. Pat. No. 4,474,893, or Cabilly et al., U.S. Pat. No. 4,816,567. The antibodies may also be chemically constructed according to the method disclosed in Segel, et al., U.S. Pat. No. 4,676,980.

The term antibody, or immunoglobulin, as used in this invention includes intact molecules as well as fragments thereof, such as Fab, F(ab')$_2$, Fv, and single chain antibody ("SCA") which are capable of binding an epitopic determinant on an PAK I or p37 protein. SCA is a genetically engineered fused single chain molecule containing the variable region of the light chain and the variable region of the heavy chain linked by a suitable polypeptide linker. Methods for making these fragments are known in the art, see e.g., Harlow and Lane, *Antibodies: A Laboratory Manual*, Cold Spring Harbor Laboratory, New York (1988).

Another aspect of the invention presents the uses of nucleotide sequences of the cytostatic protein kinases, their complementary sequences, or nucleotide sequences which are capable of hybridizing to the mRNA or DNA of the cytostatic protein kinases under stringent hybridization assay condition. These nucleotide sequences may be used to screen the nucleic acids of an individual, for mutation in the PAK I gene resulting in cancer, other disease states, and/or to determine whether specific disease states are correlated with specific mutations. These nucleotide sequences may also be used to determine whether sufficient levels of PAK I mRNA are produced and whether the mRNA is active in translation. Such determination would serve as diagnostics, e.g. for cancer. The result may also be used to devise a therapeutic regimen or for diagnosing cancer or diseases related to abnormal PAK I activities.

In the preferred embodiment of the invention, an antibody or nucleic acid probe specific for PAK I or p37, or specific for a tag attached to PAK I or p37 may be used to detect the presence of the respective PAK I or p37 protein (using antibody) or polynucleotide (using nucleic acid probe) in biological samples. Any specimen containing a detectable amount of the PAK I or p37 antigen or polynucleotide can be used. Preferred specimens of this invention are biological fluid and tissue samples. A preferred example of biological fluid samples is blood. Preferred examples of biological tissue samples include tissue samples from biopsies and tissue of endothelial origin.

The antibody and nucleic acid probes are generally detectably labeled, for example, with a radioisotope, a fluorescent compound, a bioluminescent compound, a chemiluminescent compound, a metal chelator or an enzyme. When proteins are to be detected, immunoassays and immunohistochemical assays may be used. A technique which may result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies. When a nucleic acid is to be detected, it may be necessary to amplify the nucleic acid prior to binding with a PAK I or p37 specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used. Those of ordinary skill in the art will know or will be able to ascertain, using routine experimentation, the suitable labels and assay formats to use.

Therapeutics Using Antibodies to Cytostatic Protein Kinases

In another embodiment of the present invention, the antibodies to cytostatic protein kinases may also be administered to an individual to inhibit or stimulate PAK I activity. They can be administered parenterally, by injection or by gradual perfusion over time. The antibodies can be administered intravenously, intraperitoneally, intramuscularly, subcutaneously, intracavity, or transdermally, alone or in combination with other therapeutic agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases, preferably isolated or substantially pure, and the like.

The therapeutic dosage for the antibodies may be determined in a similar manner as described above for the cytostatic protein kinases.

The invention may be better understood with reference to the accompanying examples, which are intended for purposes of illustration only and should not be construed as in any way limiting the scope of the invention as defined in the claims appended hereto.

EXAMPLES

The abbreviations used in the following Examples are as follows:

| | |
|---|---|
| cdc2 | cell division control kinase 2 |
| CNBr | cyanogen bromide |
| CSF | cytostatic factor |
| EGTA | [ethylene-bis(oxyethylene nitrilo)]tetraacetic acid |
| eIF | eukaryotic initiation factor |
| FPLC | fast paced liquid chromatography |
| GEF | guanine nucleotide exchange factor |
| GST | glutathione S-transferase |
| GTPγS | guanosine 5'-O-(3-thiotriphosphate) |
| JNK | c-Jun N-terminal kinase |
| MAP | microtubule-associated or mitogen-activated protein |
| MAPK | MAP kinase |
| MAPKK | MAPK kinase |
| MPF | maturation promoting factor |
| NEM | N-ethylmaleimide |
| PCR | polymerase chain reaction |
| PMSF | phenylmethylsulfonyl fluoride |
| RACE-PCR | rapid amplification of cDNA ends-PCR |
| RT-PCR | reverse transcription-PCR |
| SAPK | stress-activated protein kinase |

Example 1

Active and Inactive Forms of PAK I

In this study, the inactive holoenzyme and two endogenously active forms of PAK I have been purified from rabbit reticulocytes, partially characterized, and compared with regard to physical/chemical properties. Following limited tryptic digestion of inactive PAK I, a peptide of 37 kDa (p37) was shown to possess catalytic activity; autophosphorylation of p37 stimulated the catalytic activity further.

EXPERIMENTAL PROCEDURES

Materials—Histone IIAS, trypsin (L-1-tosylamido-2-phenylethyl chloro-methylketone-treated), soybean trypsin inhibitor, bovine serum albumin (fatty acid-free), and protamine-agarose (lot # 125F-9670), and phosphocellulose (lot # 81F-0108) were obtained from Sigma Chemical Company, St. Louis, Mo., USA. DEAE-cellulose (DE-52) was from Whatman Laboratory Products Inc., Clifton, N.J., USA. Superose 6 HR 10/30, Superose 12 HR 10/30, Mono Q HR 5/5 and Mono S HR 5/5 columns and SP-Sepharose fast flow were from Pharmacia Biotech Inc., Piscataway, N.J., USA. [γ-$^{32}$P]ATP was obtained from Amersham Corporation, Arlington Heights, Ill., USA. Histone H4 was from Boehringer Mannheim, Indianapolis, Ind., USA. Reticulocyte lysate was purchased from Green Hectacres, Oregon, Wis., USA; the protease inhibitor aprotinin was added to the fresh lysate.

Activation and Assay of PAK I—Standard activation conditions for PAK I during purification were carried out in 0.040 ml reactions containing 10 mM Tris-HCl (pH 8.0 at 30° C.), 5 mM 2-mercapoethanol, 100 μg bovine serum albumin, 0.010 ml aliquots of the column fractions, and 160 ng trypsin (from a stock solution of 0.04 mg/ml); incubation was for 3 min at 30° C. and proteolysis was terminated by addition of 1.6 μg of soybean trypsin inhibitor. PAK I was also incubated in the absence of trypsin. With highly purified PAK I, activation was conducted in the absence of bovine serum albumin, trypsin was reduced to 40–80 ng, and incubation was at 30° C. for 30–90 sec.

All forms of active PAK I were assayed in 0.070 ml reaction mixtures containing 50 mM Tris-HCl pH 7.4, 45 mM MgCl$_2$, 30 mM β-mercaptoethanol, 0.2 mM [γ-$^{32}$P]ATP (300 cpm/pmol) and 1 mg/ml histone IIAS. Incubation was at 30° C. for 15 min; the reaction was terminated by the addition of 0.010 ml of 100 mM ATP followed by precipitation with trichloroacetic acid {Hathaway, G. M., et al., Meth. Enzymol., 60:495–511 (1979)}. Samples (0.020 μl) were also assayed with 2 μg of H4; radiolabeled histone was analyzed by electrophoresis on 12% polyacrylamide gels containing sodium dodecyl sulfate. The protein was visualized by silver staining or staining with Coomassie blue. Protein standards included phosphorylase b (92,000), bovine serum albumin (68,000), creatine kinase (40,000), carbonic anhydrase (31,000), and soybean trypsin inhibitor (21,000). The extent of phosphorylation was monitored by autoradiography and/or by excising the radioactive histone band and counting in a scintillation counter {Hathaway, G. M., et al., Meth. Enymol., 60:495–511 (1979)}. All assays were kinetically valid and the data with H4 were comparable to that obtained with histone IIAS.

Autophosphorylation—Autophosphorylation of PAK I was carried out in a final volume of 0.100 ml containing 0.080 ml of enzyme, to which was added 10 mM MgCl$_2$, 30 mM 2-mercaptoethanol, and 0.2 mM [γ-$^{32}$P]ATP (specific activity, 1000–5000 cpm/pmol). After incubation at 30° C. for the indicated period of time, the reactions were terminated with 0.005 ml of 100 mM ATP and gel electrophoresis sample buffer. The samples were subjected to gel electrophoresis on 12.5% polyacrylamide gels as described above.

Purification of Inactive PAK I—Postribosomal supernate was obtained from rabbit reticulocytes as previously described {Traugh, J. A., et al., Meth. Enzymol., 60:534–541 (1979)}. Leupeptin (4 μg/ml), pepstatin (4 μg/ml), aprotinin (4 μg/ml), PMSF (0.5 mM), cAMP (10$^{-5}$ M), and sodium vanadate (1 mM) were added to 400–600 ml of supernate at the final concentrations indicated. The pH was adjusted to 7.8 by the addition of 1 N KOH and the conductivity of the supernate was reduced to approximately 1.8 mmho with cold distilled water. The supernate was batch-adsorbed to 450 g of DEAE-cellulose equilibrated in buffer A (20 mM Tris-HCl, pH 7.8 at 4° C., 1 mM EDTA, 1 mM EGTA, 3 mM dithiothreitol, 10$^{-5}$M cAMP, 1 mM sodium vanadate, and 0.02% sodium azide), as previously described {Tahara, S. M., et al., J. Biol. Chem., 256:11558–11564 (1981)}. After washing with 4 l of buffer A, the resin was packed into a column (6×50 cm) and washed with 3 to 4 l of buffer A. Protein was eluted with a 0–0.4 M KCl linear gradient in 3 l of buffer A. Fractions (20 ml) were collected and aliquots (0.010 ml) were assayed for protein kinase activity. When the initial volume of supernate was reduced to 100–150 ml, the volumes and columns at each step were decreased accordingly.

Fractions containing inactive PAK I (50 to 90 mM KCl) were pooled and treated with 0.1 mM PMSF. The sample was dialyzed overnight against 2 l of buffer B (buffer A minus cAMP) with one change and applied to a SP-Sepharose fast flow column (5×6 cm) equilibrated with buffer B. The column was washed with 500 ml of buffer A and the protein was eluted with a linear gradient from 0–0.6M NaCl in 1 l of buffer B; 10 ml fractions were collected. In some experiments, phosphocellulose was used instead of SP-Sepharose and developed with buffer B at pH 7.2.

After assaying for protein kinase activity, the fractions containing inactive PAK I from SP-Sepharose (100 to 150 mM NaCl) or phosphocellulose (200–250 mM NaCl), were pooled and treated with 0.1 mM PMSF. The pH was adjusted to 7.8 using 1M Tris, and the sample was diluted to a conductivity of 4 mmho with cold distilled water. The protein kinase was loaded onto a protamine-agarose column (1.5×6 cm) equilibrated with buffer C (20 mM Tris HCl, pH 7.8 at 4° C., 100 mM NaCl, 7.5 mM $MgCl_2$, 1 mM EDTA, 1 mM EGTA, 3 mM dithiothreitol, and 0.02% sodium azide) and washed with 10 column volumes of buffer C. The enzyme was eluted with a 400 ml gradient from 0.1–1.0M NaCl in buffer C; 5 ml fractions were collected and treated with 0.1 mM PMSF.

Further purification was carried out with aliquots of inactive PAK I using FPLC. An aliquot (8 ml) was dialyzed against buffer B containing 1 mM PMSF and loaded onto Mono Q HR5/5 column; the column was washed with 10 ml of buffer B and the protein was eluted in the same buffer with a 15 ml NaCl gradient from 0 to 0.5M. Fractions (0.5 ml) were collected and assayed. Three fractions containing the main portion of the activity from Mono Q were pooled, dialysed against buffer B, and loaded onto a Mono S column. The resin was washed with 10 ml of the same buffer and chromatographed in buffer B with a 12.5 ml NaCl gradient from 0 to 0.3M; 0.5 ml fractions were collected and assayed. Protein from the peak fractions was analyzed by polyacrylamide gel electrophoresis followed by staining with Coomassie blue or by silver staining. One unit of PAK I activity is defined as the amount of enzyme required for the incorporation of 1 pmol of phosphate into histone IIAS per min at 30° C. {Tahara, S. M., et al., *J. Biol. Chem.*, 256:11558–11564 (1981)}. Protein concentrations were determined by the method of Bradford {Bradford, M. M., *Anal. Biochem.*, 72:248–254 (1976)}.

The enzyme purified through protamine-agarose was stored for several months at 4° C. without significant loss of activity if supplemented every week with PMSF (0.1 mM) and every 2 weeks with dithiothreitol (1 to 2 mM). Enzyme activity after chromatography on Mono Q and Mono S was more labile, with a half-life of about 1 week.

Purification of Active PAK I—Purification of active PAK I was carried out as described for inactive PAK I. Active PAK I chromatographed at 100–150 mM KCl on DEAE-cellulose; in the following steps active and inactive PAK I were purified separately using the same procedures. Active PAK I eluted from SP-Sepharose at 200–250 mM NaCl. In the protamine-agarose step, a gradient of 0.1–1.2M NaCl in buffer C containing 1 mM sodium vanadate was used. Two forms of active PAK I eluted at 250 and 680 M NaCl and were identified as the A and B forms, respectively. Each form was purified further by HPLC on Mono Q and Mono S; 0 to 1.0M NaCl gradients in buffer B were utilized.

Gel filtration on Superose 12—Samples of active PAK I (0.500 ml) or inactive PAK I (0.200 ml) purified through Mono S were subjected to gel filtration on Superose 12 and Superose 6 columns, respectively, in buffer B containing 200 mM NaCl and 10% glycerol. Fractions of 0.25 ml were collected and assayed for protein kinase activity with H4.

Phosphopeptide mapping and phosphoamino acid analysis—Radioactive bands corresponding to inactive PAK I (p60) and the catalytic peptide (p37) were excised from the polyacrylamide gel and digested extensively with trypsin as described previously {Tuazon, P. T., et al., *J. Biol. Chem.*, 264:2773–2777 (1989)}. The phosphopeptides were analyzed by thin layer electrophoresis at 500 V for 5 h using acetic acid:pyridine:water (100:10:890) pH 3.5 as solvent, in the first dimension, and ascending chromatography using butanol:pyridine:acetic acid:water (60:40:12:48) in the second dimension. Radioactive phosphopeptides were detected by autoradiography.

For phosphoamino acid analysis, the radioactive protein bands were excised from the polyacrylamide gel, digested extensively with trypsin as described above, and hydrolyzed in 6N HCl at 110° C. for 3 h. The phosphoamino acids were analyzed as described previously {Tuazon, P. T., et al., *J. Biol. Chem.*, 264:2773–2777 (1989)}.

Western Blotting—Western blotting with antibody prepared to inactive PAK I was carried out as described in EXAMPLE 2, below; detection was by chemiluminescence.

Treatment of PAK I with NEM—Inactive PAK I and active PAK IA (0.8 unit; 15 $\mu$l) and B (0.2 unit, 15 $\mu$l) were preincubated with the indicated concentrations of N-ethylmaleimide (NEM) for 5 min at 30° C. in reaction volumes of 0.040 ml containing 11 mM 2-mercaptoethanol. Inactive PAK I (1.4 units, 0.010 ml) was activated in 40 $\mu$l reaction volumes with trypsin. Aliquots (0.004 ml) were incubated with the indicated concentrations of NEM in 0.040 ml reaction volumes containing 0.8 mM 2-mercaptoethanol. Activity assays were carried out with mixed histone as substrate.

In Situ Renaturation and Assay in Polyacrylamide Gels—Active and inactive forms of PAK were analyzed on two identical 12.5% polyacrylamide gels cast with 0.2 mg/ml mixed histone using the procedure described by Kameshita, I., et al., {*Anal. Biochem.*, 183:139–143 (1989)}. To assay for inactive PAK I, one gel was preincubated for 3 min in 5 ml of buffer A containing 4 $\mu$g/ml trypsin; proteolysis was terminated by the addition of soybean trypsin inhibitor to a final concentration of 40 $\mu$g/ml. The gels were incubated separately for 30 min in 5 ml of buffer B (50 mM Tris-HCl, pH 7.4, 45 mM $MgCl_2$, 30 mM 2-mercaptoethanol, 0.5 mM EGTA, and 40 $\mu$g/ml soybean trypsin inhibitor). The protein kinase assay was carried out in 1.5 ml of buffer B containing 0.2 mM [$\gamma$-$^{32}$P]ATP (specific activity, 2000 cpm/pmol) for 1 h at room temperature. The gels were washed repeatedly with gentle shaking in 5% trichloroacetic acid and 1% sodium pyrophosphate to remove the [$\gamma$-$^{32}$P]ATP, stained with Coomassie brilliant blue, destained, dried, and exposed to X-ray film.

RESULTS

Purification of Inactive PAK I—The inactive PAK I holoenzyme was purified to apparent homogeneity from the postribosomal supernate of rabbit reticulocytes in the presence of protease inhibitors. Activation of inactive PAK I was carried out by limited tryptic digestion prior to assay of the enzyme. In the initial chromatography step on DEAE-cellulose, inactive PAK I eluted between 50 and 90 mM KCl. Proteolysis resulted in a 10- to 12-fold increase in enzyme activity at this step of purification. These DEAE-cellulose fractions also contained casein kinase I and two other inactive protein kinases, PAK II and protein kinase C. On phosphocellulose or SP-Sepharose, all of these enzymes were separated from PAK I. On phosphocellulose, PAK I eluted at 200–250 mM NaCl; protein kinase C did not adhere to the resin, PAK II eluted at 300–350 mM NaCl and casein kinase I at 500 mM. A similar separation was obtained with SP-Sepharose with PAK I eluting at 100–150 mM NaCl.

Inactive PAK I was purified further by chromatography on protamine-agarose and eluted at 150 to 200 mM NaCl as a single symmetrical peak of activity. The enzyme activity was stimulated over 20-fold following limited trypsin digestion. Aliquots of PAK I (24,000 units) were purified to apparent homogeneity by FPLC on Mono Q, followed by Mono S. PAK I eluted from Mono Q at 250 mM NaCl and from Mono S at 130 mM NaCl. Pooled fractions from each chromatography step in the purification of PAK I were analyzed by polyacrylamide gel electrophoresis followed by staining with Coomassie blue. The amount of total protein analyzed from each step of purification was the following: DEAE-cellulose (70 µg); SP-Sepharose fast flow (21 µg); protamine-agarose (12 µg); Mono Q (1 µg); Mono S (0.5 µg). A single protein band of 60 kDa (p60) was observed after the final purification step. Since enzyme from the protamine agarose step was more stable than the purified enzyme, PAK I was stored at 4° C. as the partially purified enzyme after protamine-agarose and purified by FPLC as needed.

Purification of Active PAK I—During the initial chromatography step on DEAE-cellulose, active PAK I eluted between 100 and 160 mM KCl. When histone IIAS was used as substrate, both H2B and H4 were phosphorylated, as shown previously with the proteolytically activated enzyme {Tahara, S. M., et al., *J. Biol. Chem.*, 256:11558–11564 (1981)}. Similar results were obtained with H4 as substrate. H4 is not phosphorylated by any other major protein kinase and proved to be a specific substrate for PAK I. Active PAK I chromatographed on Fast S Sepharose eluted at 250 mM NaCl. When the pooled enzyme was chromatographed on protamine agarose, two peaks of activity were observed. The A form eluted around 250 mM NaCl and the B form around 680 mM NaCl. No inactive enzyme appeared to co-chromatograph with the active forms, since pretreatment by limited tryptic digestion diminished the activity slightly. Active PAK I was purified further by FPLC on Mono Q and Mono S. PAK IA eluted at 300 mM NaCl from Mono Q and 600 mM NaCl from Mono S, while PAK IB eluted at 350 and 650 mM NaCl from Mono Q and Mono S, respectively.

Physical/Chemical Analysis of Active and Inactive PAK I—Western blotting of the active and inactive forms of PAK I was carried out with antibody prepared to the inactive form. Anti-PAK I antibody detected two protein bands with inactive PAK I, a major band at 60 kDa and a second band at 58 kDa. With active PAK IA, the protein migrated at 58–60 kDa, but the majority of the protein was detected at 58 kDa. Active PAK IB migrated as a single protein band of 58–59 kDa. Thus, the two forms of endogenously active PAK I reacted specifically with antibody prepared to inactive PAK I.

The active and inactive forms were also analyzed following electrophoresis in polyacrylamide gels cast with mixed histone by in situ phosphorylation with [γ-$^{32}$P]ATP. Little phosphorylation of histone was observed with inactive PAK I; however, following limited tryptic digestion of inactive PAK I in situ, protein kinase activity was observed at 60 kDa. Active PAK IA and B migrated at 58 and 58–59 kDa, respectively; trypsin treatment in situ had little or no effect on activity. The differences in migration of the active and inactive forms of PAK I were due to changes in the phosphorylation state and not to proteolysis.

When reducing agents were removed from the holoenzyme by overnight dialysis, the activity was reduced to 6% of that of the nondialyzed enzyme. Upon addition of mercaptoethanol, the activity could be partially restored. The extent of loss of activity was dependent on the length of time the protein kinase was maintained in the absence of reducing agent. To examine the role of sulfhydryl groups in activity, active and inactive PAK I were examined after pretreatment with the oxidizing agent NEM. The activity was dependent on the concentration of NEM in the preincubation step; the assays were carried out in the presence of reducing agent. At 2 mM NEM, the activity of active PAK IA and B was reduced to 35% and 39% respectively. PAK I activated by trypsin was affected similarly; the activity was reduced to 45%.

Autophosphorylation of Inactive PAK I—Autophosphorylation was examined with inactive PAK I purified through the Mono S step to apparent homogeneity. When the holoenzyme was incubated with [γ-$^{32}$P]ATP, only a little autophosphorylation was observed. Upon activation by limited tryptic digestion, a relatively stable peptide of 37 kDa was observed. No other peptides were visible on the gel even at high levels of protein, indicating the remainder of the PAK I protein was readily cleaved. Following proteolytic activation and incubation of PAK I with radiolabeled ATP, the p37 peptide was highly autophosphorylated.

Phosphoamino acid analysis of autophosphorylated inactive PAK I showed only serine residues; approximately equal amounts of phosphoserine and phosphothreonine were observed in p37. Comparison of the tryptic peptides from the two samples by two-dimensional phosphopeptide mapping showed distinctly different phosphopeptide maps (FIG. 2). Autophosphorylation of inactive holoenzyme (p60) and proteolytically activated p37 (1–2 µg each) was carried out under standard conditions using [γ-$^{32}$P]ATP (5000 cpm/pmol). The proteins were resolved by gel electrophoresis, excised from the gel, digested extensively with trypsin, and the phosphopeptides mapped as described in Experimental Procedures. The autoradiograms are shown in FIG. 2: left panel, p60; middle panel, p37; right panel, schematic of p60 (open) and p37 (closed) chromatographed together. Four phosphopeptides were observed with p60 and three different phosphopeptides were associated with p37. When examined closely, a barely discernable background of phosphopeptides in p60 corresponded to the major phosphopeptides in p37 and vice versa. When the two samples were mixed prior to mapping, a total of seven phosphopeptides were obtained. This indicated the site(s) of autophosphorylation of the holoenzyme was different from the sites on p37 autophosphorylated after activation.

Figure 3A:
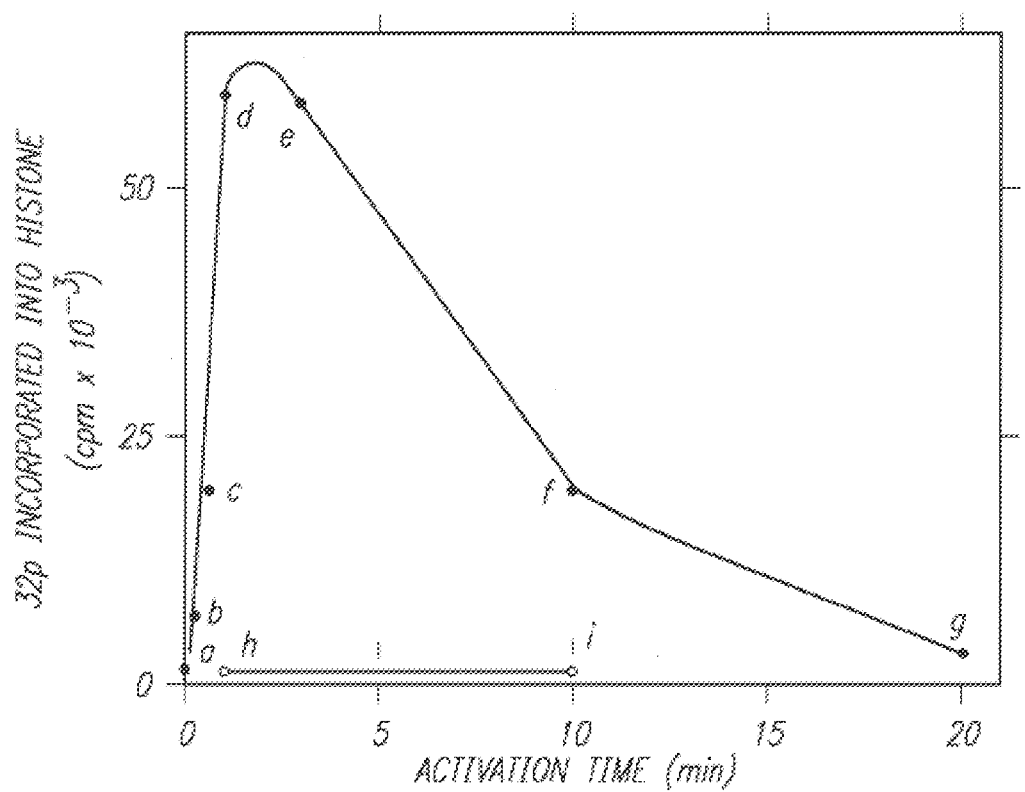
FIG. 3A—PAK I activity monitored in the standard assay with histone as substrate.
Figure 3B:
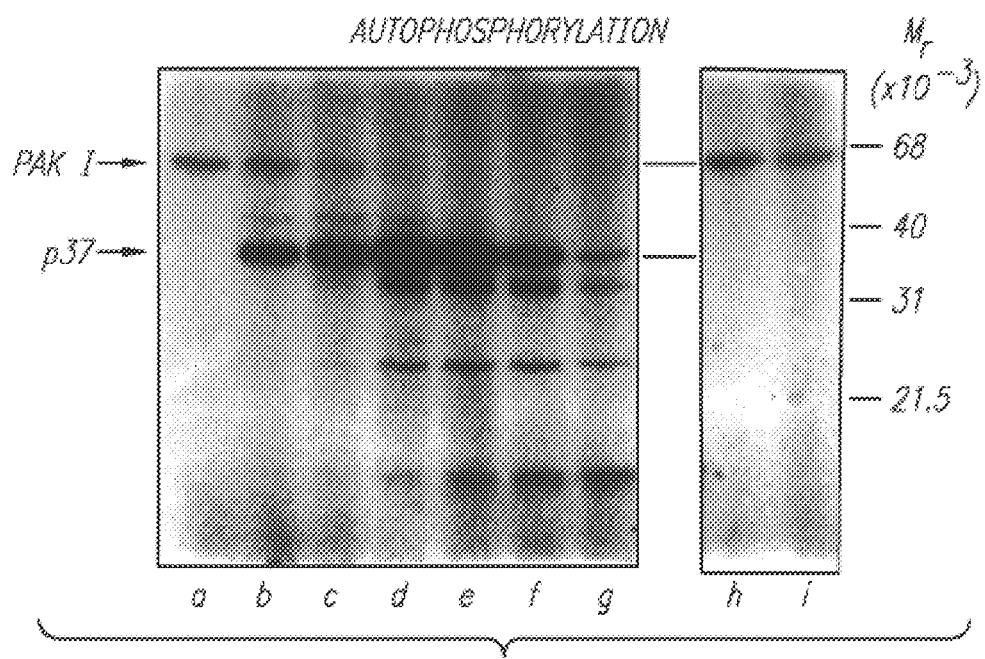
FIG. 3B—PAK I autophosphorylated with ($\gamma$-$^{32}$P)ATP and analyzed by gel electrophoresis followed by autoradiography. Closed symbols (a–g) represent trypsin-activated enzyme; nonactivated enzyme is represented by the open symbols (h,i).

The effects of limited proteolysis on enzyme activity and on autophosphorylation were examined with time. PAK I purified through protamine-agarose (21 µg) was incubated with 0.6 µg trypsin in the absence of bovine serum albumin in a 0.78 ml reaction mixture for up to 20 min. Aliquots (0.10 ml) were removed at the times indicated and soybean trypsin inhibitor was added. The autoradiograms are shown in FIG. 3: Left panel—PAK I activity monitored in the standard assay with histone as substrate; Right panel—PAK I autophosphorylated with (γ-$^{32}$P)ATP (1000 cpm/pmol) and analyzed by gel electrophoresis followed by autoradiography. Closed symbols (a–g) represent trypsin-activated enzyme; nonactivated enzyme is represented by the open symbols (h,i). As shown in FIG. 3, Left panel, activation of PAK I was maximal following treatment of the inactive holoenzyme with trypsin for 2 to 3 min. At 20 min, enzyme activity was reduced to 7%. No activity was detected when the holoenzyme was incubated in the absence of trypsin. When autophosphorylation was examined in the same experiment, radiolabel was associated only with PAK I p60 prior to tryptic digestion. When autophosphorylation was carried out after activation, the major phosphorylated product, p37, was observed after 15 sec of proteolysis and was maximal at 2 to 3 min (FIG. 3, Right panel). Phosphorylation of the p37 peptide coincided with activation of the enzyme.

Figure 4:
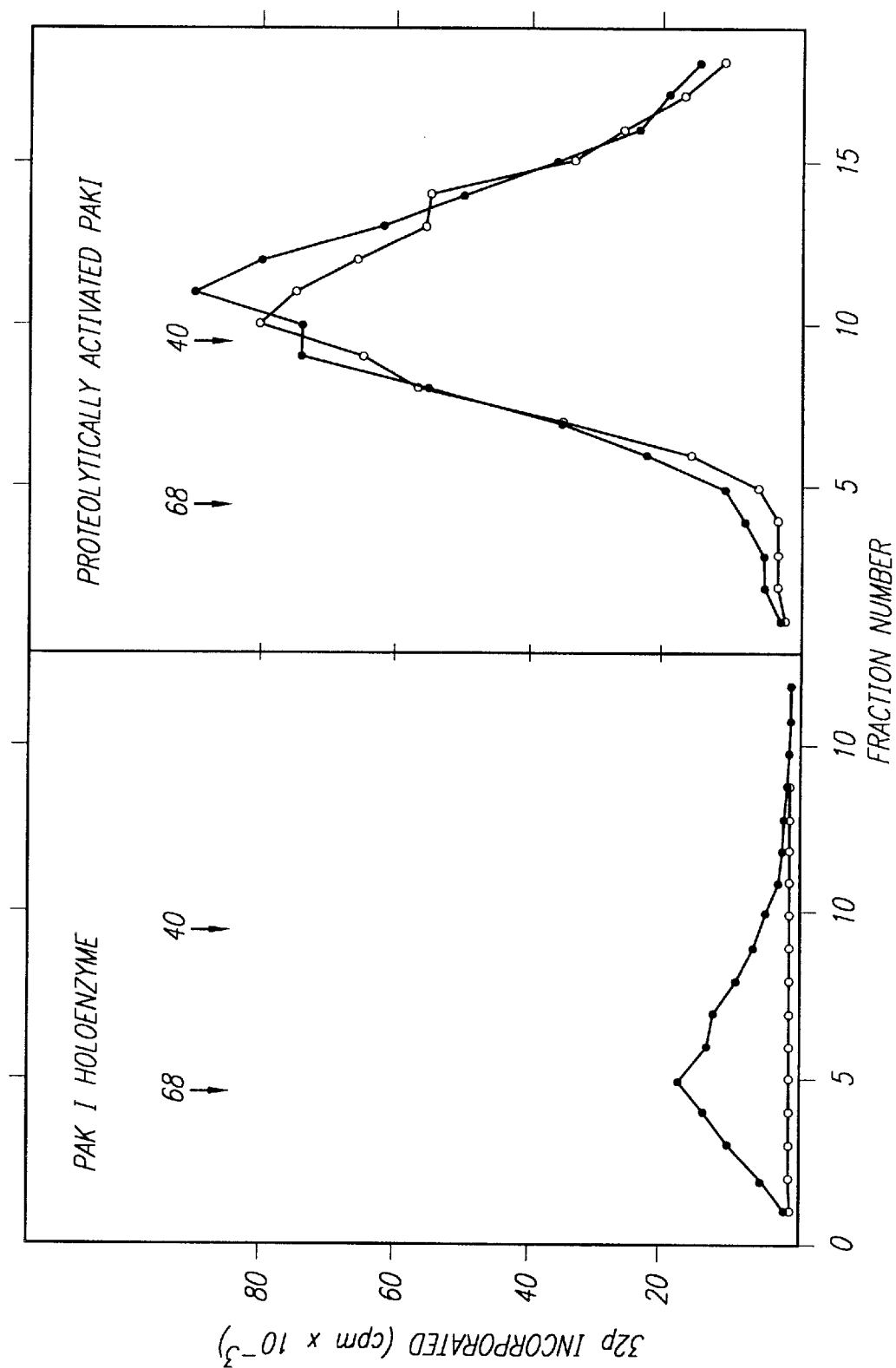
FIG. 4 presents molecular weight determination of inactive PAK I before and after proteolytic activation. Two samples of PAK I purified through Mono S were preincubated in the presence and absence of trypsin and analyzed by fast paced liquid chromatography (FPLC) on Superose 6. Prior to chromatography, the trypsin-activated enzyme was autophosphorylated. Aliquots (0.040 ml) of each fraction were assayed following preincubation in the presence (closed symbols) and absence (open symbols) of trypsin.

The highly purified holoenzyme and the activated enzyme were analyzed by gel filtration on Superose 6. The inactive holoenzyme migrated about 70 kDa, indicating a monomeric structure; polyacrylamide gel electrophoresis of the fractions showed the p60 protein coincided with the activity peak (FIG. 4). The catalytic activity of the proteolytically-activated enzyme migrated around 35 kDa upon gel filtration. When p37 was autophosphorylated prior to chromatography; the autophosphorylated peptide comigrated with the catalytic activity. Thus, inactive PAK I is a monomer and the p37 peptide generated by limited proteolysis contains the catalytic domain. The active p37 peptide is relatively labile and cannot be stored for any length of time.

Effects of Autophosphorylation of p37 on Protein Kinase Activity—The effects of autophosphorylation for 15 min in the presence and absence of ATP on the activity of the inactive holoenzyme and the p37 peptide were measured. Only a low level of activity was observed with the holoenzyme incubated either in the presence or absence of ATP. When the same samples were subjected to limited proteolysis, a 10-fold stimulation of activity was observed. Following preincubation of the proteolytically-activated enzyme with ATP, phosphorylated PAK I was activated 30-fold over the inactive PAK I, with a 3-fold stimulation of activity over the nonphosphorylated proteolytically activated enzyme.

Figure 5:
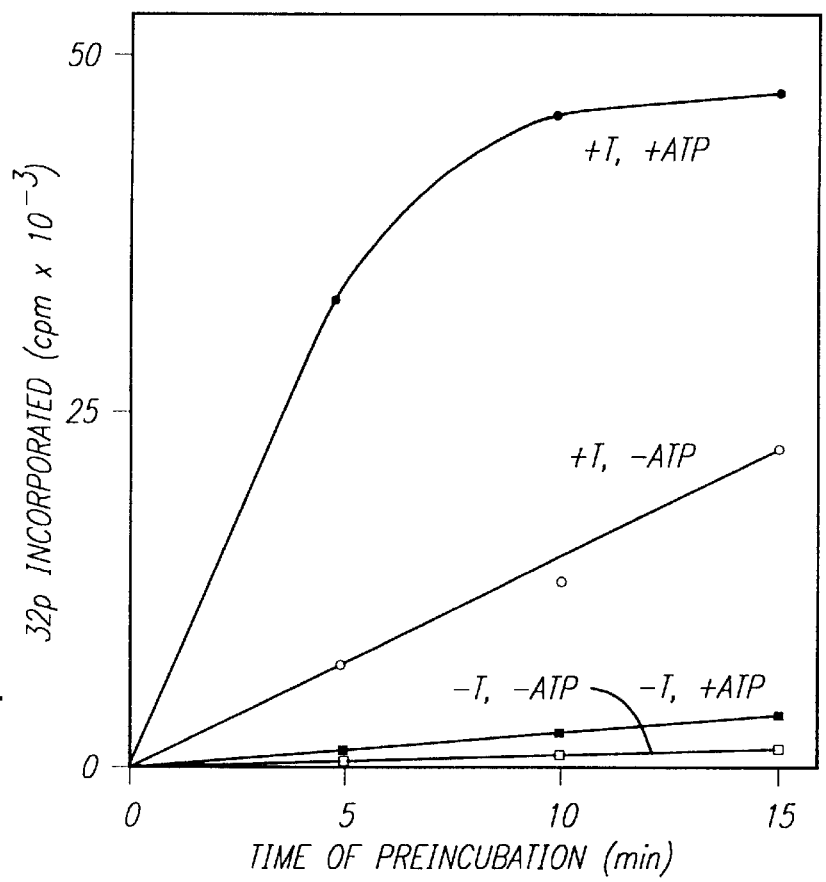
FIG. 5 presents the time course of the effects of autophosphorylation on PAK I activity. PAK I was preincubated in the presence and absence of trypsin, then each sample was preincubated in the presence and absence of ATP for 15 min and assayed in the presence and absence of histone for 0, 5, 10, and 15 min. (□) Preincubation in the absence of trypsin (–T) and ATP (–ATP); (■) preincubation in the absence of trypsin (–T) and presence of ATP (+ATP); (O) preincubation in the presence of typsin (+T) and absence of ATP (–ATP); (●) preincubation in the presence of trypsin (+T) and presence of ATP (+ATP).

A time course of stimulation of PAK I activity by autophosphorylation is shown in FIG. 5. During the first 5 min of incubation, the rate of phosphorylation of histone by autophosphorylated p37 was approximately 5-fold greater than that observed with nonphosphorylated p37. The activity leveled off by 15 min, suggesting the phosphorylated catalytic domain may be more labile than the nonphosphorylated enzyme.

The low level of activity observed with the holoenzyme showed a $K_m$ of around 2 mg/ml with mixed histone and a $K_{cat}$ of around 100 (TABLE I). Following proteolytic activation, the $K_m$ was reduced to 0.3–0.4 mg/ml with a $K_{cat}$ of around 800. Autophosphorylation of the catalytic domain stimulated the $V_{max}$ by 4-fold and the $K_{cat}$ about 7-fold.

Analysis of Autophosphorylation of the Two Forms of Active PAK I—PAK IA, highly purified by ion-exchange chromatography through the Mono S step, was analyzed by gel filtration on Superose 12. Aliquots (50 μl) of the fractions were assayed by incubation with [γ-$^{32}$P]ATP in the presence and absence of H4 as described in Experimental Procedures; histone phosphorylation was analyzed on 12.5% polyacrylamide gels and autophosphorylation on 7.5% gels. Purified PAK IA migrated as a distinct peak with a molecular mass of >400 kDa. A single protein of 205 kDa which copurified with the purified active enzyme upon gel filtration, was phosphorylated. No other phosphorylated protein comigrated with the PAK I activity, and PAK I (as p58) was not autophosphorylated. When PAK IB was analyzed in a similar manner, two phosphorylated proteins of 160 and 175 kDa copurified with the protein kinase activity. No autophosphorylation of PAK I protein at 58 kDa was observed. No effects of phosphorylation of the high molecular proteins on PAK I activity were observed. PAK IA and B also phosphorylated other proteins which have been shown to be phosphorylated by proteolytically-activated PAK I. These included H2B and myosin light chain from smooth muscle.

TABLE I

Kinetic Analysis of Inactive PAK I.

| PAK I | $K_m$ (mg/ml) | $V_{max}$ (pmol/min) | $K_{cat}$ |
|---|---|---|---|
| p60 | 1.7–2.7 | 180–260 | 67–150 |
| p37 | 0.3–0.4 | 250–300 | 600–1000 |
| p37 autophosphorylated | 0.6–0.8 | 1600–2000 | 2300–2800 |

DISCUSSION

PAK I has been purified to apparent homogeneity as an inactive monomer of 60 kDa as determined by polyacrylamide gel electrophoresis, which corresponds to a deduced molecular mass of 58,027 as determined by sequence analysis of the cDNA (EXAMPLE 3, below). The inactive holoenzyme is rapidly activated in vitro by limited proteolysis with trypsin; a peptide containing the active catalytic domain has a molecular weight of 37 kDa, as determined by polyacrylamide gel electrophoresis. Amino acid sequencing of the N-terminus of p37 has been carried out and compared to the cDNA; p37 contains 328 amino acids, the conserved catalytic domain plus 27 amino acids of the regulatory domain (EXAMPLE 3, below). Following proteolysis, no other major peptides are observed, indicating the regulatory domain which contains the binding site for Cdc42 is rapidly degraded.

p37 is highly autophosphorylated, whereas only a low basal level of phosphorylation is observed with the inactive holoenzyme. Phosphopeptide mapping shows the sites are different. The minor autophosphorylation of the holoenzyme is on serine. When autophosphorylation is carried out following limited proteolysis, the catalytic peptide becomes autophosphorylated on serine and threonine. Formation of p37 and the resultant autophosphorylation of the peptide are coincident with the increase in activity observed following proteolytic activation. The tryptic phosphopeptides from autophosphorylated inactive PAK I p60 are different from the phosphopeptides obtained with p37 as shown by 2-dimensional phosphopeptide mapping. However, the phosphopeptides observed with p60 are a light background pattern in the phosphopeptide map of p37 and vice versa.

The limited autophosphorylation observed with p60 does not result in activation of PAK I, neither does it affect the 10-fold stimulation of protein kinase activity after proteolysis. Autophosphorylation of the catalytic domain results in a 30-fold increase in activity over that observed with the holoenzyme and a 3-fold increase over non-phosphorylated p37. Proteolysis decreases the $K_m$ for the protein substrate whereas autophosphorylation of p37 results in a stimulation of $V_{max}$.

In the inactive holoenzyme, the regulatory domain appears to block binding of the protein substrate and ATP to the catalytic site. Activation by proteolysis results in cleavage of the regulatory domain, allowing the catalytic domain to become autophosphorylated. It is likely that cleavage mimics the effect of binding of Cdc42 to the inactive holoenzyme, which results in autophosphorylation and activation of PAK I (EXAMPLE 3, below), presumably through a change in conformation. Proteolysis does not appear to be a mode of activation of PAK I in vivo, but does appear to be involved in removal of the enzyme upon changes in cell status from an inactive to an actively dividing state, such as shown by addition of insulin (or serum) to quiescent or serum-starved 3T3-L1 cells and following fertilization of frog oocytes (EXAMPLE 2, below). However, proteolytic cleavage in vitro does result in an active moiety which has similar cytostatic properties to the purified active holoenzyme when injected into 2-cell embryos (EXAMPLE 2, below).

Two forms of the active holoenzyme have also been highly purified utilizing the same procedures as for inactive PAK I. These enzymes are present in minor amounts in reticulocytes (<10% of the total PAK I). Unlike the inactive form, which is a monomer, the active forms of PAK I are part of distinct high molecular weight complexes of >400 kDa. A protein of 205 kDa copurifies with the A form and is a substrate for the protein kinase. Two proteins of 160 and 175 kDa are substrates for and copurify with the B form. Active PAK I has a molecular weight of 58–59 kDa on SDS gels, slightly smaller than the inactive form. This difference in size is not due to proteolysis since the forms are interchangeable.

All forms of PAK I are dependent on free sulfydryl residues for activity; protein kinase activity is rapidly lost when sulfhydryl reducing agents are removed, or upon addition of NEM to either the holoenzyme or active enzymes.

As shown in EXAMPLE 3, below, autophosphorylation and the resulting activation of the inactive holoenzyme is stimulated by the small G protein Cdc42. Binding of the G protein could result in activation by producing a conformational change, thus allowing autophosphorylation of previously unavailable site(s). Proteolytic activation mimics this process by removal of the majority of the regulatory domain which negatively regulates the catalytic activity. Once removed, autophosphorylation occurs, stimulating the activity further. In this regard, it is interesting to note that the active holoenzymes cannot be autophosphorylated in vitro, which would be expected since autophosphorylation is required for activity (EXAMPLE 3, below).

This is the first large scale purification of both the active and inactive forms of a PAK enzyme. Both active PAK I and proteolytically-activated PAK I phosphorylate the same substrates. Purification and characterization of the p37 peptide, which has many of the properties of the endogenously activated enzyme without the requirement for activation, provides a useful tool in studies characterizing the role of PAK I in cytostasis.

Example 2

Cytostatic Activities of PAK I
Cleavage Arrest of Early Frog Embryos by the G Protein-Activated Protein Kinase PAK I In this study, PAK I was shown to be highly active in frog oocytes, and immunoblot analysis of PAK I showed antibody to PAK I reacted specifically with protein of 58–60 kDa. PAK I protein decreased rapidly at 60 min post-fertilization and little or no PAK I protein or activity was detectable at 80 min post-fertilization and in 2-cell embryos. PAK I protein was observed again at the 4-cell stage and increased thereafter, but was present primarily as an inactive form. Rac2 and Cdc42, but not Rac1, were present in oocytes and throughout early embryo development. To examine the effects of PAK I on cleavage arrest, endogenously active (58 kDa) and inactive (60 kDa) PAK I, and the active catalytic polypeptide (37 kDa) generated from inactive PAK I by limited proteolysis, were injected into early frog embryos. Injection of subfemtomole amounts of active PAK I or the active catalytic polypeptide into one blastomere of 2-cell frog embryos resulted in cleavage arrest in the injected cell at mitotic metaphase, while the uninjected blastomere progressed through mid- to late-cleavage. Injection of inactive PAK I had no effect on cleavage. Three other protein kinases, the catalytic subunit of cAMP-dependent protein kinase, protein kinase C and casein kinase II, administered at the same concentrations as PAK I had no effect on cleavage. Thus, PAK I appears to be a potent cytostatic protein kinase involved in maintaining cells in a non-dividing state. Evidence is provided to show that PAK I activity is high in oocytes and appears to be regulated by degradation/synthesis and through binding of Cdc42 and phosphorylation. PAK I may act to maintain cells in a non-dividing state through pathways involved in growth control, such as the stress-activated protein kinase (also known as the Jun kinase) signaling pathway and/or by regulation of multiple metabolic pathways.

EXPERIMENTAL PROCEDURES

Materials—Trypsin (diphenyl carbamyl chloride-treated), soybean trypsin inhibitor, and mixed histone IIAS were obtained from Sigma. Leupeptin, pepstatin, aprotinin, and histone H4 were from Boehringer Mannheim. Chemiluminescent detection reagent, protein kinase activity assay kits, and [$\gamma$-$^{32}$P]ATP were obtained from Amersham Corporation. Horeseradish peroxidase-conjugated goat anti-rat IgG was from Organan Teknika-Cappel, Durham, N.C., USA. The GST-fusion protein Cdc42Hs was generously provided by Dr. Channing Der, University of North Carolina, Chapel Hill, N.C., USA. Antibodies to Rac1, Rac2, and Cdc42 were from Santa Cruz Biochemicals, Santa Cruz, Calif., USA Superose 12 HR 10/30 and Mono Q HR 5/5 FPLC columns were from Pharmacia. Freon (1,1,2-trichlorofluoroethane) was from Aldrich, Milwaukee, Wis., USA. Casein kinase II from rabbit reticulocytes was purified by chromatography on DEAE-cellulose and phosphocellulose as described {Palen, E., et al., Biochem., 30:5586–5590 (1991)}. Protein kinase C was purified from bovine brain as described previously {Venema, R. C., et al., J. Biol Chem., 266:5298–5302 (1991)}. The catalytic subunit of cyclic AMP-dependent protein kinase was generously provided by Dr William H. Fletcher, J. L. Pettis Memorial Veterans Center, Loma Linda, Calif., USA.

Injection of Frog Embryos—Eggs from Lepidobatrachus laevis were naturally fertilized or fertilized in vitro {Carroll, E. J., Jr., et al., Dev. Growth Diff., 33:37–43 (1991)}. The first cleavage was observed approximately 90 min following fertilization, and cleavage continued at approximately 20 min intervals through mid to late cleavage. The embryos were selected at the beginning of the first furrow and injected 10 min thereafter. The protein kinase was diluted approximately 50-fold in buffer B (10 mM MOPS, pH 7.4, 1 mM dithiothreitol) and 50 nl (0.01–1 pg; 0.3–30 fmol) was injected into one blastomere. Cleavage arrest of the injected blastomere was monitored visually under a stereomicroscope for up to 2.5 hours following injection, as indicated.

Fluorescent Staining of DNA—Both blastomeres of 2-cell embryos were injected with active PAK I (1 pg/blastomere) and allowed to incubate for 30 min. Uninjected embryos developed to the 16-cell stage were used as controls. The embryos were lysed in the presence of 10 $\mu$l of Hoechst fluorescent dye 50 $\mu$g/ml {Newport, J. W., et al., Cell, 37:731–742 (1984)} and the DNA was examined under a fluorescent microscope (50×magnification) and photographed.

Western Blotting—Individual eggs and embryos were extracted in a volume of 250 μl with freon to remove the yolk proteins {Gurdon, J. B., et al., *Meth. Enymol.*, 101:370–386 (1983)} and frozen immediately. The extracts (20–25 μg) and the DEAE-cellulose column fractions (40–60 μl) were subjected to electrophoresis on 12.5% polyacrylamide slab gels in sodium dodecyl sulfate and transferred by electroblotting to nitrocellulose membranes. The samples were probed with antibody prepared to Rac1, Rac2, and Cdc42 diluted 1/200, and with rat polyclonal anti-PAK I antibody diluted 1/1000, and analyzed using peroxidase-conjugated goat and rabbit anti-rat secondary antibody by chemiluminescent detection. Polyclonal antibodies were raised in rat to the highly purified form of inactive form of PAK I from rabbit reticulocytes. PAK I (50 μg) was subjected to electrophoresis in a 12.5% polyacrylamide gel containing sodium dodecyl sulfate; the protein band was excised from the gel, mashed with a spatula, mixed with Freunds complete adjuvant (0.5 ml), and injected subcutaneously. The rats were bled from the tail vein on days 14 and 21. Subsequent boosting of the rat was carried out in a similar manner with 10–30 μg of PAK I in Freunds incomplete adjuvant. Antibody titer was quantified by Western blot analysis with purified PAK I from rabbit; the antibody was specific for PAK I and did not react with any other proteins in preparations from mammalian or frog tissues.

Chromatography of Frog Extracts—Oocytes, zygotes and early embryos collected at specific stages of development, were frozen in batches of 30 in liquid nitrogen, and stored at −70°. Prior to chromatography, the eggs were suspended and homogenized in 5.0 ml of buffer A (20 mM β-glycerophosphate, 1 mM dithiothreitol, 1 mM EDTA, 1 mM EGTA, 1 mM sodium vanadate, 1 mM sodium pyrophosphate, 0.01 mM cAMP, 0.5 mM phenylmethylsulfonyl chloride) containing 40 μg/ml of leupeptin, pepstatin, and aprotinin. The homogenate was centrifuged for 10 min at 12,000×g in a Sorvall SS 34 rotor and the supernate was collected and centrifuged for 1 hr at 47,000 rpm in a Beckman Ty65 rotor. The supernate was applied to a 0.5 ml DEAE-cellulose column (5.0×0.8 cm) equilibrated with buffer A and the resin was washed with 5 ml of buffer A. Protein was eluted with a 5 ml linear gradient (0–300 mM KCl) in buffer A; fractions of 0.33 ml were collected.

Assay for PAK I—PAK I was assayed before and after limited tryptic digestion using H4 or histone IIAS as substrate. Samples from column fractions (20 μl) were preincubated for 30 sec in 10 mM Tris-HCl pH 8.0 and 5 mM 2-mercaptoethanol in the presence or absence of 4 μg/ml trypsin in a volume of 40 μl. Proteolysis was terminated by the addition of 4 μl of a 10-fold molar excess of soybean trypsin inhibitor. Protein kinase activity was assayed with H4 (2.0 μg) in phosphorylation buffer containing 50 mM Tris-HCl, pH 7.4, 10 mM $MgCl_2$, 30 mM 2-mercaptoethanol, 0.20 mM [$\gamma$-$^{32}$P]ATP (specific activity 1000 cpm/pmol), and PAK I in a final volume of 70 μl. Leupeptin, pepstatin, and aproptinin were added at 8 μg/ml to the samples without trypsin prior to incubation, and to the samples containing trypsin following incubation. Incubation was for 15 min at 30° C.; the reactions were terminated by the addition of 10 μl of 10 mM nonlabeled ATP. Phosphorylation of H4 was analyzed by electrophoresis on 15% polyacrylamide slab gels in sodium dodecyl sulfate, followed by autoradiography {Hathaway, G. M., et al., *Meth. Enzymol.*, 60:495–511 (1979)}. Radioactivity was quantified by excising the histone band and counting in a liquid scintillation counter. Under these conditions, PAK I was limiting and incorporation was linear with time.

To assay for activation of PAK I by Cdc42, aliquots (30 μl) of column fractions were incubated with the G protein preloaded with GTPγS or GDP in 70 μl of phosphorylation buffer containing 1.4 μg soybean trypsin inhibitor at 30° C. for 10 min (as described in EXAMPLE 3, below) resulting in autophosphorylation of PAK I. An aliquot (30 μl) of the autophosphorylated enzyme was removed and assayed with H4 as described above.

Activity assays for MAPK, cdc2 kinase and casein kinase II were carried out in 30 μl reaction mixtures with 5–10 μl of enzyme using synthetic peptides highly selective for MAPK and specific for cdc2 kinase and casein kinase II as described by Amersham.

Purification of Active and Inactive PAK I—The inactive PAK I holoenzyme (p60) was purified to apparent homogeneity from rabbit reticulocytes by chromatography on DEAE-cellulose, SP-Sepharose fast flow, protamine-agarose, and FPLC on Mono S and Mono Q (EXAMPLE 1). The active PAK I holoenzyme (p58) was purified using similar procedures, but had slightly different chromatographic properties. To prepare large amounts of the catalytic domain (p37), inactive PAK I purified through the protamine-agarose step was subjected to limited tryptic digestion for 30 s, followed by addition of a 10-fold excess of soybean trypsin inhibitor {Tahara, S. M., et al., *J. Biol. Chem.*, 256:11558–11564 (1981)}. The activated enzyme was dialyzed against buffer A (20 mM Tris-HCl, pH 7.8, 3 mM dithiothreitol) containing 0.1 mM phenylmethylsulfonyl fluoride, and applied to a Mono-Q HR 5/5 column equilibrated in buffer A. The column was washed with 10 ml of buffer A and the enzyme was eluted with a 12.5 ml gradient of 0 to 0.45M NaCl in buffer A. The peak fraction was purified to apparent homogeneity on Superose 12 HC 10/30 in buffer A. Alternatively, highly purified PAK I was cleaved and the p37 peptide was autophosphorylated and passed over a pad of DEAE-cellulose to remove trypsin and trypsin inhibitor. Protein kinase activity was quantified as described earlier.

RESULTS

Figure 6A:
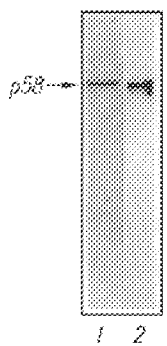
FIG. 6 Panel A presents purified inactive PAK I (p60) examined by polyacrylamide gel electrophoresis followed by staining with Coomassie blue (lane 1). Purified active PAK I (p58) was analyzed by Western blotting with antibody prepared to the inactive holoenzyme and visualized by chemiluminescence (lane 2).
Figure 6B:
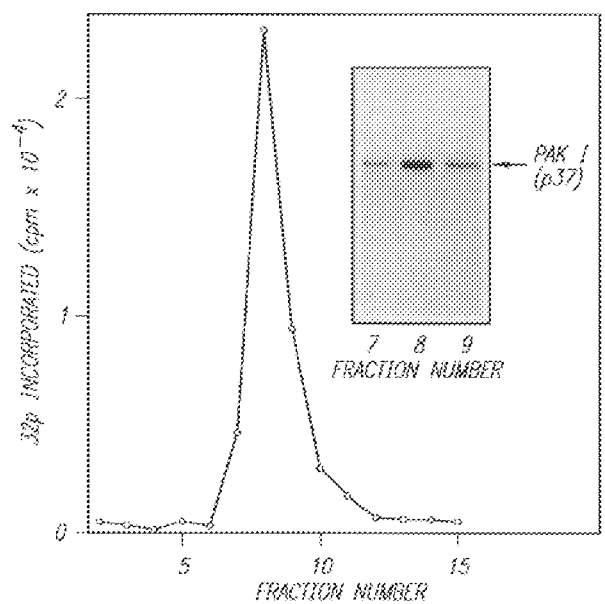
Figure 6C:
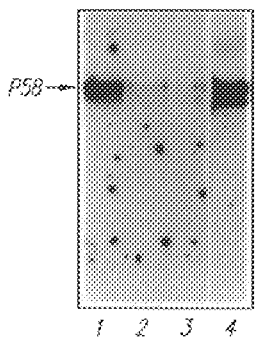
Figure 7A:
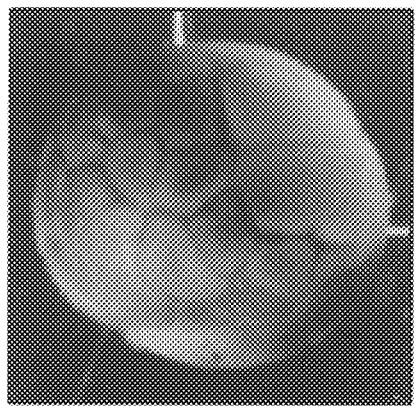
Figure 7B:
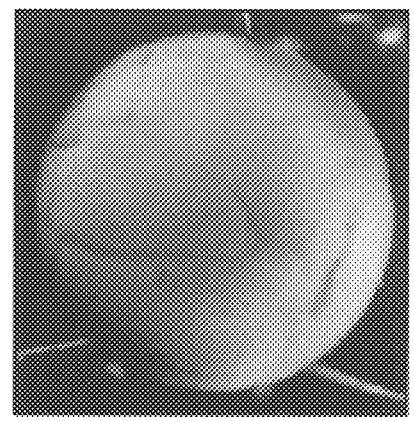
Figure 7C:
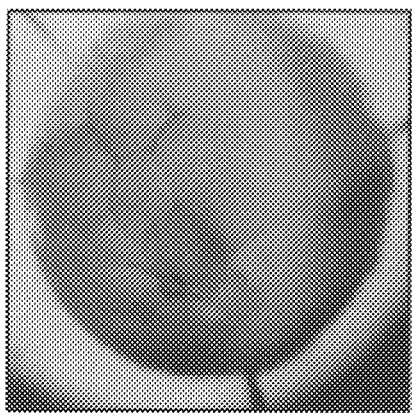
Figure 7D:
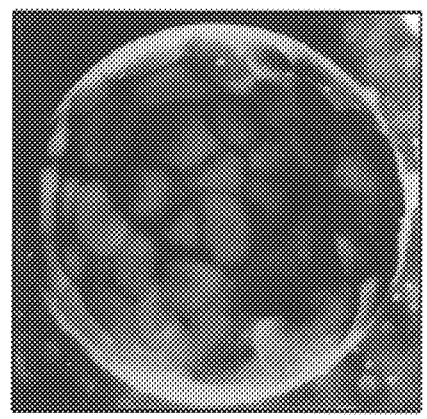
Figure 7E:
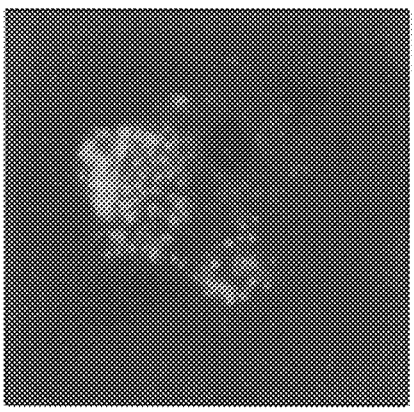
Figure 7F:
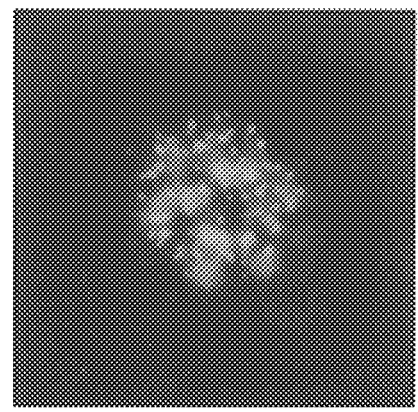

Analysis of the cytostatic activity of PAK I—The inactive holoenzyme of PAK I was purified to apparent homogeneity from rabbit reticulocytes by ion-exchange chromatography and FPLC and migrates as a single band at 60 kDa upon polyacrylamide gel electrophoresis in sodium dodecyl sulfate (FIG. 6). The endogenously active enzyme was purified in a similar manner and had a molecular weight of 58 kDa as shown by immunoblotting with antibody prepared to inactive PAK I. A 37 kDa peptide containing the catalytic domain of PAK I was generated by limited proteolytic digestion of the inactive holoenzyme, and purified to apparent homogeneity by FPLC on Mono Q and Superose 12 (FIG. 6, Panel B).

The biological activity of PAK I was analyzed using embryos from *Lepidobatrachus laevis*, since the eggs are easily injected and can be fertilized in vitro without destruction of the male, have very good embryo viability post-injection, and demonstrate rapid development {Carroll, E. J., Jr., et al., *Dev. Growth Diff.*, 33:37–43 (1991)}. Extracts of mature eggs, zygotes and 2-cell embryos were analyzed to determine whether an endogenous PAK I-like protein was present (FIG. 6, Panel C). Antibody prepared to mammalian PAK I reacted specifically with amphibian egg protein of 58–60 kDa, which was identical in molecular weight to PAK I in mammalian cells. The PAK I protein was present at significantly lower levels in the zygote and was greatly diminished at the 2-cell stage. When active PAK I (p58) was (TABLE II). Cleavage arrest was induced in 99% of the embryos injected with PAK I. When the same amount of PAK I was subjected to heat treatment (75° C. for 15 min) prior to injection, only 10% of the embryos exhibited cleavage arrest. All of the embryos injected with buffer alone proceeded through normal development. The normal division time was approximately 20 min, and arrest was observed within 30 min following injection of PAK I; cleavage of the injected blastomere did not progress beyond the 2- to 4-cell stage, while the other blastomere continued dividing up to and beyond late cleavage.

TABLE II

Injection of PAK I into frog embryos and arrest of cleavage.

| Experiment | Buffer | | PAK I p37 | | Heat-treated PAK I p37 | |
|---|---|---|---|---|---|---|
| | No. of Embryos Injected | Cleavage Arrest % | No. of Embryos Injected | Cleavage Arrest % | No. of Embryos Injected | Cleavage Arrest % |
| 1 | 13 | 0 | 6 | 100 | 9 | 0 |
| 2 | | | 13 | 100 | 9 | 10 |
| 3 | 30 | 0 | 57 | 100 | 41 | 12 |
| 4 | 7 | 0 | 20 | 100 | | |
| 5 | 13 | 0 | 15 | 93 | | |
| 6 | 14 | 0 | 18 | 100 | | |
| 7 | 14 | 0 | 12 | 100 | | |
| Total | 78 | | 141 | | 59 | |
| Average | | 0 | | 99 | | 10 |

Cleavage of the injected cell was arrested at the 2- to 4-cell stage, while the uninjected blastomere progressed to mid-cleavage (1 hour after injection) and late cleavage (2 hours). Data are shown for the 1 hour time point. Cells which were dead due to damage by injection (less than 10%) were omitted from the tabulated data.

injected into one blastomere of a 2-cell embryo, high levels of the protein migrated at the same position as the endogenous PAK I protein, as detected with antibody to PAK I.

To examine the effects of PAK I on cell cleavage, active PAK I (p58) was injected into one blastomere of embryos at the 2-cell stage of development and the embryos were allowed to develop for an additional 150 min. As shown in FIG. 7, Panels A and B, the injected cell was arrested, while the uninjected cell continued through normal division to late cleavage. Injection of the active catalytic domain (p37) also induced cleavage arrest as shown after 60 min of development (FIG. 7, Panel C). No cleavage arrest was observed in embryos injected with heat-denatured PAK I (FIG. 7, Panel D).

To determine the stage of arrest of the cell cycle, active enzyme was injected into both cells of a 2-cell embryo and incubation was continued for 30 min; at this point cell cleavage was arrested in both blastomeres. Fluorescent staining of the DNA (FIG. 7, Panel E) indicated the lack of a nuclear envelope and the presence of condensed chromosomes, which would be consistent with metaphase arrest. Fluorescent staining of DNA from normally developing embryos at the 16-cell stage showed the presence of a nuclear envelope and decondensed chromatin (FIG. 7, Panel F).

In a series of experiments in which different preparations of purified p37 containing the catalytic domain of PAK I were analyzed in 2-cell embryos, cleavage arrest occurred in the injected blastomere at concentrations of 0.1–1.0 pg Embryos injected at later stages of development (4- and 8-cell stages) exhibited cleavage arrest similar to that observed in the 2-cell embryos. In embryos injected with lower amounts of PAK I (0.01 pg), arrest observed at the early time periods ($\leq 1$ hr) was sometimes reversed at longer incubation times, leading to apparent normal development. At higher levels of active PAK I used in the experiments described herein ($\geq 0.1$ pg), reversal of arrest did not occur. This result suggests that the signal needs to be of sufficient strength and duration to negate the growth response.

When the purified endogenously active PAK I was injected into 2-cell embryos, results identical to those obtained with p37 were obtained (TABLE III). The active enzyme effected cleavage arrest at even lower concentrations than with the active p37 peptide. Injection of inactive PAK I at levels equivalent to those of active PAK I showed no effect on development. At 100-fold higher concentrations (20 pg), the inactive holoenzyme resulted in cleavage arrest in 50% of the embryos injected, indicating a very low level of protein kinase activity. This effect, observed at 30 and 60 min, was reversed at longer times of incubation. These data indicate that little or no activation of inactive PAK I occured in 2-cell embryos and active PAK I remained active for a period of time sufficient to intiate cytostasis. Thus, the components required for activation and inactivation of PAK I were not highly active and/or present in dividing cells.

TABLE III

Analysis of the effects of other forms of PAK I and other protein kinases on arrest of cleavage.

| Sample | Amount PAK I Injected (pg) | Total No. of Embryos Injected (total) | Cleavage Arrest (%) |
|---|---|---|---|
| Buffer Injected | | 78 | 0 |
| Active PAK I (p37) | 0.01–1.0 | 141 | 99 |
| Active PAK I (p58) | <0.01 | 28 | 96 |
| Inactive PAK I (p60) | 0.2 | 17 | 0 |
| | 20.0 | 16 | 50 |
| Casein Kinase II | 1.0 | 17 | 0 |
| cAMP-dependent Protein Kinase | 1.0 | 29 | 0 |
| Protein Kinase C | 2.0 | 9 | 0 |

Each sample (50 nl) was injected into one blastomere of a 2-cell embryo at the concentration indicated and analyzed at 1 hr post-injection. Three highly purified protein kinases, casein kinase II from rabbit reticulocytes, catalytic subunit of cAMP-dependent protein kinase from bovine heart and protein kinase C from bovine brain were similarly injected. These data were compiled from at least two experiments.

Experiments were also conducted to examine the effects of injection of three other protein kinases into 2-cell embryos (TABLE III). Cleavage arrest was not observed following injection of equimolar amounts of casein kinase II, the catalytic subunit of the cAMP-dependent protein kinase, or protein kinase C, at concentrations identical to those used for active PAK I. Taken together, the data indicate that cleavage arrest was specific for active PAK I and femtomole quantities produced a definitive cytostatic response.

PAK I, Rac2 and Cdc42 protein in oocytes and developing embryos—Extracts from frog oocytes, zygotes, and developing embryos at the 2-, 4-, and 16- to 32-cell stage were analyzed by immunoblotting with antibody to PAK I. The antibody was specific for PAK I and did not react with any other protein in the extract. PAK I protein (58–60 kDa) was present in the oocyte and the early zygote, but was significantly reduced at 60 min post-fertilization and almost non-detectible at 80 min post-fertilization and at the 2-cell stage (FIG. 6, Panel C). At the 4-cell stage, PAK I protein was again present and increased through the 16- to 32-cell stage, but was significantly less than in the oocyte. To analyze for potential activators of PAK I, the same extracts were examined by immunoblotting with antibody prepared to Rac1, Rac2, and Cdc42. Rac2 and Cdc42 were present in the oocyte and throughout early embryogenesis. Rac1 was not detectable in the same experiments.

Active and inactive forms of PAK I in oocytes, zygotes, and developing embryos—As it is not possible to accurately measure PAK I activity in cell extracts, PAK I was analyzed following chromatography on DEAE-cellulose. Fractions from mature oocytes were assayed for active PAK I under kinetically valid conditions and phosphorylation of H4 was quantified by SDS-PAGE followed by autoradiography. H4 is specific for PAK I and is not phosphorylated by other major protein kinases. Two peaks of active PAK I were observed to elute at 0.06–0.11M KCl (fractions 5 and 6) and 0.12–0.2M KCl (fractions 7 to 9). Fractions eluting at salt concentrations above 0.2M contained protein kinase activity which phosphorylated a major frog oocyte protein of 32 kDa, and other endogenous proteins to lesser extent.

To identify the inactive form of PAK I, aliquots of the DEAE-fractions were subjected to limited tryptic digestion prior to assay for PAK I or preincubated with Cdc42(GTPγS) and ATP. Three peaks of activity were identified, as indicated by the arrows. The early eluting peak (0.03–0.05M KCl) contained inactive PAK I, which was observed only after limited proteolytic digestion or preincubation with Cdc42 (GTPγS). The degree of activation was similar (6- to 7-fold), under both conditions. Peak 2 (0.06–0.11M KCl) contained two different forms of PAK I, one requiring activation, and a second active enzyme. All of the enzyme in peak 3 was active. The total amount of active enzyme in peak 3 was 3-fold higher than that observed in peak 2. The data were consistent with the Western blot profile in which protein migrating between 58–60 kDa coincided with all three peaks of PAK I activity.

Aliquots of the DEAE-cellulose fractions were subjected to Western blot analysis using antibody prepared against purified PAK I from rabbit. The antibody reacted specifically with proteins of 58–60 kDa in the fractions containing PAK I activity. The antibody also reacted with a protein doublet of the same molecular weight in fraction 4 (0.05M KCl) which had little active enzyme, but eluted at the position of inactive PAK I from other species and tissues {Rooney, R. D., et al., FASEB J, 6:A1852 (1992); Tahara, S. M., et al., Eur. J. Biochem., 126:395–399 (1982); Tahara, S. M., et al., J. Biol. Chem., 256:11558–11564 (1981); Tuazon, P. T., et al., Eur. J. Biochem., 129:205–209 (1982); and Tuazon, P. T., et al., J. Biol. Chem., 259:541–546 (1984)}. The initial peak of active PAK I contained a doublet of 58–60 kDa, while the later peak contained a single protein of 59 kDa.

To examine PAK I activity following fertilization and during early cleavage, postribosomal supernates from zygotes and embryos at the 4- and 16- to 32-cell stages were chromatographed on DEAE-cellulose and assayed for PAK I activity. Following fertilization, PAK I activity was greatly reduced; little active enzyme or activatable enzyme was detected. This data coincided with the diminished level of PAK I protein at this stage. By the 4-cell stage, a small amount of active enzyme was observed in Peak 2, while the majority of PAK I was present as inactive enzyme.

When active and inactive PAK I were quantified at different stages of development (FIG. 8), PAK I activity was maximal in the oocyte, with 66% of the enzyme in an active state. The level of total enzyme activity decreased dramatically upon fertilization. The zygote contained only minor amounts of active and inactive PAK I as compared with the mature oocyte. An increased level of inactive PAK I was observed at the 4- and 16- to 32-cell stages. Four-cell embryos contained 31% and 16- to 32-cell embryos contained 41% of the total PAK I activity observed in mature oocytes, with approximately 75% of PAK I present as inactive enzyme.

Analysis of other protein kinases in oocytes and developing embryos—The activities of other protein kinases in mature oocytes were also examined to compare the regulation of PAK I with that of other protein kinases. The DEAE-cellulose fractions were assayed under kinetically valid conditions, using synthetic peptides specific for cdc2 or casein kinase II, or highly selective for MAPK. Levels of these protein kinase activities were analyzed and compared to the activities in eggs (TABLE IV). MAPK activity decreased to almost undetectable levels following fertilization (zygote), and remained inactive in the 4-cell and 16- to 32-cell embryos. Cdc2 activity was similarly undetected in zygotes, although low levels were present in the 4-cell (8%) and 16- to 32-cell embryos (25%). In contrast to MAPK and cdc2, casein kinase II activity was present at about the same level at all stages.

TABLE IV

Protein Kinase Activity in Frog Eggs and at Different Stages of Early Embryo Development.

| Protein Kinase | PROTEIN KINASE ACTIVITY (%) | | | |
|---|---|---|---|---|
| | Mature Oocyte | Zygote | Embryo (4-Cell) | Embryo (16- to 32-Cell) |
| MAPK | 100 | 0 | 2 | 0 |
| Cdc2 | 100 | 0 | 8 | 25 |
| Casein Kinase II | 100 | 82 | 91 | 90 |
| PAK I | | | | |
| Total | 100 | 16 | 31 | 41 |
| Active | 66 | 9 | 6 | 13 |
| Inactive* | 34 | 7 | 25 | 29 |

*Activity of the inactive form was measured following limited proteolysis.

DISCUSSION

In these studies, PAK I has been shown to be a potent inhibitor of cleavage in early amphibian embryos. Injection of subfemtomole amounts of active PAK I into one blastomere of a 2-cell embryo arrested cleavage in the injected cell at metaphase, while the other blastomere continued to divide. The levels of PAK I needed to induce arrest were significantly lower than those used with MAPK and similar to those of Mos {Haccard, O., et al., *Science*, 262:1262–1265 (1993)}. Neither the inactive form of PAK I nor heat-treated PAK I were inhibitory, suggesting that arrest is due to phosphorylation of proteins which alter the cell cycle. Thus, PAK I appears to play an important role in maintaining cells in a non-dividing state. This state could be rapidly released or reversed by changes in PAK I activity and/or by degradation.

PAK I protein is highly conserved between species, since antibody prepared to rabbit PAK I reacts specifically with a protein of the same molecular weight in mature frog oocytes. High levels of PAK I activity and protein were identified in mature oocytes, consistent with the cytostatic activity of active PAK I observed upon injection into dividing embryos. Approximately 1 hour following fertilization, total PAK I activity dropped to a low level and remained low through the 2-cell stage; the loss in PAK I activity appeared to be due to protein turnover, as shown by immunoblots of extracts from zygotes and 2-cell embryos. At the 4-cell stage, PAK I protein was again observed, but at lower levels than the oocyte; however, the inactive form was predominant in 4- and 16- to 32-cell embryos. The identification of PAK I as a Cdc42-activated protein kinase (EXAMPLE 3, below), the identification of Cdc42 and Rac2 in the oocyte and thoughout early development, and the activation of oocyte PAK I by Cdc42, suggest that PAK I activity is regulated by Cdc42 in vivo as well as in vitro.

The complex chromatographic elution profile for PAK I during the early embryonic development, consisting of three individual peaks of PAK I, may be due at least in part to differential phosphorylation and to association with other proteins. PAK I is multiply phosphorylated as shown by two-dimensional isoelectric focusing/SDS gels. PAK I in frog eggs is activated by proteolysis or by association with Cdc42(GTP$\gamma$S). The molecular mass of PAK I varies from 58–60 kDa, depending on the state of the enzyme. Thus, regulation of PAK I in germ cells is a complex mechanism involving degradation/synthesis, G proteins and phosphorylation.

Multiple forms of PAK I, similar to those described herein, have also been identified in 3T3-L1 cells and rabbit reticulocytes. Three forms of PAK I (58–60 kDa) have been highly purified from rabbit reticulocytes (EXAMPLE 1). The three peaks of PAK I activity observed upon chromatography of frog egg extracts on DEAE-cellulose is consistent with these three forms of activity. With 3T3-L1 cells, the elution patterns of PAK I on DEAE-cellulose are dependent on the growth state of the cells. Chromatography profiles of PAK I from quiescent 3T3-L1 cells are similar to those observed with mature oocytes, and PAK I profiles from dividing cells are similar to those observed in the 16- to 32-cell stage.

MAPK and cdc2 kinase activities were high in mature eggs and greatly diminished after fertilization. In the 4-cell and 16- to 32-cell embryos, MAPK was not detectable, as shown previously, in Xenopus {Daar, I., et al., *Science*, 253:74–76 (1991); Kosako, H., et al., *J. Biol. Chem.*, 269:2835–428358 (1994); Haccard, O., et al., *Science*, 262:1262–1265 (1993); and Gotoh, Y., et al., *Nature* (London), 349:251–254 (1991)}. Low levels of cdc2 kinase activity was observed in the 4-cell and 16- to 32-cell embyros. In Xenopus, cdc2 kinase is active during oocyte maturation, inactivated after fertilization, and oscillates between inactive enzyme at interphase and full activity in the early mitotic cycles {Gotoh, Y., et al., *Nature* (London), 349:251–254 (1991); Pomerance, M., et al., *J. Biol. Chem.*, 267:16155–16160 (1994); King, R. W., et al., *Cell*, 79:563–571 (1994); and Gautier, J., et al., *Nature* (London), 339:626–629 (1989)}. The low levels of cdc2 kinase activity measured in the 4-cell and 16- to 32-cell embryos in these studies could be due to a heterogenous mixture of embryos at interphase and M-phase. Casein kinase II remained at approximately the same level in all of the embryonic stages examined, suggesting that casein kinase II is not involved in regulation of cleavage arrest. This result is consistent with the lack of effect observed upon injection of casein kinase II into one blastomere of 2-cell frog embryos.

Active PAK I injected into early embryos at the 2-cell stage remains active for a period sufficient to arrest cleavage. Proteases activated upon fertilization which could degrade PAK I would be shut off relatively quickly to preserve the integrity of the egg, and would not be expected to be present at the 2-cell stage. Inactive PAK I injected at the 2-cell stage is not activated either by G proteins or proteolysis. This is consistent with the fact that PAK I is primarily in an inactive form in the 4-cell and 16- to 32-cell stages.

It thus appears that G protein activity could be limiting in the early embryos. The G proteins express an intrinsic GTPase activity and cycle between active GTP-bound and inactive GDP-bound forms {Boume, H. R., et al., *Nature*, 349:117–127 (1991)}. Three different classes of proteins modulate the cycling process; these include the GTPase-activating proteins which enhance GTP hydrolysis resulting in down-regulation, guanine nucleotide exchange factors (GEFs) which exchange GDP for GTP, and guanine nucleotide dissociation stimulators {Hall, A., *Mol. Biol. Cell*, 3:475–479 (1992)}. Any or all of these proteins could be regulated during early development resulting in changes in Cdc42 activity. Taken together, these data suggest that PAK I regulation in the oocyte and early embryonic development is through G proteins and by synthesis/degradation.

Ras, activated in response to growth promoting compounds, stimulates the MAPK cascade. Under these same conditions, the JNK pathway does not become activated. In contrast, the JNK pathway is activated under conditions of stress, including toxic inhibition of protein synthesis, inflammatory cytokines, heat shock, ultraviolet irradiation and osmotic imbalance {Coso, O. A., et al., *Cell*, 81:1137–1146 (1995) and Minden, A., et al., *Cell*, 81:1147–1157 (1995)}. This pathway is mediated by the G proteins Rac1 and Cdc42, and GEFs specific for these proteins can stimulate JNK activity. Data by Coso, et al. {Coso, O. A., et al., *Cell*, 81:1137–1146 (1995)} and Minden, et al. {Minden, A., et al., *Cell*, 81:1147–1157 (1995)} suggest that Rac1 and Cdc42 can independently mediate this stress-regulated pathway and postulate a PAK or PAK-related protein kinase may be involved in the regulation thereof. Our observations with frog eggs support that postulate with the following evidence. First, PAK I has been shown to be specifically activated by Cdc42. Second, Cdc42 is present in oocytes and during early embryo development. Third, PAK I has been shown to have cytostatic properties upon injection into early frog embyros. Fourth, the high levels of activity in mature oocytes and quiescent cells are consistent with this thesis. Fifth, PAK I appears to be a universal enzyme, present in all higher animal species and tissues. Thus, PAK I appears to be the PAK enzyme involved in dampening or shutting down cell metabolism in response to physiological stress, as well as maintaining cells (and organisms) in a non-dividing state.

Regulation of PAK I in 3T3-L1 Cells by Serum Deprivation and Insulin

In these studies, with serum-fed 3T3-L1 cells, the majority of PAK I (around 60%) was present in an inactive state. Serum-starvation for 1 ½ hr increased PAK I activity by 2.5-fold and the majority of PAK I (approximately 67%) was present as active enzyme; similar results were obtained with quiescent cells. Insulin treatment of serum-starved cells for 15 min resulted in a dramatic decrease in both PAK I activity and protein. Thus, PAK I activity is stimulated under conditions of growth-arrest, as compared to actively dividing cells, and PAK I activity and protein are greatly diminished following 15 min of insulin administration to serum-starved cells. The data corroborate studies in frog eggs showing PAK I has cytostatic properties and is regulated by cycling between active and inactive enzyme and by synthesis/degradation during early embryogenesis.

EXPERIMENTAL PROCEDURES

Materials—Diaminobenzoic acid and myosin light chain from skeletal muscle were obtained from Sigma. [γ-$^{32}$P]ATP and chemiluminescent reagent were obtained from Amersham Corporation. Polyvinyldine difluoride membrane was purchased from Millipore Corporation, Bedford, Mass., USA. Horseradish peroxidase-conjugated goat anti-rat IgG was from Organan Teknika-Cappel. Active and inactive forms of PAK I were highly purified from rabbit reticulocytes as described elsewhere in EXAMPLE 1.

Cell Culture—3T3-L1 cells were grown on 100 mm culture plates in Dulbecco's modified Eagle's medium containing 10% fetal calf serum. To obtain exponentially dividing cells, the cultures were refed on day 3 and incubated an additional 24 hr to a confluency of approximately 60%. The media was removed from 20 plates and the plates were washed twice with 2 ml of phosphate buffered saline. The cells were released with 3 ml of phosphate-buffered saline containing 4 mM EDTA upon incubation for 5 min at 37° C. The cells were removed, centrifuged for 10 min at 500×g, and resuspended in 3 ml of buffer A (20 mM β-glycerophosphate, 10 mM 2-mercaptoethanol, 1 mM EDTA, 1 mM EGTA, 1 mM sodium vanadate, 1 mM sodium pyrophosphate, 0.01 mM cAMP, and 0.5 mM phenylmethylsulfonyl chloride) containing 40 μg/ml of leupeptin, pepstatin and aprotinin.

Serum-starvation was carried out by incubating exponentially growing cells in the absence of serum for 1.5 hr, then harvested as described above. Serum-starved cells were also treated with 10$^{-7}$M insulin for 15 or 30 min prior to harvest.

Chromatography on DEAE-cellulose—3T3-L1 cells from 20 plates were harvested; following sonication, the extracts were centrifuged for 10 min at 12,000×g. The supernates were collected, brought to 10 ml in buffer A, and centrifuged for 1 hr at 47,000 rpm using a Beckman Ty65 rotor. Supernate protein was quantified as described by Bradford {*Anal. Biochem.*, 72:248–254 (1976)} using γ-globulin as a standard. The supernate was applied to a 1 ml DEAE-cellulose column (5.0×0.8 cm) equilibrated in buffer A and the resin was washed with 10 ml of the same buffer. Protein was eluted with a 10 ml gradient from 0–300 mM KCl in buffer A; 0.66 ml fractions were collected.

Two-dimensional Isoelectric Focusing/Electrophoresis—Two-dimensional isoelectric focusing/electrophoresis was carried out according to O'Farrell, et al. {*Cell*, 12:1133–1142 (1977)} using an ampholine mixture of pH 3.5–10 in the first dimension, and 12.5% polyacrylamide in the second dimension. The gels were electroblotted onto nitrocellulose membranes and subjected to Western blot analysis.

RESULTS

Analysis of PAK I from exponentially growing 3T3-L1 cells—To determine the conditions under which PAK I was activated in vivo, extracts from exponentially growing 3T3-L1 cells were chromatographed on DEAE-cellulose and the fractions were assayed for PAK I activity using histone as substrate. The active form of PAK I could be assayed directly; however, the inactive holoenzyme could be assayed only after activation by Cdc42 or by limited tryptic digestion. Three peaks of activity were observed. The first peak eluted between 25 and 65 mM KCl and contained primarily the inactive form of PAK I; activity was stimulated 3.2-fold following limited proteolysis.

A smaller peak containing both active and inactive PAK I eluted between 75 and 110 mM KCl and the activity was stimulated 1.6-fold by limited proteolysis. The third peak contained only active PAK I and eluted between 100 and 180 mM KCl. A similar elution profile for the active and inactive forms of PAK I has been observed in frog oocytes and rabbit reticulocytes (EXAMPLE 1).

To verify the identity of PAK I, aliquots of the DEAE-cellulose fractions were subjected to Western blot analysis using polyclonal antibody prepared to inactive PAK I from rabbit. The polyclonal antibody was specific for PAK I and reacted only with a protein doublet of 58 and 60 kDa. This protein was present in all fractions containing PAK I activity. These data are coincident with that obtained with purified inactive PAK I from rabbit reticulocytes which has a molecular mass of 60 kDa, and with purified active enzyme with a molecular mass of 58–59 kDa (EXAMPLES 1 AND 2).

Analysis of PAK I in 3T3-L1 cells following serum-starvation and insulin-treatment—In order to determine whether PAK I activity was altered by the state of cell growth, 3T3-L1 cells were subjected to serum-starvation for 1.5 h, or to confluency, and analyzed as described above. Serum-starved 3T3-L1 cells were also treated with insulin for 15 min. Activity assays of the fractions were consistent with Western blot analysis showing changes in levels of PAK I protein.

The total amount of PAK I from serum-fed, serum-starved and insulin-treated cells, as well as the levels of active and inactive PAK I were quantified as shown in TABLE V. In serum-fed cells, approximately 60% of the PAK I was present as inactive enzyme, with 40% of the PAK I active. Serum-starved cells contained the highest level of total PAK I, 1.5-fold more than the serum-fed cells; 67% of PAK I was in an active state. The level of PAK I cells was 40% that of serum-fed cells. Total PAK I activity decreased dramatically in serum-starved 3T3-L1 cells treated with insulin for 15 min. These cells contained 54% of the PAK I in serum-fed cells and 37% of serum starved-cells. The level of active enzyme was 21% of that observed with serum-fed and 14% of serum-starved cells.

TABLE V

PAK I activity in serum-fed, serum-starved, and serum-starved/insulin-treated 3T3-L1 cells.

| | PAK I ACTIVITY | | | | | |
|---|---|---|---|---|---|---|
| | Serum-fed | | Serum-starved | | Insulin-treated | |
| PAK I | (u/mg)* | (%)** | (u/mg) | (%) | (u/mg) | (%) |
| Total | 1149 | 100 | 1694 | 147 | 621 | 54 |
| Active | 459 | 40 | 1142 | 99 | 243 | 21 |
| Inactive | 690 | 60 | 552 | 48 | 378 | 33 |

*The amount of PAK I that incorporates 1 pmol of phosphate into histone/mg of total extract protein/min at 30° C.
**Calculated by setting the total activity in serum-fed cells at 100%.

The fractions from the serum-starved and insulin-treated cells were analyzed further by in situ phosphorylation of mixed histone in polyacrylamide gels following electrophoresis. The in situ assay showed active PAK I from serum-starved cells migrated at 58 kDa. Inactive PAK I activity, migrating at 60 kDa, was observed only after activation. Thus, the 58 kDa form of PAK I coincided with active enzyme and the 60 kDa form with inactive PAK I. This data was similar to data obtained with purified active and inactive PAK I from rabbit reticulocytes (EXAMPLE 1). Similar results were observed with serum-starved/insulin-treated cells, except that the majority of PAK I required activation. These results are in close agreement with the activity assays and Western blot profiles. In situ phosphorylation was also carried out in polyacrylamide gels cast with myosin light chain from skeletal muscle, since it was shown to be a substrate for PAK I {Tuazon, P. T., et al., Eur. J. Biochem., 129:205–209 (1982)}. Observations similar to those obtained with mixed histone were obtained.

Analysis of PAK I by Isoelectric Focusing—Two-dimensional isoelectric focusing/electrophoresis of PAK I from serum-fed and serum-starved cells was compared with purified inactive PAK I from rabbit. Four isoforms of inactive PAK I from rabbit were observed by Western blotting. An abundant elongated spot, which consisted of two isoforms, migrated in the first dimension between pH 5.4 and 5.8 and in the second dimension at 60 kDa. These isoforms were more basic than the other two forms, which migrated with a pH around 4.5 with the more abundant isoform migrating with a molecular mass of 58 kDa and the minor form with a molecular mass of 60 kDa.

Western blots of PAK I from both serum-treated and serum-starved 3T3-L1 cells contained the same four isoforms plus an additional isoform. In serum-fed cells, the two most acidic isoforms were present at higher levels and the most basic isoforms were present only in very low amounts. A new isoform migrated with an intermediate pH at 60 kDa. Six distinct spots were detected in serum-starved cells. The five spots observed previously and a new isoform migrating at an intermediate pH with a molecular mass of 58 kDa. This form would correspond to active PAK I.

Taken together, the data show that PAK I is present in multiple forms in 3T3-L1 cells, and PAK I activity and the forms of PAK I change with hormonal treatment. The isoelectric focusing data are consistent with multiple phosphorylation states of PAK I, where the active form has a molecular mass of 58 kDa. In addition, phosphorylation/dephosphorylation at specific sites appears to alter the confirmation of PAK I such that the molecular weight is also altered.

DISCUSSION

Regulation of PAK I has been examined in extracts from serum-treated, serum starved, and serum starved 3T3-L1 cells treated with insulin for 15 min. PAK I is present in both active and inactive isoforms which chromatographed differently on DEAE-cellulose. In actively dividing serumfed cells, the majority of PAK 1 (60%) is present as an inactive enzyme of 60 kDa. Following serum-starvation for 1.5 h, activity is stimulated 2.5-fold, with 67% of PAK I in an active state. Upon insulin treatment of the serum-starved cells for 15 min, total PAK I activity is reduced 2-fold as compared to serum-fed cells and 3-fold compared with serum-starved cells. Active PAK I is reduced to 21% of that in serum-fed and to 14% of serum-starved cells.

The presence of different levels of active and inactive forms of PAK I in 3T3-L1 cells under conditions which stimulate cell growth or arrest suggests complexity in regulation and function of enzyme. Binding of Cdc42 to PAK I stimulates autophosphorylation resulting in activation of the protein kinase activity. The data from the two-dimensional isoelectric focusing gels reveal an increased number of active isoforms of PAK I in fractions containing active enzyme as compared to the four common isoforms of inactive rabbit PAK I. The presence of multiple forms of both active and inactive PAK I may be explained at least in part by phosphorylation. The identification of multiple isoforms upon isoelectric focusing suggests regulation of PAK I is due to phosphorylation/dephosphorylation at multiple sites. This regulation is also reflected in the shift in molecular mass between the active and inactive enzyme.

Example 3

Molecular Cloning and Sequencing of PAK I

To clone the cDNA encoding PAK I, purified peptides from rabbit PAK I were sequenced, degenerate oligonucleotides were used to isolate PAK I clones from a rabbit spleen library, and the 5'-terminus was obtained by polymerase chain reaction. The entire cDNA sequence extends over 4471 nucleotides, with an open reading frame for a protein of 524 residues and a 3'-noncoding region of 2826 nucleotides. Clones with the same open reading frame, but with 3'-noncoding regions of 1055 and 2478 nucleotides were isolated, suggesting the generation of different transcripts by alternative termination of transcription. The amino acid sequence of PAK I shows high homology to the p21-activated protein kinases from human placenta and rat brain and to yeast STE20. PAK I is activated by Cdc42(GTP). The PAK enzymes have been proposed to regulate the stress-activated protein kinase (also known as the Jun kinase) signaling pathway {Coso, O. A., et al., Cell, 81:1137–1146 (1995); Minden, A., et al., Cell, 81:1147–1157 (1995)}.

The cloning and sequencing of the cDNA encoding PAK I, described herein, has revealed a mode of regulation of PAK I activity. The N-terminal regulatory domain contains a G protein binding region similar to that of the G protein-activated protein kinases, including rat brain PAK65 {Manser, E., et al., *Nature,* 367:40–46 (1994)}, human placenta PAK65 {Martin, G. A., et al., *EMBO J.,* 14:1970–1978 (1995)} and yeast STE20 {Manser, E., et al., *Nature,* 367:40–46 (1994)}. Binding of the small G protein Cdc42 stimulates autophosphorylation and protein kinase activity, as shown by phosphorylation of H4.

The serine/threonine protein kinase PAK I (p21-activated protein kinase) was first detected as an inactive holoenzyme that could be converted into an active form by limited proteolysis with trypsin, chymotrypsin, or a $Ca^{2+}$-stimulated protease {Tahara, S. M., et al., *J. Biol. Chem.,* 256:11558–11564 (1981); Tahara, S. M., et al., *Eur. J. Biochem.,* 126:395–399 (1982); Tuazon, P. T., et al., *Eur. J. Biochem.,* 129:205–209 (1982); Tuazon, P. T., et al., *J. Biol. Chem.,* 259:541–546 (1984) and EXAMPLE 2}. Inactive PAK I is a monomer of 60 kDa, and the active peptide is 37 kDa (EXAMPLE 1). PAK I appears to be highly conserved across species and has been found in all animals and tissues examined to date {Tahara, S. M., et al., *J. Biol. Chem.,* 256:11558–11564 (1981); Tahara, S. M., et al., *Eur. J. Biochem.,* 126:395–399 (1982); Tuazon, P. T., et al., *Eur. J Biochem.,* 129:205–209 (1982); Tuazon, P. T., et al, *J. Biol. Chem.,* 259:541–546 (1984) and EXAMPLE 2}. Two endogenously active forms of PAK I of 58 kDa were recently detected in 3T3-L1 cells (EXAMPLE 2, above), rabbit reticulocytes (EXAMPLE 1, above) and frog oocytes (EXAMPLE 2, above). PAK I phosphorylates a number of proteins including H2B and H4 {Tahara, S. M., et al., *J. Biol. Chem.,* 256:11558–11564 (1981)}; myosin light chain from smooth and skeletal muscle {Tuazon, P. T., et al., *Eur. J. Biochem.,* 129:205–209 (1982); and Tuazon, P. T., et al., *J. Biol. Chem.,* 259:541–546 (1984)}; translational initiation factors eIF-3, eIF-4B, and eIF-4F {Tahara, S. M., et al., *Eur. J. Biochem.,* 126:395–399 (1982); and Tuazon, P. T., et al., *J. Biol. Chem.,* 264:2773–2777 (1989)}; and avian and Rous sarcoma virus nuclear capsid protein NC {Leis, J., et al., *J. Biol. Chem.,* 259:7726–7732 (1984); Fu, X., et al., *J. Biol. Chem.,* 260:9941–9947 (1985); and Fu, X., et al., *J. Biol. Chem.,* 263:2134–2139 (1988)}.

EXPERIMENTAL PROCEDURES

Materials—$^{32}$P-labeled and $^{35}$S-labeled nucleotides as well as Hybond-N membranes were purchased from Amersham Corp. Immobilon-P was obtained from Millipore Corp. and ProBlott was from Applied Biosystems Inc., Foster City, Calif., USA. Endopeptidase Asp-N was purchased from Boehringer Mannheim. The Vydac reverse phase $C_{18}$ column was from The Separations Group, Hesperia, Calif., USA. Pyrostase was obtained from Molecular Genetic Resources, Tampa, Fla., USA, and the nested deletion kit was from Pharmacia Biotech Inc. The messenger RNA isolation kit, the rabbit spleen Uni-ZAP library, Stratascript RNase H⁻ reverse transcriptase and cloned Pfu DNA polymerase were purchased from Stratagene, La Jolla, Calif., USA. T4 polynucleotide kinase, T4 DNA ligase, Klenow DNA polymerase, and restriction enzymes were from New England Biolabs Inc., Beverly, Mass., USA. The 5'-Amplifinder™ RACE kit was obtained from CLONETECH Laboratories, Inc., Palo Alto, Calif., USA, and the Sequenase Version 2.0 DNA sequencing kit was from United States Biochemical Corp., Cleveland, Ohio, USA. The Qiaprep spin kit and the plasmid midi kit were from Qiagen, Inc., Chatsworth, Calif., USA; the Geneclean kit was from BIO 101, Inc., Vista, Calif., USA. Expression clones for Rac1, Cdc42Hs, and RhoA as GST fusion proteins were generously provided by Dr. Channing Der (University of North Carolina, Chapel Hill, N.C., USA).

Purification and Analysis of PAK I Peptides—The inactive PAK I holoenzyme was purified to apparent homogeneity from rabbit reticulocytes by chromatography on DEAE-cellulose, SP-Sepharose, and protamine-agarose and by FPLC on Mono Q and Mono S as described in EXAMPLE 1, above. Peptides of PAK I were obtained by chemical cleavage using CNBr, partial proteolysis with trypsin, or by a combination of CNBr and endopeptidase Asp-N.

For in situ CNBr cleavage, PAK I was subjected to electrophoresis on a 12.5% SDS-polyacrylamide gel {Laemmli, U. K., *Nature,* 227:680–685 (1970)} and transferred to an Immobilon-P membrane. PAK I was cleaved on the membrane with 4 mg/ml CNBr for 15 h at room temperature and the peptides were eluted with 100 μl of 70% isopropyl alcohol and 1% trifluoroacetic acid for 3 h at room temperature, followed by 100 μl of 40% acetonitrile for 1 h at 37° C. The extracts and the original cleavage solution were dried in a Speed Vac concentrator and separated by electrophoresis on a 16.5% SDS-polyacrylamide gel. The peptides were transferred to a ProBlott membrane and subjected to amino acid sequence analysis. The N-terminal sequence of CNBr peptide 1 (20 kDa) was PEQWAR-LLGTSNXTKLEQKK (SEQ ID NO: 3), and that of CNBr peptide 2 (8 kDa) was XFSTGGKDPLSANHXL (SEQ ID NO: 4).

To obtain the amino-terminal sequence of the p37 peptide, PAK I was partially digested with 4 μg/ml trypsin on ice for 1 min, as described by Tahara and Traugh {Tahara, S. M., et al., *J. Biol. Chem.,* 256:11558–11564 (1981)}, with the omission of bovine serum albumin. Peptides were separated by electrophoresis on a 12% SDS-polyacrylamide gel and transferred to Immobilon-P, and the sequence was determined to be SVIDPIPAPVGDSHV (SEQ ID NO: 5).

For CNBr/endopeptidase Asp-N cleavage, PAK I was cleaved with 10 mg/ml CNBr for 15 h at room temperature, and the peptides were denatured, reduced, and carboxymethylated as described elsewhere {Stone, K. L., et al., *Techniques in Protein Chemistry,* Tony E. Hugli, ed., p. 377–390, Academic Press, San Diego (1989)}. The CNBr peptides were digested with endopeptidase Asp-N, and the digest was acidified with glacial acetic acid and separated by reverse phase high pressure liquid chromatography on a Vydac $C_{18}$ column with a acetonitrile gradient from 0 to 100%. Amino acid sequence analysis and mass spectrometry were performed by the Biotechnology Instrumentation Facility. The N-terminal sequences of six CNBr/endopeptidase Asp-N peptides were: CNBr/Asp-N peptide 1 (5,497 Da), DGFPSGAPALNTKVXETSAVVT (SEQ ID NO: 6); CNBr/Asp-N peptide 2 (4,319 Da), VEGEPPYL-NENPLRALYLIAT (SEQ ID NO: 7); CNBr/Asp-N peptide 3 (3,479 Da), DVALGQECAIKQINLQKQPKKELIIN (SEQ ID NO: 8); CNBr/Asp-N peptide 4 (3,479 Da), DVEKRGSAKELLQHPF (SEQ ID NO: 9); CNBr/Asp-N peptide 5 (3,226 Da), DEXQIAAVXREXKQAKEFKGAN-QVIHR (SEQ ID NO: 10); CNBr/Asp-N peptide 6 (1,438 Da), KELKNPNIVNF (SEQ ID NO: 11).

cDNA Cloning by Reverse Transcription and Polymerase Chain Reaction—Poly(A)⁺ RNA was isolated from rabbit liver, spleen, kidney and brain using the messenger RNA isolation kit. One μg of poly(A)⁺ RNA was reverse-transcribed with Stratascript RNase H⁻ reverse transcriptase using an oligo(dT) primer. The resulting cDNA was amplified over 35 cycles in a polymerase chain reaction {Mullis, K. B., et al., *Methods Enzymol.,* 155:335–350 (1987)} using Pyrostase, the 48-fold degenerate sense oligonucleotide primer (5'-ATGGAYGARCARCARATHGC-3') (1 μM)

(SEQ ID NO: 12), and the 512-fold degenerate antisense oligonucleotide primer (5'CCNCKYTTYTCNACRTCCAT-3') (5 μM) (SEQ ID NO: 13). A PCR product of 431 bp was subcloned into pBluescript SK+ from Stratagene, La Jolla, Calif., USA. In the foregoing sequences, R=A or G; Y=C or T; and N=A or C or G or T.

cDNA Library Screening—For high density screening in a rabbit spleen Uni-ZAP library, approximately 5×10$^5$ plaque-forming units were plated with Escherichia coli (E. coli) XL-1Blue. Two replicas were prepared from each plate on Hybond-N membranes. The 431-bp PAK I cDNA was labeled by the multipriming procedure {Feinberg, A. P., et al., Anal. Biochem., 136:6–13 (1983)} with [α-$^{32}$P]dCTP. Hybridization at 30° C. and washes at 55° C. were carried out as described elsewhere {Jakobi, R., et al., Eur. J. Biochem., 183:227–233 (1989)}. After autoradiography, positive clones were purified over two more rounds of screening, excised in vivo from the Uni-ZAP vector as pBluescript SK+ clones, and analyzed by Southern blot hybridization {Jakobi, R., et al., Eur. J Biochem., 183:227–233 (1989); and Southern, E. M., J. Mol. Biol., 98:503–517 (1975)}.

Cloning of the 5'-cDNA Region by RACE-PCR—The 5'-end of the PAK I cDNA was obtained by RACE-PCR using the 5'-Amplifinder™ RACE kit. Total RNA from rabbit spleen was isolated by the guanidinium thiocyanate method {Chirgwin, J. M., et al., Biochemistry, 18:5294–5299 (1979)}, and poly(A)+ RNA was isolated by two rounds of oligo(dT)-cellulose chromatography {Aviv, H., et al., PNSA (USA), 69:1408–1412 (1972)}. For the cDNA synthesis, poly(A)+ RNA (2 μg) was extended with reverse transcriptase using the oligonucleotide primer P1 (5'-GCCTGTAAACACTCTCTGCACACAG-3') (SEQ ID NO: 14). The synthesized cDNA was purified and ligated to a synthetic anchor. PCR was carried out over 35 cycles with cloned Pfu DNA polymerase using the oligonucleotide primer P2 (5'-CTTCATCCATGCAGGTTTCTGTTAC-3') (SEQ ID NO: 15) and a primer corresponding to the anchor sequence. A PCR product of approximately 1150 bp was subcloned into pBluescript SK+.

Sequence Analysis of PAK I cDNA Clones—Plasmid DNA was isolated with the plasmid midi kit; subclones were constructed using internal EcoRI and PstI sites, and nested deletions were created with the double-stranded nested deletion kit. DNA sequencing was carried out by the dideoxy chain termination method of Sanger, et al. {Sanger, F., et al., PNSA (USA), 74:5463–5467 (1977)} using [α-$^{35}$S]dATP and T7 DNA polymerase. Nucleotide sequences were aligned to form the full-length cDNA sequence, and the sequence was analyzed with the University of Wisconsin Genetics Computer Group Package Version 8 {Program Manual for the Wisconsin Package, Version 8, Sep. 1994, Genetics Computer Group, 575 Science Drive, Madison, Wis., USA 53711}.

Stimulation of PAK I Autophosphorylation and Activity by G-proteins—GST-fusion proteins of Rac1, Cdc42Hs and RhoA were expressed individually in E. coli DH5α; the bacteria were sonicated in the presence of the protease inhibitors aprotinin, leupeptin, pepstatin (40 μg/ml) and phenylmethylsulfonyl fluoride (0.5 mM), and the fusion proteins were purified on glutathione-Sepharose beads. GST-Rac1, GST-Cdc42Hs, or GST-RhoA (1 μg) was pre-loaded with 0.18 mM GTPγS or 0.18 mM GDP in 20 mM Tris-HCl, pH 7.5 and 50 mM NaCl for 10 min at 30° C. in a volume of 20 μl. Then, the G proteins were incubated with PAK I (0.1 μg) in 70 μl of phosphorylation buffer (50 mM Tris-HCl, pH 7.4, 10 mM MgCl$_2$, 30 mM 2-mercaptoethanol) with 0.2 mM [γ-$^{32}$P]ATP (4000 dpm/pmol) at 30° C. Aliquots were removed at 5, 10 and 15 min; autophosphorylation was analyzed by electrophoresis on a 12.5% SDS-polyacrylamide gel followed by autoradiography.

The effects of autophosphorylation on activity were measured by preincubation of G protein with PAK I for 10 min as described above. A 20-μl sample was assayed in a final volume of 70 μl containing phosphorylation buffer, 4.0 μg H4, and 0.2 mM [γ-$^{32}$P]ATP (2000 dpm/pmol), by incubation for 15 min at 30° C. Phosphorylation of H4 was analyzed by electrophoresis on a 15% SDS-polyacrylamide gel followed by autoradiography {Hathaway, G. M., et al., Methods Enzymol., 60:495–511 (1979)} and quantified by scintillation counting of the excised H4 band.

RESULTS

Preparation of a PAK I-specific Hybridization Probe—Peptides from the inactive PAK I holoenzyme purified from rabbit reticulocytes were obtained by cleavage with CNBr, CNBr/endopeptidase Asp-N, or trypsin. The peptides were separated, purified and partially sequenced as described under "Experimental Procedures". Two CNBr-peptides of 20 and 8 kDa and six CNBr/endopeptidase Asp-B peptides ranging from 5497 to 1438 Da were isolated. A peptide of 37 kDa, isolated following limited proteolysis with trypsin, contained the active catalytic domain (EXAMPLE 1, above). All nine peptides were subjected to partial sequence analysis as described under "Experimental Procedures". The N-terminal sequences of CNBr/Asp-N peptides 2–5 could be located within the alignment of the catalytic domains of other protein kinases as described by Hanks, et al. {Hanks, S. K., et al. Science, 241:42–52 (1988); and Hanks, S. K., et al., Methods Enzymol., 200:38–62 (1991)}.

Following reverse transcription of mRNA from rabbit spleen and brain, degenerate oligonucleotides corresponding to CNBr/Asp-N peptides 4 and 5 were used to amplify a PAK I-specific polynucleotide. After 35 cycles of amplification, PCR products of 431 bp were subcloned and analyzed by DNA sequencing. The clones from spleen and brain were identical and contained the complete amino acid sequences of CNBr/Asp-N peptides 2, 4 and 5.

Cloning of the cDNA Encoding PAK I—The partial 431-bp cDNA from rabbit spleen was used to screen a rabbit spleen cDNA library and nine clones were detected within 5×10$^5$ plaques. Restriction analysis and partial cDNA sequencing showed that all nine clones contained the same open reading frame, but were incomplete at the 5'-end. Differences in the length of the 3'-untranslated region were observed. PAKI-4.1 was the clone that contained the longest open reading frame and had the longest 3'-untranslated region (FIG. 9).

The 5'-end of the cDNA for PAK I was obtained by RACE-PCR from rabbit spleen mRNA. Six positive clones with an insert of approximately 1150 bp were characterized by restriction analysis and partial DNA sequencing. All clones overlapped with the 5'-end of PAKI-4.1 and contained the same open reading frame starting with ATG; only the lengths of the 5'-untranslated region were different. The longest clone isolated by RACE-PCR (1150-4) contained the longest 5'-untranslated region.

Complete Sequence Analysis of PAK I cDNA—FIG. 9 shows the strategy for cloning and sequencing of PAK I cDNA. A restriction map for the entire PAK I cDNA is shown at the top, and clones chosen for the complete sequence analysis by nested deletions are indicated below.

Arrowheads show the directions and the positions sequenced by nested deletions. Boxes represent the open reading frame for PAK I, and solid lines represent untranslated regions. Endonuclease cleavage sites indicated are: E, EcoRI; D, DraI; H, HindIII; P, PstI; S, SacI; X, XhoI. Sites in parentheses are within synthetic linkers. Both strands of the library clone PAKI-4.1 and the RACE-PCR clone 1150-4 were sequenced completely. For the sequence analysis of PAKI-4.1, subclones E1100 and P2900 were constructed using internal EcoRI and PstI sites (FIG. 9). Overlapping nested deletions were created to sequence 2665 nucleotides from the 3'-end of the noncoding strand of PAKI-4.1, the entire coding strand of subclone P2900, and both entire strands of subclone E1100 and of RACE-PCR clone 1150-4.

The complete cDNA sequence of PAK I consists of 4471 bp including a poly(A) tail of 18 nucleotides (FIG. 1). The nucleotide sequence has been submitted to the GenBank™/EMBL Data Bank with accession number U46915). FIG. 1 shows the nucleotide and deduced amino acid sequence of rabbit PAK I. The sequence of the coding strand of PAK I cDNA is shown in a 5' to 3' orientation and extends over 4471 nucleotides including 18 nucleotides of the poly(A) tail. The cDNA sequence contains an open reading frame from nucleotide 74 to nucleotide 1645, 73 nucleotides of 5'-untranslated region, and 2826 nucleotides of 3'-untranslated region. The 3'-untranslated regions of other clones isolated by screening of the rabbit spleen library were shorter than that of PAKI-4.1, but could be aligned without mismatches within the complete cDNA sequence and ended with poly(A) tails. The 3'-untranslated region of clone PAKI-7.3 was 1055 nucleotides, including a poly(A) tail of 20 nucleotides; those of clones PAKI-3.1 and PAKI-10.1 were 2478 nucleotides, including a poly(A) tail of 19 nucleotides, as indicated in FIG. 1. The 3' ends of the shorter clones, PAKI-7.3 at nucleotide 2698 and PAKI-3.1/PAKI-10.1 at nucleotide 4122, are indicated by the (↑) and possible poly(A) addition signals are underlined.

These results suggest that the different clones represent alternative transcription stops. The poly(A) addition signal for PAKI-7.3 could be AATAAT (20 nucleotides 5' of the poly(A) tail) and the poly(A) addition signal for PAKI-3.1/PAKI-10.1 could be AATTAAA (17 nucleotides 5' of the poly(A) tail) (FIG. 1). No sequence similar to the typical poly(A) addition signal (AATAAA) precedes the poly(A) tail of PAKI-4.1.

The deduced amino acid of the open reading frame is shown below the nucleotide sequence in single letter code. It consists of 524 amino acid residues with a calculated molecular weight of 58.027. Amino acid sequences determined by microsequencing of PAK I peptides are underlined. From the N-terminus to the C-terminus, the peptides are as follows: CNBr peptide 2, CNBr peptide 1, CNBr/ASP-N peptide 1, p37, CNBr/ASP-N peptide 3, CNBr/ASP-N peptide 6, CNBr/ASP-N peptide 5, CNBr/ASP-N peptide 2 and CNBr/ASP-N peptide 4.

All nine partial amino acid sequences, obtained by microsequence analysis of purified peptides of PAK I, could be aligned within the deduced amino acid sequence (FIG. 1). The peptide beginning with SVID at residue 197 indicates the N terminus of the p37 peptide generated by limited trypsin digestion (first ↑), which contains the catalytic domain and a portion of the regulatory domain (EXAMPLE 1, above). The beginning of the catalytic domain at residue 247 (second ↑) was determined by comparison with the sequences of other protein kinases using the alignment of Hanks, et al. {*Science*, 241:42–52 (1988); and *Methods Enzymol.*, 200:38–62 (1991)}. Peptide p37 contains part of the regulatory domain (from residues 197 to 246) and all 11 conserved subdomains characteristic of the catalytic domain of protein kinases. The GXGXXG motif involved in nucleotide binding begins at residue 256; residue 278 is the invariant lysine that contacts the α- and β-phosphates of the ATP; residue 368 is the aspartate that acts as a general base for the removal of a proton from the hydroxyl group of the protein substrate; residue 370 is the lysine that binds to the γ-phosphate of the ATP; and residue 386 is the aspartate that is part of the conserved DFG motif and chelates the $Mg^{2+}$ bound to the ATP. A putative binding site for Rho-like G proteins was identified in the regulatory domain between residues 73 and 107 by sequence comparison with PAK65 from rat brain and human placenta and yeast STE20 {Manser, E., et al., *Nature*, 367:40–46 (1994); Martin, G. A., et al., *EMBO J.*, 14:1970–1978 (1995); Leberer, E., et al., *EMBO J.*, 11:4815–4824 (1992); and Ramer, S. W., et al., *PNSA* (USA), 90:452–456 (1993)}.

The deduced amino acid sequences of rabbit PAK I, human PAK65, rat PAK65 and the GTP/p21-binding and catalytic domains of yeast STE20 were aligned using the programs Pileup, Lineup, and Pretty of the University of Wisconsin Genetics Computer Group Package Version 8 {Program Manual for the Wisconsin Package, Version 8, Sep. 1994, Genetics Computer Group, 575 Science Drive, Madison, Wis., USA 53711}. The consensus sequence indicates when identical residues are present in at least three of the protein sequences; deviations from the consensus sequence are indicated by lower case letters; gaps are indicated by dots (FIG. 10). The positions of the conserved eleven subdomains of the catalytic domain of the protein kinases are shown below the alignment in Roman numerals. Amino acid sequence alignment of the total proteins revealed 95% identity between rabbit PAK I and human PAK65 and 78% identity between rabbit PAK I and rat PAK65. Within the catalytic domain, rabbit PAK I has 99% identity with human PAK65, 92% with rat PAK65 and 65% with yeast STE20. In the regulatory domain, PAK I has significantly less homology with STE20 and rat PAK65, except for the G protein-binding region. Compared to rat PAK65, PAK I was 20 residues shorter because of five gaps in the regulatory domain ranging from 1 to 10 residues. Human PAK65 was 18 residues shorter than rabbit PAK I because of differences at the N-terminus over the first 30 amino acid residues; the rest of the amino acid sequence was very similar to rabbit PAK I. FIG. 10 also compares two additional sequences in the GenBank (human lymphocyte PAK1 and PAK2 with GenBank Accession Nos. U24152 and U24153, respectively). The human PAK1 has 2318 nucleotides and the human PAK2 has 2019 nucleotides. Preliminary information shows that the amino acid sequence of rabbit PAK I has 97.137% identity with that of human PAK2; the rabbit PAK I nucleotide sequence's coding region shares 91.858% homology with the human PAK2's coding region; and the total nucleotide sequences of the rabbit PAK I and human PAK2 are matched at 86.983%. The other protein kinases which are homologous to rabbit PAK I and not compared in FIG. 10 are: yeast SHK1 {Marcus, S., et al., *PNAS* (USA), 92:6180–6184 (1995)}, yeast PAK1Sp {Ottilie, S., et al., *EMBO J.*, 14:5908–5919 (1995)}, and mouse PAK3 {Bagrodia, S., et al., *J. Biol. Chem.*, 270(39) :22731–22737 (1995)}.

G Protein Activation of PAK I—Previously, a number of compounds known to modulate protein kinase activity have been examined as possible physiological regulators of PAK I; none of these had any effect on PAK I activity. To examine the effects of the G proteins Rac1, Cdc42Hs and RhoA on autophosphorylation and activation of purified inactive PAK I, GST fusion proteins expressed in E. coli were purified on glutathione-Sepharose beads and preloaded with GTPγS. PAK I (0.1 μg) was incubated with [γ-$^{32}$P]ATP for the times indicated, alone or in the presence of the GST-fusion proteins of Rac1, Cdc42Hs or RhoA bound to GTPS. Autophosphorylation was analyzed by SDS-polyacrylamide gel electrophoresis followed by autoradiography. The autoradiogram is shown in FIG. 11.

A low basal level of autophosphorylation of inactive PAK I was detected in the absence of G protein (FIG. 11). Upon addition of GST-Rac1, a slight stimulation of autophosphorylation over the basal level was observed over a 15-min period of incubation, while GST-RhoA had little effect. Stimulation of autophosphorylation upon addition of GST-Cdc42Hs was observed within 5 min. The rate of autophosphorylation was linear up to 10 min and began to level off by 15 min.

To examine the effects of autophosphorylation on activation of PAK I, protein kinase activity was measured by phosphorylation of the substrate H4 (FIG. 12). PAK I (0.1 μg) was incubated under autophosphorylation conditions for 10 min, either alone or with GST-Rac1, GST-Cdc42Hs or GST-RhoA preloaded with GTPγS or GDP, then assayed with H4. Following autophosphorylation, assays with H4 were carried out and analyzed on a 15% SDS-polyacrylamide gel, followed by autoradiography and scintillation counting of the excised H4 bands. Phosphorylation of H4 in the absence of G protein was used as background and subtracted from the data. Phosphorylation of H4 was dependent on the level of autophosphorylation of PAK I. Without addition of G protein, a low level of autophosphorylation and PAK I activity with H4 was observed, which was subtracted from the data obtained in the presence of G protein. Addition of GST-Cdc42Hs (GTPγS) resulted in an increased autophosphorylation of PAK I of 0.97 mol/mol and a stimulation of the rate of phosphorylation of H4 of 18,261 pmol/min/mg. With GST-Cdc42Hs(GDP), stimulation of autophosphorylation was 0.12 mol/mol, and the activity was 2,154 pmol/min/mg. These values were approximately 8-fold lower than those observed with Cdc42Hs(GTPγS). GST-Rac1(GTPγS) resulted in only a modest stimulation, approximately 10-fold lower than that observed with Cdc42Hs(GTPγS); autophosphorylation and activity were 0.09 mol/mol and 1515 pmol/min/mg, respectively. GST-TRhoA(GTPγS) had no stimulatory effect on either autophosphorylation or activity.

DISCUSSION

The cDNA isolated by screening of a rabbit spleen cDNA library and by 5'-RACE-PCR using rabbit spleen mRNA contains the information for the complete sequence of PAK I. The deduced amino acid sequence contains the catalytic domain and a N-terminal regulatory domain, including a region shown previously to bind Rho-like G proteins. All of the partial amino acid sequences determined by microsequencing of nine peptides from PAK I could be aligned with the deduced amino acid sequence. The calculated molecular mass of 58,027 Da is in accordance with the apparent molecular mass of 58–60 kDa displayed by native PAK I in SDS-polyacrylamide gels (EXAMPLES 1 and 2).

The cDNA for PAK I from rabbit spleen contains a long 3'-untranslated region of 2826 nucleotides. Long 3'-untranslated regions are characteristic of highly regulated genes and are involved in the stability and translational efficiency of the mRNA {Jackson, R. J. (1993) Cell, 74:9–14 (1993); and Wormington, M., BioEssay, 16:533–535 (1994)}. The isolation of PAK I clones from rabbit spleen with shorter 3'-untranslated regions of 1055 and 2478 nucleotides, including the poly(A) tails, suggests the existence of different transcripts for PAK I generated by alternative transcription termination and polyadenylation sites. Transcripts of PAK I with 3'-untranslated regions of different lengths could have different stability and/or translation efficiency. Therefore, the amount of PAK I protein could be regulated in part by the expression of transcripts with 3'-untranslated regions of different lengths.

Sequence comparison shows high sequence homology with the yeast protein kinase STE20 {Leberer, E., et al., EMBO J, 11:4815–4824 (1992); and Ramer, S. W., et al., PNSA (USA), 90:452–456 (1993)} and PAK65 from rat brain and human placenta {Manser, E., et al., Nature, 367:40–46 (1994); and Martin, G. A, et al., EMBO J., 14:1970–1978 (1995)}, suggesting that they belong to a family of related protein kinases. Rat PAK65 appears to be a brain-specific isoform; a protein with the corresponding molecular mass was detected only in brain extracts, but not in other tissues by overlay assays with radiolabeled Rac1 (GTP) and Cdc42Hs(GTP) and by a specific antibody raised against the N-terminal region of rat brain PAK65 {Manser, E., et al., Nature, 367:40–46 (1994); and Martin, G. A., et al., EMBO J, 14:1970–1978 (1995)}. Unlike the brain-specific rat PAK65, inactive PAK I was present in a number of tissue and cell types, and purified from rabbit reticulocytes (EXAMPLE 1, above), and partially purified from liver and skeletal muscle; chicken gizzard, liver and brain; bovine liver; mouse 3T3-L1 cells {Tahara, S. M., et al., J. Biol. Chem., 256:11558–11564 (1981); Tahara, S. M., et al., Eur. J. Biochem., 126:395–399 (1982); Tuazon, P. T., et al., Eur. J Biochem., 129:205–209 (1982); Tuazon, P. T., et al., J. Biol. Chem., 259:541–546 (1984); and EXAMPLE 2, above}, and frog oocytes, early zygotes, and embryos (EXAMPLE 2, above). The protein reacted with antibodies raised against PAK I from rabbit reticulocytes. PAK I from rabbit spleen and PAK65 from human placenta have a high degree of sequence homology, but the N-terminal 30 amino acid residues are completely different. Human PAK65 lacks 18 amino acid residues and the remaining 12 amino acid residues cannot be aligned with either rabbit PAK I or rat PAK65. Therefore, it is unlikely that the two protein kinases are homologous enzymes, but appear to be closely related isoforms.

PAK65 from rat brain and human placenta as well as two additional PAK enzymes detected in human neutrophils were shown to be autophosphorylated upon binding of the G proteins Rac1 and Cdc42, but not RhoA; autophosphorylation resulted in activation as shown by stimulation of phosphorylation of the universal substrate, myelin basic protein {Manser, E., et al., Nature, 367:40–46 (1994); Martin, G. A., et al., EMBO J., 14:1970–1978 (1995); Knaus, U. G., et al., Science, 269:221–223 (1995); and Prigmore, E., et al., J. Biol. Chem., 270:10717–10722 (1995)}. Binding of the GTP-bound form of GST-Cdc42Hs, but not GST-Rac1 or GST-RhoA, greatly induced autophosphorylation of PAK I from rabbit reticulocytes, and autophosphorylation resulted in activation of the protein kinase.

STE20 in budding yeast plays a key role in signal transduction pathways connecting membrane receptors with the MAP kinase cascade {Herskowitz, I., Cell, 80:187–197 (1995)}. In the mating differentiation pathway, a pheromone initiates differentiation by activation of STE20, which activates the MAP kinase cascade. STE20 and MAP kinases are also involved in other signal transduction pathways in yeast, including the invasive growth response and the pseudohyphal development pathways initiated by nutritional starvation. Different isoforms of STE20 and MAP kinases could have alternative functions in regulating different signal transduction pathways {Herskowitz, I., *Cell,* 80:187–197 (1995)}. PAK I and other PAK enzymes, as the mammalian counterparts of yeast STE20 protein kinases, also appear to be involved in the coordination of signal transduction pathways. It has recently been hypothesized {Minden, A., et al., *Cell,* 81:1147–1157 (1995); and Coso, O. A., et al., *Cell,* 81:1137–1146 (1995)} that the Racl/Cdc42 regulated PAK enzymes are a key point regulator of the stress-activated protein kinase (SAPK) or Jun kinase (JNK) signaling pathway, which regulates the c-Jun activity. Biochemical evidence from our laboratory suggests PAK I is involved in regulation of cytostasis as shown by the high level of activity in quiescent and serum-starved cells and lower levels of PAK I activity in actively dividing cells (EXAMPLE 2, above). PAK I activity is also high in mature frog oocytes, but is greatly diminished following fertilization (EXAMPLE 2, above). Injection of active PAK I into 2-cell embryos has been shown to inhibit cell division in the injected blastomere. Thus, PAK I appears to be a candidate for regulation of the signaling cascade which is activated in response to stress.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allows for obvious changes in the basic invention herein are also within the claims.

---

We claim:

1. A method of suppressing cell division in a patient, said method comprising the steps of administering to the patient an effective amount of a composition comprising a substantially pure cytostatic protein kinase, wherein said cytostatic protein kinase is selected from the group consisting of: endogenously active PAK I, proteolytically-activated PAK I, and autophosphorylated PAK I, wherein said effective amount suppresses cell division and cleavage.

2. A method according to claim 1 wherein the cytostatic protein kinase is proteolytically activated and autophosphorylated PAK 1.

3. A method according to claim 1 wherein the PAK I is selected from the group consisting of rabbit PAK I, frog PAK I, 3T3-L1 PAK I, human PAK2, human PAK65, human PAK1, rat PAK65, and mouse PAK3.

4. A method according to claim 3, wherein the PAK I is rabbit PAK I.

5. A method according to claim 1, wherein the cystostatic protein kinase is proteolytically activated PAK1, said proteolytically activated PAK I being p37.

6. A method according to claim 1, wherein said p37 consists essentially of amino acids 197 to 524 of SEQ ID NO:2.

7. A method according to claim 1 wherein the cytostatic protein kinase comprises an active catalytic domain.

8. A method according to claim 7, said active catalytic domain consisting essential of amino acids 247 to 524 of SEQ ID NO:2.

9. A method according to claim 7 wherein the cytostatic protein kinase has a phosphorylated threonine.

10. A method according to claim 4 wherein the PAK I comprises an amino acid sequence selected from the group consisting of SEQ ID NO:2, amino acids 197 to 524 of SEQ ID NO:2, and amino acids 247 to 524 of SEQ ID NO:2.

11. A method according to claim 1 wherein said administering step introduces at least about 0.01 pg of PAK I per cell.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 4471 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

```
GGGAGCTCGG  ACGGAGGCGC  CTCGCCGGGG  CGGGGACCTT  TCCTCGCCTG  GGGTCATTTC     60
ATAACTCTGA  ATCATGTCTG  ATAACGGAGA  ACTGGAAGAC  AAGCCTCCAG  CACCTCCTGT    120
GCGAATGAGC  AGCACCATCT  TTAGCACTGG  AGGCAAAGAC  CCCTTGTCAG  CCAATCACAG    180
CTTGAAGCCT  TTGCCCTCTG  TTCCAGAAGA  AAAAAAGCCA  AGGAATAAAA  TCATCTCCAT    240
ATTCTCAGGC  ACAGAAAAAG  GAAGTAAAAA  GAAAGAAAAA  GAACGACCAG  AGATTTCTCC    300
TCCCTCTGAT  TTTGAGCACA  CCATCCACGT  CGGCTTCGAT  GCTGTTACTG  GAGAATTCAC    360
CGGCATGCCG  GAGCAGTGGG  CACGCCTGCT  GCAGACGTCC  AACATCACCA  AACTCGAGCA    420
GAAGAAGAAC  CCACAGGCAG  TGCTGGACGT  GCTCAAGTTC  TATGACTCCA  ACACCGTGAA    480
GCAGAAGTAC  CTGAGCTTCA  CTCCTCCGGA  GAAAGATGGC  TTCCCTTCTG  GAGCACCAGC    540
ACTGAATACC  AAGGTATCAG  AAACATCAGC  AGTAGTAACA  GAAGAAGATG  ACGATGACGA    600
AGAGGCGGCA  CCTCCTGTTA  TTGCCCCACG  GCCAGATCAT  ACAAAATCAA  TTTATACACG    660
GTCTGTAATT  GACCCTATTC  CTGCACCAGT  TGGTGATTCT  CATGTTGATA  GTGGTGCCAA    720
GTCTTCAGAT  AAACAGAAAA  AGAAAACCAA  GATGACAGAT  GAAGAGATTA  TGGAGAAATT    780
ACGAACTATT  GTGAGCATAG  GTGACCCTAA  GAAAAAATAT  ACAAGATATG  AAAAAATTGG    840
ACAAGGGCT   TCTGGTACAG  TTTTCACTGC  TACTGATGTG  GCATTGGGAC  AGGAGGTTGC    900
TATCAAACAG  ATTAATTTAC  AGAAACAGCC  AAAGAAGGAA  TTGATCATTA  ATGAAATTCT    960
GGTGATGAAA  GAGTTAAAAA  ATCCCAACAT  AGTTAACTTC  TTGGACAGTT  ACCTAGTGGG   1020
```

```
AGATGAATTA  TTCGTGGTAA  TGGAGTACCT  TGCTGGTGGC  TCACTTACTG  ATGTTGTAAC   1080

AGAAACCTGC  ATGGATGAAG  CGCAGATTGC  AGCTGTGTGC  AGAGAGTGTT  TACAGGCTTT   1140

GGAGTTTTTA  CATGCTAATC  AAGTGATCCA  CAGAGACATC  AAAAGTGACA  ATGTGCTTTT   1200

GGGGATGGAA  GGATCAGTTA  AACTTACTGA  CTTTGGTTTC  TGTGCCCAGA  TCACCCCTGA   1260

GCAGAGTAAA  CGCAGTACCA  TGGTTGGAAC  GCCTTACTGG  ATGGCACCCG  AGGTGGTTAC   1320

ACGGAAAGCA  TATGGCCCTA  AAGTCGACAT  ATGGTCTCTG  GGCATCATGG  CTATTGAGAT   1380

GGTAGAAGGA  GAACCTCCAT  ACCTCAATGA  AAATCCCTTG  AGGGCCTTGT  ACCTGATAGC   1440

AACTAATGGA  ACCCCAGAAC  TTCAGAATCC  AGAGAAGCTT  TCCCCCATAT  TTCGGGATTT   1500

CTTAAATCGA  TGTTTGGAAA  TGGATGTGGA  GAAGAGAGGT  TCAGCCAAAG  AACTGCTGCA   1560

GCATCCCTTC  CTGAAACTGG  CCAAACCATT  ATCCAGCTTG  ACACCACTCA  TCATGGCAGC   1620

TAAAGAAGCA  ATGAAGAGTA  ACCGCTAACA  TCAGTGCCGT  GGCCTCATGT  TCCTTTGTCC   1680

ATTTCCTAAA  AGAAGTCTTT  TAATATATGA  AAGTTACTGC  TCTTTTCGGG  GTTTAAAGAA   1740

ATGGTCTGAA  TAATGGAGGA  AAAACAAAGC  TACTATTTCT  TGAAGACAAC  TAAGACAAAA   1800

TTGCAAAAAG  AGAATCATGA  CTTTCAGATG  AACCCCTTCT  TTAGGGTCCA  AAGGAATTGT   1860

GGACTGAGTC  ACTCGCCTTA  CATCTTTCAG  CAGACAGCCG  TCAGGACTTG  TTCCTTATGC   1920

TTGAGATTTG  CATTTTATTT  TGCTAACTTT  GTTGGAATAG  ATCCCATTCT  TGTCCCCTTT   1980

GGGGTGTTTT  CAATACTTGA  AGGGCAGATT  CGAGTTTTTC  AGCATATTTG  TTTCACCTGC   2040

TGGTCTTCTC  TCTCCTTCAG  AGCTCTCCTT  TTCCTCGACT  TGCTCCTTTT  GAGTTGCTTT   2100

GAGAACTTTT  TGTCGTGCCT  GAATTCAAGG  CAAGTATGAT  AGAAATTGTG  CAGCTCCTCA   2160

TTGGCAAAGG  AGCTCAGCAT  AGTTTAACTT  TGTATAGAAG  TTAGGACCAG  CAATGGTTTC   2220

ATGGAATATT  TCAGTTCAGA  ACTTGAACTG  AAAGAAGGGA  AGAAAAGTAT  GTGATTTTTA   2280

CCTTTTTAAC  AAATGTGAAA  GGGTCACTTT  GAGAAATCTC  ATGGTGGTGA  GTTTGGAGTT   2340

TGTTACATGT  ATAGAAAGAA  GACTAATCTA  TATTTATAAC  TAAAATCACT  GAGACAAAAA   2400

AGAATCCCGG  CGACTGTACA  CCTGACGGTT  TTGTCTTCCT  TTCTGCCTTT  CTCCTCTTCA   2460

GATTTGGCTT  GAGGAGGAAC  CAAAGTGATT  TTTCTTGTTC  CAGCTTGGGC  TTTATGACTG   2520

GTTAGTGCCA  TTACCTTTCC  TTTCCTCCTT  TCCTCTTTCA  TTTTGGAAAT  AAGTTTCTGT   2580

ATATGTTGCA  ATTTTAGGTT  TAGTTTTTTT  GTTTTGTTT   TTATGTAACC  CTCTCACCTT   2640

ACATATCCTG  TTCATACCAC  ATCCTACTCT  GTAATAATCA  TTGAATTTTC  AGAATTTGAA   2700

AATTAACTTT  TGTTTTCCAC  TTAAAGGGAA  AAATATTTGG  GGTTAGCAGA  GACAAAGTGA   2760

GAGATTGAAC  TTTAGTGAGT  TGTAGAATAA  TTAGTTGAGA  CTGTATTCAT  GAGAGAGAAA   2820

TGTCAGTATT  ACAGAGTTCC  AAATGATGAC  GAGTAAACTG  TAAAGGCTGT  CATAAGTTAG   2880

AGTGATTCTA  ACACATTACC  AGTGTGTTAC  TGTGTAAGAG  AACTTAAATG  AGAAGGTTCT   2940

TGGTGGATTC  ACGGATCATT  GGAGATGTGG  AATTACTTTA  GTATTTTTT   TTTTTTTCAG   3000

AGAAGTAGAG  AATATTCATG  TAAAAATCTG  AGGAAAAGAA  AAATGCGGTA  TTGATAGGAA   3060

TCCTTTTTTA  TTTTAAAGAT  TAAGAAAAGG  TCTGTGACCT  GTTAATTATG  AGAATGCCCC   3120

TTCCTCCCCT  TCCCTTCTGT  GCTTTACTCT  CCTGTTCTTC  TCTCCTCATT  TCTCGGTTGT   3180

TTGGCTTTTG  GGTGAGGAAT  GGTCTACTCT  GACATGCCTT  GAACCACATA  AAAAGTCTT   3240

CGGTTGAGTT  CTGGTATTTT  GTTCCCACCA  TGCCCTCCCA  GTGAAATTCA  CACCTGCTTG   3300

CCATCCTGCA  ATAGTACAAA  TCATTAATGA  AAATAAGTAT  GCTGTTTTGT  AGTATATTGG   3360

AAAACCAGCA  GAGTTTTATT  TCCTGTTATT  CCCGTCGTAT  CTGTGTTAAG  ACACAGATAT   3420
```

| | | | | | |
|---|---|---|---|---|---|
| CAGTGTAGAA | TGACTATTTT | GTGTTGATAC | CACAGAAAGA | TTTTCAGAAA | AATGAGTAAA | 3480
| ATAATTAATG | AAACTTTTAT | ATAGAGCACT | TAATGATCTC | TGATACCAGT | ATGGTTCTTG | 3540
| ATTGCATTTT | TCTCTGGACT | ATATTGGCCT | TCTACAGCTC | TTACTAAATT | ATAGAAACAA | 3600
| GCTGGTTTAT | TTCTGGTGGA | AAGCTACAGT | GCCCCTTAAC | TTCCAGATTT | GAGCACTCTT | 3660
| TGTAGACGAT | TGGATGGATG | GATCATGATG | AAGATGCTGC | CAATGAGAGA | GAGAGAAAAC | 3720
| ACCGACTAGA | TGATGAGACT | GATCATCATG | ACCACTTAAG | AAGGCGCTTC | CCATCCTAAG | 3780
| TCATAAGGAC | TTTTTCCCTC | GAATCTGTGC | CAGGGCCCCA | GTTTATGCTT | GTGGTGACAA | 3840
| CAAAGGGCCT | TTCAGACGGT | GGAAGCAGTT | TGGGATTTGT | ATTTACAGCC | TCTCGGATGG | 3900
| TTACCTGCAC | GTCCATTGCT | GGCAACGGAC | TTTGAAATCT | GACTCCTTGG | TTAAGGGAGC | 3960
| TACACTGTGG | TGTATTCTTT | ACTTACCTGG | ATAAACTAAC | CTGTAATAGA | AGTATACTTT | 4020
| AGTAAATTCT | GAAATGTGTC | ATTTTAAAC | AAAATAATCC | TGAAAGCAAT | ATGAAATTGT | 4080
| GATTTATTAG | TTATTTAAA | TTAAAATGTT | CAGATCTTCT | TGAAAGAACT | ACTGTATCTG | 4140
| AATCAAGATT | CTTGTTTTTT | AATAATTGCT | TTTTATATTC | ATCTTTTTT | GTCACCACTT | 4200
| CAGGGTGAAA | ATTCCCATTT | AAATCTGAAA | ATTACGTTAG | TCATCTTGTA | TTACTAGGGC | 4260
| AATATTACTG | TAATACTTAT | TTATGATATT | TTAACCTCTC | TGGTGGTCTT | TAAGTTATCT | 4320
| TCTACTCTTG | TTCCTTGTGC | TGCTTTAAGG | GACAGCTAAA | AACTGGGAAA | CCATGACAAT | 4380
| ATTGGAACAT | TTTATGCTAC | CTACAGTAGT | AAACAAGTAG | AGTGATTATG | TAACATGACC | 4440
| TCAAGGCTGA | CACAAAAAAA | AAAAAAAAA | A | | | 4471

( 2 ) INFORMATION FOR SEQ ID NO:2:

( i ) SEQUENCE CHARACTERISTICS:
        ( A ) LENGTH: 524 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

| Met | Ser | Asp | Asn | Gly | Glu | Leu | Glu | Asp | Lys | Pro | Pro | Ala | Pro | Pro | Val | Arg |
| 1 | | | | 5 | | | | | 10 | | | | | 15 | | |
| Met | Ser | Ser | Thr | Ile | Phe | Ser | Thr | Gly | Gly | Lys | Asp | Pro | Leu | Ser | Ala | Asn |
| | | | 20 | | | | 25 | | | | | 30 | | | | |
| His | Ser | Leu | Lys | Pro | Leu | Pro | Ser | Val | Pro | Glu | Glu | Lys | Lys | Pro | Arg | Asn |
| 35 | | | | | 40 | | | | 45 | | | | | 50 | | |
| Lys | Ile | Ile | Ser | Ile | Phe | Ser | Gly | Thr | Glu | Lys | Gly | Ser | Lys | Lys | Lys | Glu |
| | | | 55 | | | | | 60 | | | | | 65 | | | |
| Lys | Glu | Arg | Pro | Glu | Ile | Ser | Pro | Pro | Ser | Asp | Phe | Glu | His | Thr | Ile | His |
| | 70 | | | | | 75 | | | | | 80 | | | | | 85 |
| Val | Gly | Phe | Asp | Ala | Val | Thr | Gly | Glu | Phe | Thr | Gly | Met | Pro | Glu | Gln | Trp |
| | | | | 90 | | | | | 95 | | | | | 100 | | |
| Ala | Arg | Leu | Leu | Gln | Thr | Ser | Asn | Ile | Thr | Lys | Leu | Glu | Gln | Lys | Lys | Asn |
| | | | 105 | | | | | 110 | | | | | 115 | | | |
| Pro | Gln | Ala | Val | Leu | Asp | Val | Leu | Lys | Phe | Tyr | Asp | Ser | Asn | Thr | Val | Lys |
| 120 | | | | | 125 | | | | | 130 | | | | | 135 | |
| Gln | Lys | Tyr | Leu | Ser | Phe | Thr | Pro | Pro | Glu | Lys | Asp | Gly | Phe | Pro | Ser | Gly |
| | | | 140 | | | | | 145 | | | | | 150 | | | |

| | | | | | | | | | | | | | | |
|---|---|---|---|---|---|---|---|---|---|---|---|---|---|---|
| Ala | Pro | Ala | Leu | Asn | Thr | Lys | Val | Ser | Glu | Thr | Ser | Ala | Val | Val | Thr | Glu |
| | 155 | | | | | 160 | | | | 165 | | | | | | 170 |
| Glu | Asp | Asp | Asp | Asp | Glu | Glu | Ala | Ala | Pro | Val | Ile | Ala | Pro | Arg | Pro |
| | | | | 175 | | | | | 180 | | | | 185 | | |
| Asp | His | Thr | Lys | Ser | Ile | Tyr | Thr | Arg | Ser | Val | Ile | Asp | Pro | Ile | Pro | Ala |
| | | 190 | | | | | 195 | | | | | 200 | | | | |
| Pro | Val | Gly | Asp | Ser | His | Val | Asp | Ser | Gly | Ala | Lys | Ser | Ser | Asp | Lys | Gln |
| 205 | | | | | 210 | | | | | 215 | | | | | 220 | |
| Lys | Lys | Lys | Thr | Lys | Met | Thr | Asp | Glu | Glu | Ile | Met | Glu | Lys | Leu | Arg | Thr |
| | | | 225 | | | | | 230 | | | | | 235 | | | |
| Ile | Val | Ser | Ile | Gly | Asp | Pro | Lys | Lys | Lys | Tyr | Thr | Arg | Tyr | Glu | Lys | Ile |
| | 240 | | | | | 245 | | | | | 250 | | | | | 255 |
| Gly | Gln | Gly | Ala | Ser | Gly | Thr | Val | Phe | Thr | Ala | Thr | Asp | Val | Ala | Leu | Gly |
| | | | | 260 | | | | | 265 | | | | | 270 | | |
| Gln | Glu | Val | Ala | Ile | Lys | Gln | Ile | Asn | Leu | Gln | Lys | Gln | Pro | Lys | Lys | Glu |
| | | | 275 | | | | | 280 | | | | | 285 | | | |
| Leu | Ile | Ile | Asn | Glu | Ile | Leu | Val | Met | Lys | Glu | Leu | Lys | Asn | Pro | Asn | Ile |
| 290 | | | | | 295 | | | | | 300 | | | | | 305 | |
| Val | Asn | Phe | Leu | Asp | Ser | Tyr | Leu | Val | Gly | Asp | Glu | Leu | Phe | Val | Val | Met |
| | | | 310 | | | | | 315 | | | | | 320 | | | |
| Glu | Tyr | Leu | Ala | Gly | Gly | Ser | Leu | Thr | Asp | Val | Val | Thr | Glu | Thr | Cys | Met |
| | 325 | | | | | 330 | | | | | 335 | | | | | 340 |
| Asp | Glu | Ala | Gln | Ile | Ala | Ala | Val | Cys | Arg | Glu | Cys | Leu | Gln | Ala | Leu | Glu |
| | | | | 345 | | | | | 350 | | | | | 355 | | |
| Phe | Leu | His | Ala | Asn | Gln | Val | Ile | His | Arg | Asp | Ile | Lys | Ser | Asp | Asn | Val |
| | | | 360 | | | | | 365 | | | | | 370 | | | |
| Leu | Leu | Gly | Met | Glu | Gly | Ser | Val | Lys | Leu | Thr | Asp | Phe | Gly | Phe | Cys | Ala |
| 375 | | | | | 380 | | | | | 385 | | | | | 390 | |
| Gln | Ile | Thr | Pro | Glu | Gln | Ser | Lys | Arg | Ser | Thr | Met | Val | Gly | Thr | Pro | Tyr |
| | | | 395 | | | | | 400 | | | | | 405 | | | |
| Trp | Met | Ala | Pro | Glu | Val | Val | Thr | Arg | Lys | Ala | Tyr | Gly | Pro | Lys | Val | Asp |
| | 410 | | | | | 415 | | | | | 420 | | | | | 425 |
| Ile | Trp | Ser | Leu | Gly | Ile | Met | Ala | Ile | Glu | Met | Val | Glu | Gly | Glu | Pro | Pro |
| | | | | 430 | | | | | 435 | | | | | 440 | | |
| Tyr | Leu | Asn | Glu | Asn | Pro | Leu | Arg | Ala | Leu | Tyr | Leu | Ile | Ala | Thr | Asn | Gly |
| | | | 445 | | | | | 450 | | | | | 455 | | | |
| Thr | Pro | Glu | Leu | Gln | Asn | Pro | Glu | Lys | Leu | Ser | Pro | Ile | Phe | Arg | Asp | Phe |
| 460 | | | | | 465 | | | | | 470 | | | | | 475 | |
| Leu | Asn | Arg | Cys | Leu | Glu | Met | Asp | Val | Glu | Lys | Arg | Gly | Ser | Ala | Lys | Glu |
| | | | 480 | | | | | 485 | | | | | 490 | | | |
| Leu | Leu | Gln | His | Pro | Phe | Leu | Lys | Leu | Ala | Lys | Pro | Leu | Ser | Ser | Leu | Thr |
| | 495 | | | | | 500 | | | | | 505 | | | | | 510 |
| Pro | Leu | Ile | Met | Ala | Ala | Lys | Glu | Ala | Met | Lys | Ser | Asn | Arg | | | |
| | | | | 515 | | | | 520 | | | | | | 524 | | |

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Pro Glu Gln Trp Ala Arg Leu Leu Gly Thr Ser Asn Xaa Thr Lys Leu
1               5                   10                  15

Glu Gln Lys Lys
            20                                                                                  20

( 2 ) INFORMATION FOR SEQ ID NO:4:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Xaa Xaa Xaa Xaa Phe Ser Thr Gly Gly Lys Asp Pro Leu Ser Ala Asn
1               5                   10                  15

His Xaa Leu                                                                                      19

( 2 ) INFORMATION FOR SEQ ID NO:5:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

Ser Val Ile Asp Pro Ile Pro Ala Pro Val Gly Asp Ser His Val
1               5                   10                  15                                      15

( 2 ) INFORMATION FOR SEQ ID NO:6:

( i ) SEQUENCE CHARACTERISTICS:
  ( A ) LENGTH: 22 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

Asp Gly Phe Pro Ser Gly Ala Pro Ala Leu Asn Thr Lys Val Xaa Glu
1               5                   10                  15

Thr Ser Ala Val Val Thr
            20                                                                                  22

( 2 ) INFORMATION FOR SEQ ID NO:7:

( i ) SEQUENCE CHARACTERISTICS:
  ( A ) LENGTH: 21 amino acids
  ( B ) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

```
Val  Glu  Gly  Glu  Pro  Pro  Tyr  Leu  Asn  Glu  Asn  Pro  Leu  Arg  Ala  Leu
1                  5                       10                      15
Tyr  Leu  Ile  Ala  Thr
                20                                                                    21
```

( 2 ) INFORMATION FOR SEQ ID NO:8:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

```
Asp  Val  Ala  Leu  Gly  Gln  Glu  Cys  Ala  Ile  Lys  Gln  Ile  Asn  Leu  Gln
1                  5                       10                      15
Lys  Gln  Pro  Lys  Lys  Glu  Leu  Ile  Ile  Asn
                20                       25                                           26
```

( 2 ) INFORMATION FOR SEQ ID NO:9:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

```
Asp  Val  Glu  Lys  Arg  Gly  Ser  Ala  Lys  Glu  Leu  Leu  Gln  His  Pro  Phe
1                  5                       10                      15                16
```

( 2 ) INFORMATION FOR SEQ ID NO:10:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

```
Asp  Glu  Xaa  Gln  Ile  Ala  Ala  Val  Xaa  Arg  Glu  Xaa  Lys  Gln  Ala  Lys
1                  5                       10                      15
```

Glu Phe Lys Gly Ala Asn Gln Val Ile His Arg
           20                  25                    27

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:11:

Lys Glu Leu Lys Asn Pro Asn Ile Val Asn Phe
1               5                   10                  11

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

ATGGAYGARC ARCARATHGC                    20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:13:

CCNCKYTTYT CNACRTCCAT                    20

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:14:

GCCTGTAAAC ACTCTCTGCA CACAG              25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:15:

CTTCATCCAT GCAGGTTTCT GTTAC 25